US007514412B2

(12) United States Patent
Chan et al.

(10) Patent No.: US 7,514,412 B2
(45) Date of Patent: *Apr. 7, 2009

(54) ANTICANCER BIANGELOYL SAPONINS

(75) Inventors: Pui-Kwong Chan, Sugarland, TX (US); May Sung Mak, Kowloon (HK); Yun Wang, Dunedin (NZ)

(73) Assignee: Pacific Arrow Limited, North Point, Hong Kong (CN)

( * ) Notice: Subject to any disclaimer, the term of this patent is extended or adjusted under 35 U.S.C. 154(b) by 290 days.

This patent is subject to a terminal disclaimer.

(21) Appl. No.: 11/117,745

(22) Filed: Apr. 27, 2005

(65) Prior Publication Data

US 2005/0245470 A1 Nov. 3, 2005

(51) Int. Cl.
*A61K 31/704* (2006.01)
*C07H 15/256* (2006.01)
(52) U.S. Cl. .................. 514/33; 536/18.1; 536/18.2
(58) Field of Classification Search .................. 514/33; 536/18.1, 18.2
See application file for complete search history.

(56) References Cited

U.S. PATENT DOCUMENTS

| | | | |
|---|---|---|---|
| 6,616,943 B2 * | 9/2003 | Wang | 424/451 |
| 7,189,420 B2 | 3/2007 | Wang | |
| 7,262,285 B2 | 8/2007 | Chan et al. | |
| 2003/0082293 A1 | 5/2003 | Wang et al. | |
| 2003/0096030 A1 | 5/2003 | Wang et al. | |
| 2004/0138151 A1 | 7/2004 | Maes et al. | |
| 2005/0209445 A1 | 9/2005 | Gokaraju et al. | |
| 2005/0220910 A1 | 10/2005 | Chan et al. | |
| 2005/0276872 A1 | 12/2005 | Chan et al. | |
| 2005/0277601 A1 | 12/2005 | Chan et al. | |
| 2006/0111310 A1 | 5/2006 | Chan et al. | |
| 2006/0122129 A1 | 6/2006 | Chan et al. | |
| 2006/0183687 A1 | 8/2006 | Cory | |
| 2006/0263458 A1 | 11/2006 | Mak et al. | |
| 2007/0161580 A1 * | 7/2007 | Chan et al. | 514/33 |
| 2007/0196517 A1 | 8/2007 | San Martin | |
| 2007/0212329 A1 | 9/2007 | Bruck et al. | |
| 2007/0243269 A1 | 10/2007 | McNeff et al. | |
| 2007/0249711 A1 | 10/2007 | Choi et al. | |
| 2007/0254847 A1 | 11/2007 | Liu et al. | |
| 2008/0058273 A1 | 3/2008 | Yang et al. | |
| 2008/0064762 A1 | 3/2008 | Fuchs et al. | |
| 2008/0096938 A1 | 4/2008 | Evindar et al. | |
| 2008/0112925 A1 | 5/2008 | Hancock | |
| 2008/0119420 A1 | 5/2008 | Liu et al. | |

FOREIGN PATENT DOCUMENTS

| | | |
|---|---|---|
| AU | 2002348988 | 1/2004 |
| AU | 2002348988 | 11/2007 |
| CA | 2451740 | 12/2003 |
| CN | 993111010.6 | 5/1994 |
| CN | 1092991 A | 10/1994 |
| CN | 1092992 A | 10/1994 |
| CN | 1236792 C | 1/2006 |
| CN | ZL 02142258.3 | 1/2006 |
| EP | 02781502.6 | 2/2004 |
| HK | 05102536.2 | 3/2005 |
| JP | 2003-522442 | 2/2004 |
| KR | 10-2004-7002889 | 2/2004 |
| NZ | 530449 | 1/2004 |
| NZ | 530449 | 10/2007 |
| SG | 102310 | 3/2006 |
| TW | 091119471 | 8/2002 |
| TW | 93140030 | 12/2004 |
| TW | 94130519 | 9/2005 |
| WO | WO 03/017919 | 3/2003 |
| WO | WO/2005/037200 | 4/2005 |
| WO | WO/2005/063273 | 7/2005 |
| WO | WO/2006/029221 | 3/2006 |
| WO | WO/2006/116656 | 11/2006 |
| WO | PCT/US2007/077273 | 8/2007 |
| WO | PCT/US2008/002086 | 2/2008 |
| WO | WO 2008/028060 | 3/2008 |

OTHER PUBLICATIONS

U.S. Appl. No. 11/267,523, filed May 2006, Chan et al.*
U.S. Appl. No. 11/289,142, filed Jun. 2006, Chan et al.*
U.S. Appl. No. 10/906,303, filed Oct. 2005, Chan et al.*
U.S. Appl. No. 11/131,551, filed Dec. 2005, Chan et al.*
Li et al., "Two new Triterpenes from the Husks of *Xanthoceras sorbifolia*".*
The Merck Manual of Diagnosis and Therapy, seventeenth edition, 1999, Published by Merck Research Laboratories, pp. 397-398, 948-949, 1916, and 1979-1981.*
The Oxford Textbook of Oncology, 1995, published by Oxford University Press, pp. 447-453.*
Seo et al., "A New Triterpene Saponin from *Pittosporum viridiflorum* from the Madagascar Rainforest" Journal of Natural Products (2002) vol. 65, pp. 65-68.*
Tuntiwachwuttikul et al. "A Triterpenoid Saponin from *Maesa Ramentacea*" Phytochemistry (1997) vol. 44, No. 3, pp. 491-495.*
D'Acquarica et al., "Isolation and Structure Elucidation of four new triterpenoid estersaponins from fruits of *Pittosporum tobira* AIT" Tetrahedron (2002) vol. 58, pp. 10127-10136.*
Arda, et al. "Saniculoside N from *Sanicula europaea* L." Journal of Natural Products (1997), 60(11), 1170-1173.
Azam, et al. "A triterpenoidal sapogenin from the seeds of *Doclonaea viscosa* Linn," Indian Journal of Chemistry, Section B: Organic Chemistry Including Medicinal Chemistry (1993), 32B(4), 513-14.
Barre, et al. "A bioactive triterpene from *Lantana camara*." Phytochemistry (1997), 45(2), 321-324.
Barua, et al. "Triterpenoids. XXIX. Structure of barringtogenol B-a new triterpenoid sapogenin from *Barringtonia acutangula*." Tetrahedron (1968), 24(3), 1113-17.
Beeby, et al. "Angeloyl chloride: synthesis and utilization in the partial synthesis of lantaden A (rehmannic acid)." Tetrahedron Letters (1977), (38), 3379-82.
Brown, et al. "The relation of chemical structure to the icterogenic and photosensitizing action of some naturally occuring and synthetic triterpene acids," South African Journal of Laboratory and Clinical Medicine (1963), 9 282-72.
Brown, et al. "Biliary excretion in the rabbit. II. The relation between the chemical structure of certain natural or synthetic pentacyclic triterpenes and their icterogenic activity. 2. The substitutions on carbon atoms 17, 29, 20, and 22," Proc. Roy. Son. (London) Ser. B (1964), 160 (979), 248-57.
Chen, et al. "Studies on the constituents of *Xanthoceras sorbifolia* Bunge. (I)." Shoyakugaku Zasshi (1984), 38(2), 203-6.
Chen, et al. "Studies on the constituents of *Xanthoceras sorbifolia* Bunge. II." Chemical & pharmaceutical bulletin (Sep. 1984), 32(9), 3378-83.

Chen, et al. "Studies on the constituents of *Xanthoceras sorbifolia* Bunge. III." Chemical & Pharmaceutical Bulletin (1985), 33(1), 127-34.

Chen, et al. "Studies on the constituents of *Xanthoceras sorbifolia* Bunge. IV. Structures of the minor prosapogenins." Chemical & Pharmaceutical Bulletin (1985), 33(3), 1043-8.

Chen, et al. "Studies on the constituents of *Xanthoceras sorbifolia* Bunge. V. Major saponins from the fruits of *Xanthoceras sorbifolia* Bunge." Chemical & Pharmaceutical Bulletin (1985), 33(4), 1387-94.

Cheng, et al. "Two new sterols in husk of *Xanthoceras sorbifolia*." Zhongcaoyao (2001), 32(3), 199-201.

Chakravarty, et al. "Triterpenoid prosaponins from leaves of *Maesa chisia* var. angustifolia," Phytochemistry (1987), 26(8), 2345-9.

Cui, et al. "2D NMR structure determination of five flavonoids from the wood of *Xanthoceras sorbifolia* Bunge." Shenyang Yaoxueyuan Xuebao (1991), 8(1), 36-8, 57.

Cui, et al. "Blood-activating constituents of Wenguanmu (*Xanthoceras sorbifolia*)." Zhongcaoyao (1987), 18(7), 297-8, 296.

Cui, et al. "The application of the microcomputer in the study of Chinese herb and natural drugs. 1. The Basic program used for the design of liquid-liquid extraction and forecasting the results of extraction and separation." Shenyang Yaoxueyuan Xuebao (1986), 3(2), 79-84.

Eakins, et al. "The effect of three triterpene acids and sporidesmin on the enzyme activities of rat liver plasma membranes." Chemico-Biological Interactions (1978), 21(1), 117-24.

Eakins, et al. "Studies on bile secretion with the aid of the isolated perfused rat liver. II. The effect of two further pentacyclio triterpenes, asiatic acid and 22-engeloytoxyoleanolicacid." Chemico-Biological Interactions (1976), 21(1), 79-87.

Hart, et al. "New triterpenes of *Lantana camara*. A comparative study of the constiuents of several taxa." Australian Journal of Chemistry (1976), 29(3), 655-71.

Hopkins, et al. "Eicosenoic acid and other fatty acids of *Sapindaceae* seed oils." Lipids (1967), 2(3), 258-60.

Hu, et al. "Preparation of high-heating value synthetic liquid fuels." Faming Zhuanli Shenqing Gongkai Shuomingshu (1999), 4 pp.

Hu, et al. "Preparation of liquid fuels having high caloric value." Faming Zhuanli Shenqing Gongkai Shuomingshu (1994), 5 pp.

Huang, et al. "Chemical constituents of Wenguanmu (*Xanthoceras sorbifolla*) (I)." Zhongcaoyao (1987), 18(5), 199-202.

Huang, et al. "Preliminary studies on absorption and accumulation of atmospheric lead and cadmium by woody plants." Linye Kexue (1982), 18(1), 93-7.

Kim, et al. "Fatty-acid composition of vegetable oils." Choson Minjujuui Inmin Konghwaguk Kwahagwon Tongbo (1985), (3), 43-6.

Koike, et al. "New triterpenoid saponins from *Maesa japonica*." Journal of Natural Products (1999), 62(2), 228-232.

Kuang, et al. "Anti-inflammatory effects of n-butanol extract of *Xanthoceras sorbifolla* Bunge." Shenyang Yaoke Daxue Xuebao (2001), 18(1), 53-56.

Li, et al. "Medicine for enhancing mental activity." Faming Zhuanli Shenqing Gongkai Shuomingshu (1994), 7 pp.

Li, et al. "*Xanthoceras sorbifolla* fruit extracts for enhancing mental activity." Faming Zhuanli Shenqing Gongkai Shuomingshu (1994), 6 pp.

Li, et al. "Identification of fatty acids in the kernel oil of *Xanthoceras sorbifolia* Bge, with GC-MS." Zhiwu Ziyuan Yu Huanjing (1993), 2(2), 28-32.

Li, et al. "Isolation and structural determination of triterpene alcohols and 4-methylsterols in unsaponifable fraction of the oil from *Xanthoceras sorbifolia* Bge." Linye Kexue (1984), 20(4), 397-402.

Li, et al. "Eremophilenolides and other constituents from the roots of *Ligularia sagitta*." Planta Medica (2003), 69(4), 356-360.

Li, et al. "New gualanolides and xanthine oxidase inhibitory flavonols from *Ajania fruticulose*." Journal of Natural Products (1999), 62(7), 1053-1055.

Liu, et al. "The components of *Cacalia tangutica*." Bulletin of the Korean Chemical Society (2004), 25(7), 1078-1080.

Ma, et al. "A novel protoilludane sesquiterpene from the wood of *Xanthoceras sorbifolia*." Chinese Chemical Letters (2004), 15(1), 65-67.

Ma, et al. "Screening of Chinese and Mongolian herbal drugs for anti-human immunodeficiency virus type 1 (HIV-1) activity." Phytotherapy Research (2002), 16(S1), 186-189.

Ma, et al. "Inhibitory effects on HIV-1 protease of constituents from the wood of *Xanthoceras sorbifolia*." Journal of natural products (Feb. 2000), 63(2), 238-42.

Manato, et al. "New triterpenoids from *Lantana camara*: Isomerissation of the angeloyl moiety of lantadene a during catalytic hydrogenation." Journal of the Indian Chemical Society (1999), 76(11-12), 723-726.

Meng, et al. "Antifungal highly oxygenated guaianolides and other constituents from *Ajanla fruticulosa*." Phytochemistry (2001), 58(7), 1141-1145.

Nakamura, et al. "Inhibitory effects of some traditional medicines on proliferation of HIV-1 and its protease." Yakugaku Zasshi (2004), 124(8), 519-529.

42. Nethaji, et al. "Molecular structure of lantadene-B&C, triterpenoids of *Lantana camera*, rod variety: lantadene-B. 228-engelooyloxy-oxoolean-12-en-28-oic acid; lantadene-C, 22 B-(S)-2'-methyl butanoyloxy-3-oxcolaan-12-en-28-oic acid." Journal of Crystallographic and Spectroscopic Research (1993), 23(6), 469-72.

Plouvier, et al. "Fraxoside and coumarin heterosides occuring in various botanical groups." Comptes Rendus des Seances de l'Academie des Sciences, Serie D: Sciences Naturelles (1968), 267 (22), 1883-5.

Plouvier, et al. "Flavone heterosides: kaempterol 3-rhamnoglucoside, myricitrin, linarin, and saponarin." Comptes Rendus des Seances de l'Academie des Sciences, Serie D: Sciences Naturelles (1966), 262(12), 1368-71.

Plouvier, et al. "Oil of the seeds of *Xanthoceras sorbifolia* Bunge and of *Koelreuteria paniculata* Laxm." Compt. rend. (1946), 222 916-17.

Sakurai, et al. "Assamicin I and II, novel triterpanoid saponins with insulin-like activity from *Aesculus assamica* Griff." Bioorganic & Medicinal Chemistry Letters (2002), 12(5), 807-810.

Semikhov, et al. "Comparative study of the amino acid composition of the embryo in grasses (Poaceae) and other flowering plants." Botanicheskil Zhumal (Sankt-Peterburg, Russian Federation) (1994), 79(3), 83-92.

Sharma, et al. "Molecular structure, polymorphism, and toxicity of lantadene A, the pentacyclic triterpenoid from the hepatotoxic plant *Lantana camara*." Journal of biochemical toxicology (1991 Spring), 6(1), 57-63.

Shang-Jiang, et al. "Constituents of Shashen (*Adenophora axilliflora*)." Planta Medica (1986), (4), 317-20.

Sindambiwe, et al. "*Triterpenoid saponins* from *Maesa lanceolate*." Phytochemistry (1996), 41(1), 269-77.

Singh, et al. "Biotransformation of lantadene A (22β-angeloyloxy-3-oxoolean-12-en-28-olc acid), the pentacyclic triterpenoid, by *Alcallgenes faecalls*." Biodegradation (1999), 10(5), 373-381.

Tian, et al. "Study on the vegetative storage proteins in temperate hardwoods of fifteen families." Xibel Zhiwu Xuebao (2000), 20(5), 835-841.

"Triterpenoids. XVI. The constitution of rehmannic acid." Journal of the Chemical Society, Abstracts (1954), 900-3.

Tuntiwachwuttikul, et al. "A triterpenoid saponin from *Maesa ramentacea*." Phytochemistry (1997), 44(3), 491-495.

Voutquenne, et al. "Triterpenoid saponins and acylated prosapogenins from *Harpullia austro-caledonica*." Phytochemistry (2002), 59(8), 825-832.

Wang, et al. "Chemical constituents of the oil and kernels of *Xanthoceras sorbifolia* Bunge." Zhiwu Xuebao (1981), 23(4), 331-3.

Waechter, et al. "Antitubercular Activity of Triterpenoids from *Lippia turbinata*." Journal of Natural Products (2001), 64(1), 37-41.

Yan, et al. "Separation, identification and determination of the unsaponifiable matters in vegetable oils." Beijing Shifan Daxue Xuebao, Ziran Kexueban (1985), (1), 53-8.

Yan, et al. "Isolation, content analysis and structural determination of sterols in unsaponifiable fraction of the oil from *Xanthoceras sorbifolla* Bge." Linye Kexue (1984), 20(4), 389-98.

Yang, et al. "Extraction of total saponin, fat, protein, and saccharide from *Xanthoceras sorbifolia*." Faming Zhuanli Shenqing Gongkai Shuomingshu (2002), 4 pp.

Yang, et al. "Application of the extract of *Xanthoceras sorbifolia* shell in preparing the food and medicine for improving brain functions." Faming Zhuanil Shenqing Gongkai Shuomingshu (2002), 6 pp.

Yang, et al. "Two new triterpenoid saponins from the seeds of *Aesculus chinensis*." Chinese Chemical Letters (2000), 11(2), 139-142.

Zhang, et al. "Quantitative determination of myricetin and quercetin in *Xanthoceras sorbifolia* Bunge by HPLC." Shenyang Yaoke Daxue Xuebao (2000), 17(3), 194-196.

Zhang, et al. "Studies on chemical constituents of *Xanthoceras sorbifolia* Bunge." Yaoxue Xuebao (2000), 35(2), 124-127.

Zhao, et al. "Four new triterpene saponins from the seeds of *Aesculus chinensis*." Journal of Asian Natural Products Research (2003), 5(3), 197-203.

Zhao, et al. "Three new triterpene saponins from the seeds of *Aesculus chinensis*." Chemical & Pharmaceutical Bulletin (2001), 49(5), 626-628.

Zheng, et al. "Triterpenoids from *Mosia chinensis*." Indian Journal of Chemistry, Section B: Organic Chemistry Including Medicinal Chemistry (2000). 39B(11), 875-878.

Apers, et al. "New acylated triterpenoid saponins from *Maesa lanceolata*." Phytochemistry 52 (1999), 1121-1131.

D'Acquarica, et al. "Isolation and structure elucidation of four new triterpenoid estersaponins from fruits of *Pittosporum tobira* AIT." Tetrahedron 58 (2002) 10127-10136.

Jiang, et al. "Six Triterpenoid Saponins from *Maesa laxiflora*." J. Nat. Prod. 1999, 62, 873-876.

Lu, et al. "Triterpenoid saponins from the roots of tea plants (*Camellia sinensis* var. assamica)." Phytochemistry 53 (2000) 941-946.

Seo, et al. "A New Triterpene Saponin from *Pittosporum viridiflorum* from the Madagascar Rainforest." J. Nat. Prod. 2002, 65, 65-68.

Yang, et al. "Anti-HIV-1 Protease Triterpenoid Saponins from the Seeds of *Aesculus chinensis*." J. Nat. Prod. 1999, 62, 1510-1513.

Written Opinion of the International Searching Authority for PCT/US04/33359, filed Oct. 8, 2004 for Pacific Arrow Limited et al., dated Apr. 12, 2005.

International Search Report for PCT/US04/33359, filed Oct. 8, 2004 for Pacific Arrow Limited et al., dated Apr. 12, 2005.

Written Opinion of the International Searching Authority for PCT/US04/43465, filed Dec. 23, 2004 for Pacific Arrow Limited et al., dated May 17, 2005.

International Search Report for PCT/US04/43465, filed Dec. 23, 2004 for Pacific Arrow Limited et al., dated May 17, 2005.

Supplementary European Search Report issued on Jul. 6, 2005 for Fountain Silver Limited et al., European Patent Application No. 02781502.6.

U.S. Appl. No. 60/617,379, filed Oct. 8, 2004, May Sung Mak.
U.S. Appl. No. 60/613,811, filed Sep. 27, 2004, Mak, et al.
U.S. Appl. No. 60/607,858, filed Sep. 7, 2004, May Sung Mak.
U.S. Appl. No. 60/532,101, filed Dec. 23, 2003, Wang, et al.
U.S. Appl. No. 60/509,851, filed Oct. 9, 2003, Wang, et al.
U.S. Appl. No. 60/675,807, filed Apr. 27, 2005, Chan, et al.
U.S. Appl. No. 60/841,727, filed Sep. 1, 2006, May Sung Mak.
U.S. Appl. No. 60/675,282, filed Apr. 27, 2005, Chan, et al.
U.S. Appl. No. 11/683,198, filed Mar. 7, 2007, Chan, et al.

PCT International Search Report issued on Feb. 6, 2007 for Pacific Arrow Limited, International App'l No. PCT/US2005/031900.

PCT Written Opnion of the International Searching Authority issued on Feb. 6, 2007 for Pacific Arrow Limited, International App'l No. PCT/US2005/031900.

PCT International Preliminary Report on Patentability issued on Mar. 22, 2007 for Pacific Arrow Limited, International App'l No. PCT/US2005/031900.

PCT International Preliminary Report on Patentability issued on Dec. 23, 2005 for Pacific Arrow Limited, International App'l No. PCT/US2004/033359.

PCT International Search Report Issued on Nov. 13, 2006 for Pacific Arrow Limited, International App'l No. PCT/US2006/016158.

PCT Written Opinion of the International Searching Authority issued on Nov. 13, 2006 for Pacific Arrow Limited, International App'l No. PCT/US2006/016158.

Voutquenne, et al. "Structure- Activity Relationships of Haemolytic Saponins" Pharmaceutical Biology (2002), vol. 40, No. 4, pp. 253-262.

Sirtori, C., "Aescin: Pharmacology, Pharmacokinetic Profile" Pharmacological Research(2001) vol. 44, No. 3, pp. 183-193.

Oda, K. et al., "Adjuvant and Haemolytic Activities of 47 Saponins Derived from Medicinal and Food Plants" Biol. Chem. (2000) vol. 381, pp. 67-74.

Notice of Acceptance for Wang, Yun, Australia Patent No. App'l No. 2002348988, filed Jan. 21, 2004, Dated Jul. 26, 2007.

Notice of Acceptance for Wang, Yun, New Zealand Patent No. App'l No. 530449, filed Jan. 6, 2004, Dated Jun. 29, 2007.

European Office Communication for Wang, Yun, European App'l No. EP 02781502.6, filed Feb. 25, 2004, Dated Jul. 20, 2007.

European Office Communication for Wang, Yun, European App'l No. EP 02781502.6, filed Feb. 25, 2004, Dated Oct. 12, 2005.

European Supplementary Search Report for Wang, Yun, European App'l No. EP 02781502.6, filed Feb. 25, 2004, Dated Jul. 6, 2005.

New Zealand Examination Report for Wang, Yun, New Zealand Patent No. App'l No. 530449, filed Jan. 6, 2004, Dated Feb. 15, 2006.

New Zealand Examination Report for Wang, Yun, New Zealand Patent No. App'l No. 530449, filed Jan. 6, 2004, Dated Apr. 10, 2007.

U.S. Office Action for Mak, et al., U.S. Appl. No. 11/412,659, filed Apr. 27, 2006, Dated Mar. 8, 2007.

U.S. Final Office Action for Mak, et al., U.S. Appl. No. 11/412,659, filed Apr. 27, 2006, Dated Sep. 5, 2007.

U.S. Office Action for Chan, et al., U.S. Appl. No. 11/131,551, filed May 17, 2005, Dated Jan. 22, 2007.

U.S. Notice of Allowability for Chan, et al., U.S. Appl. No. 11/131,551, filed May 17, 2005, Dated May 11, 2007.

U.S. Office Action for Chan, et al., U.S. Appl. No. 11/289,142, filed Nov. 28, 2005, Dated Sep. 27, 2007.

U.S. Office Action for Chan, et al., U.S. Appl. No. 11/267,523, filed Nov. 4, 2005, Dated Sep. 27, 2007.

U.S. Office Action for Chan, et al., U.S. Appl. No. 10/906,303, filed Feb. 14, 2005, Dated Feb. 12, 2007.

U.S. Office Action for Chan, et al., U.S. Appl. No. 10/906,303, filed Feb. 14, 2005, Dated Jul. 27, 2007.

U.S. Office Action for Chan, et al., U.S. Appl. No. 11/117,760, filed Apr. 27, 2005, Dated Jun. 29, 2007.

U.S. Office Action for Chan, et al., U.S. Appl. No. 11/117,760, filed Apr. 27, 2005, Dated Aug. 20, 2007.

Chan, Pui-Kwong, 2007, "Acylation with diangeloyl groups at C21-22 positions in triterpenoid saponins is essential for cytotoxcity towards tumor cells", Biochemical Pharmacology 73(2007): 341-350.

Lavaud, et al., 1992, "Saponins from *Steganotaenia arallacea*", Phycochemistry, 31(9):3177-3181.

Zhang, et al., 2007, "Cytotoxic triterpenoid saponins from the fruits of *Aesculus pavia* L", Phytochemistry 68(2007): 2075-2086.

U.S. Appl. No. 11/289,142, filed Nov. 28, 2008, Chan et al.

PCT International Preliminary Report on Patentability for Pacific Arrow Limited, et al., International Application No. PCT/US2006/016158, filed Apr. 27, 2006, Dated Oct. 30, 2007.

PCT International Preliminary Report on Patentability for Pacific Arrow Limited, International App'l No. PCT/US2004/043465, filed Dec. 23, 2004, Dated Feb. 7, 2006.

U.S. Office Communication for Chan, et al., U.S. Appl. No. 11/117,760, filed Apr. 27, 2005, Dated Feb. 8, 2008.

U.S. Office Action for Mak, et al., U.S. Appl. No. 11/412,659, filed Apr. 27, 2006, Dated Feb. 20, 2008.

U.S. Office Action for Chan, et al., U.S. Appl. No. 11/289,142, filed Nov. 28, 2005, Dated Apr. 14, 2008.

U.S. Office Action for Chan, et al., U.S. Appl. No. 10/906,303, filed Feb. 14, 2005, Dated Jan. 4, 2008.

Akihisa, et al., 2006, "Cancer Chemopreventive Effects and Cytotoxic Activities of the Triterpene Acids from the Resin of *Boswellia carteri*", Biological & Pharmaceutical Bulletin, vol. 29(9):1976-1979.

Bang, et al., 2007, "Facile Synthesis of Trisaccharide Moiety Corresponding to Antitumor Activity in Triterpenoid Saponins Isolated from Pullsatilla Roots", Chemical & Pharmaceutical Bulletin, vol. 55(12): 1734-1739.

Chang, et al., 2007, "Biologically Active Triterpenoid Saponins from *Ardisia japonica*", Journal of Natural Products, vol. 70(2): 179-187.
Fujioka, et al., 2006, "Antiproliferative Constituents from Umbelliferae Plants. New Triterpenoid Glycosides from the Fruits of *Bupleurum rotundifolium*", Chemical & Pharmaceutical Bulletin, vol. 54 (12):1694-1704.
Li, et al., 2005, "Two New Triterpenes from the Husks of *Xanthoceras Sorbifolia*", Planta Medica, vol. 71:1068-1070.
Liang, et al., 2006, "Triterpenoid Saponins from *Lysimachia davurica*", Chemical & Pharmaceutical Bulletin, vol. 54 (10):1380-1383.
Ma, et al, 2008, "Cytotoxic Triterpenoid Saponins Acylated with Monoterpenic Acid from *Pithecellobium lucidum*", Journal of Natural Products, vol. 71(1): 41-46.
Puiffe, et al., 2007, "Characterization of Ovarian Cancer Ascites on Cell Invasion, Proliferation, Spheroid Formation, and Gene Expression in an In Vitro Model of Epithelial Ovarian Cancer" Neoplasia, vol. 9(10):820-829.
Rabi, et al., 2007, "Novel triterpenoid 25-hydroxy-3-oxoolean-12-en-28-oic acid induces growth arrest and apoptosis in breast cancer cells", Breast Cancer Research & Treatment, vol. 101:27-36.
Ricciardelli, et al., 2006, "Extracellular Matrix of Ovarian Tumors", Seminars in Reproductive Medicine, vol. 24(4): 270-282.
Sporn, et al., 2007, "Platforms and Networks in Triterpenoid Pharmacology", Drug Development Research, vol. 68:174-182.
Talmadge, James E., 2008, "Follistatin as an Inhibitor of Experimental Metastasis", Clinical Cancer Research, vol. 14(3) 624-626.
The Merck Manual of Diagnosis and Therapy, 17th Edition, 1999, Published by Merck Research Lanoratories, pp. 397-398, 948-949, 1916, and 1979-1981.
The Oxford Textbook of Oncology, 1995, published by Oxford University Press, pp. 447-453.
Ushijima, et al, 2008, "Triterpene Glycosides from the Roots of *Codonopsis lanceolata*", Chemical & Pharmaceutical Bulletin, vol. 56(3) 308-314.
Voutquenne, et al., 2005, "Haemolytic Acylated Triterpenoid saponins from *Harpullia austro-caledonica*". Phytochemistry, vol. 66: 825-835.
Wang, et al., 2008, "Bioactive Triterpene Saponins from the Roots of *Phytolacca Americana*", Journal of Natural Products, vol. 71(1): 35-40.
Wei, et al., 2004, "Anti-inflammatory Triterpenoid Saponins from the Seeds of *Aesculus chinensis*", Chemical & Pharmaceutical Bulletin, vol. 52(10): 1246-1248.
Yadava, et al., 2008, "New antibacterial triterpenoid saponin from *Lactuca scariola*", Fitoterapia, vol. 1:1-5.
U.S. Appl. No. 60/795,417, filed Apr. 27, 2006, Mak, et al.
U.S. Appl. No. 60/890,380, filed Feb. 16, 2007, Chan, et al.
U.S. Appl. No. 60/947,705, filed Jul. 3, 2007, Chan, et al.
PCT International Preliminary Report on Patentability, Apr. 11, 2006, for Pacific Arrow Limited, International App'l No. PCT/US2004/033359, filed Oct. 8, 2004.
PCT International Search Report, Jul. 7, 2008, for Pacific Arrow Limited et al., International App'l No. PCT/US2008/002086, filed Feb. 15, 2008.
PCT Written Opinion of the International Searching Authority, Jul. 7, 2008, for Pacific Arrow Limited et al., Information App'l No. PCT/US2008/002086, filed Feb. 15, 2008.
Chinese Office Action, Aug. 27, 2004. for Wang, Yun, Chinese Application No. 02142258.3, Filed Aug. 28, 2002. (w/English Translation).
Chinese Office Action, May 27, 2005, for Wang, Yun, Chinese Application No. 02142258.3, Filed Aug. 28, 2002. (w/English Translation).
Taiwan Office Action, Sep. 14, 2004, for Wang, Yun, Taiwan Application No. 091119471, filed Aug. 28, 2002. (w/English Translation).
Taiwan Office Action, Apr. 26, 2005, for Wang, Yun, Taiwan Application No. 091119471, filed Aug. 28, 2002. (w/English Translation).
Zhu et al., 1997, "Preliminary chemical analysis of Wenguanguo and study of its comprehensive utilization", Journal of Land & Natural Resources Research, vol. 1:69-71. (w/English Translation).

\* cited by examiner

*Primary Examiner*—Shaojia Anna Jiang
*Assistant Examiner*—Eric S Olson
(74) *Attorney, Agent, or Firm*—Law Offices of Albert Wai-Kit Chan, PLLC

(57) ABSTRACT

Novel compounds such as compounds designated herein as Y or Y3, Y1, Y2, Y8, Y9 and Y10 are disclosed. These compounds have anticancer activity. The compounds of the present invention are obtainable from plants in the sapindaceae family, such as *Xanthoceras sorbifolia*, or other natural sources or products. The compounds of the present invention may also be synthesized chemically.

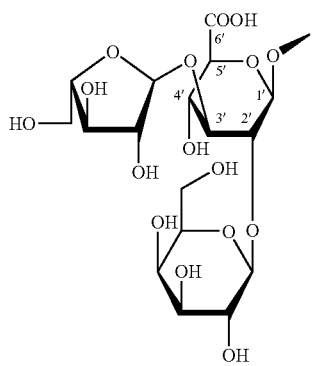

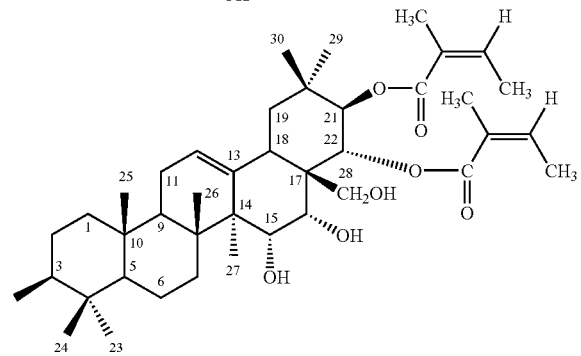

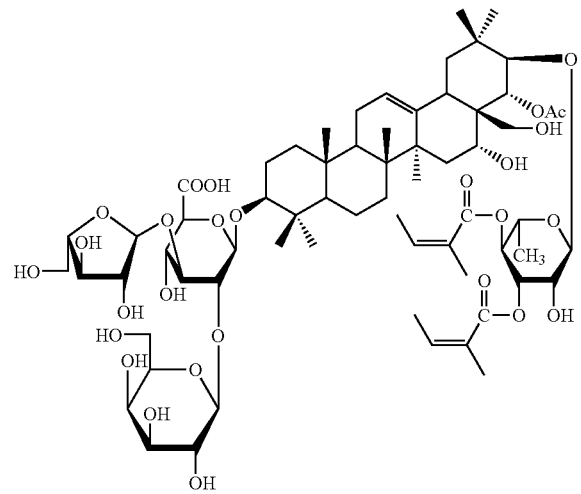

-continued
$Y_2$
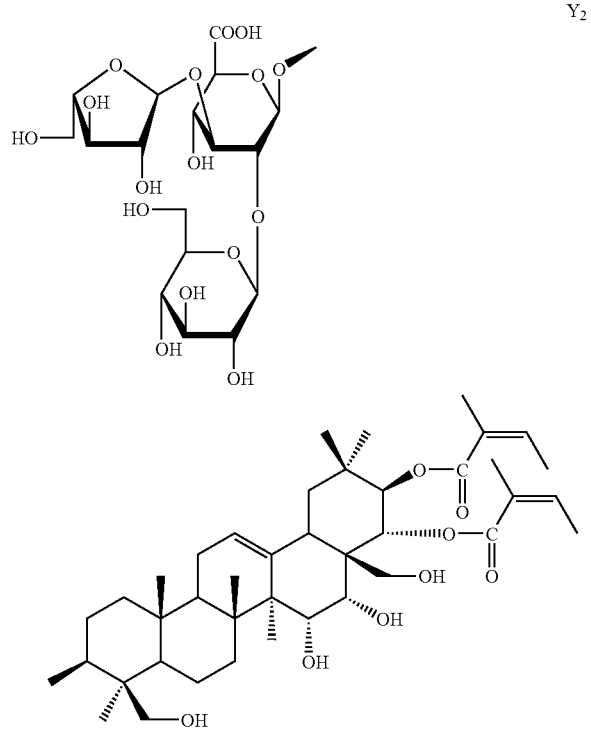
$Y$-8
-continued
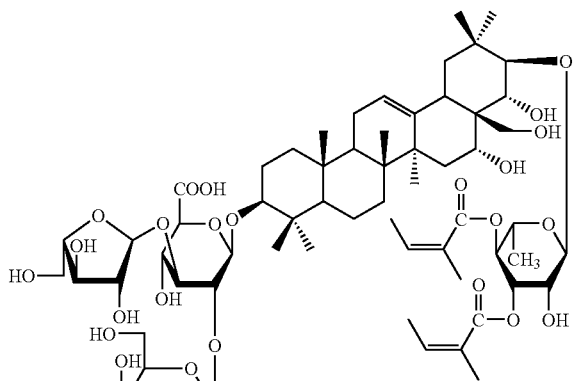
$Y$-9
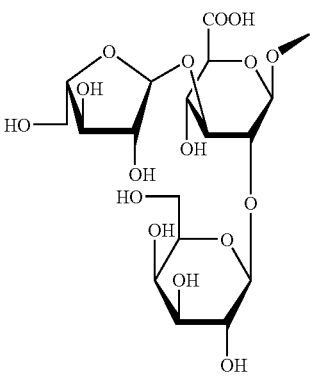
$Y$-10
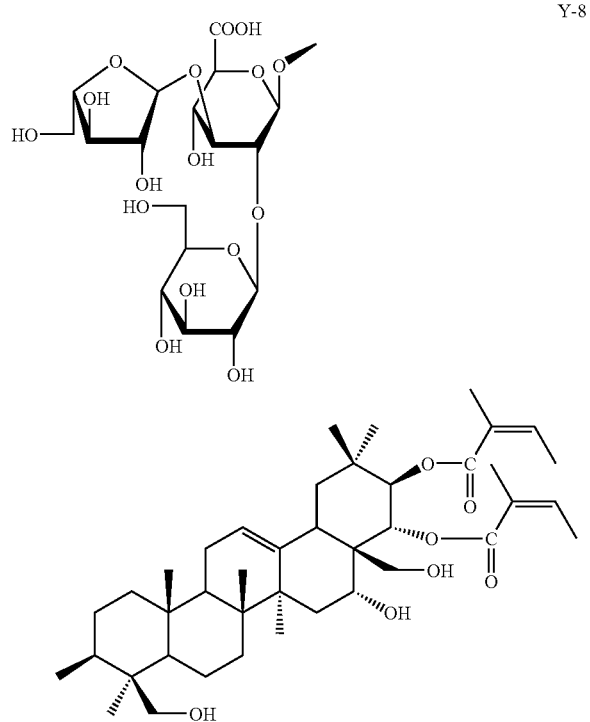
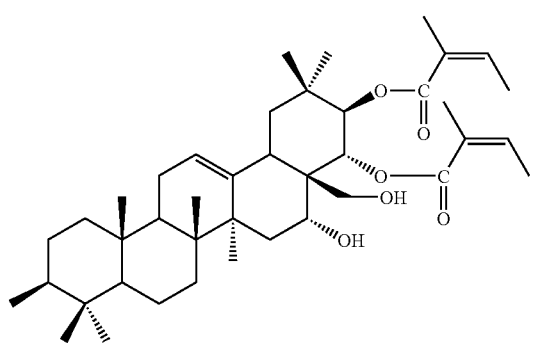
23 Claims, 66 Drawing Sheets

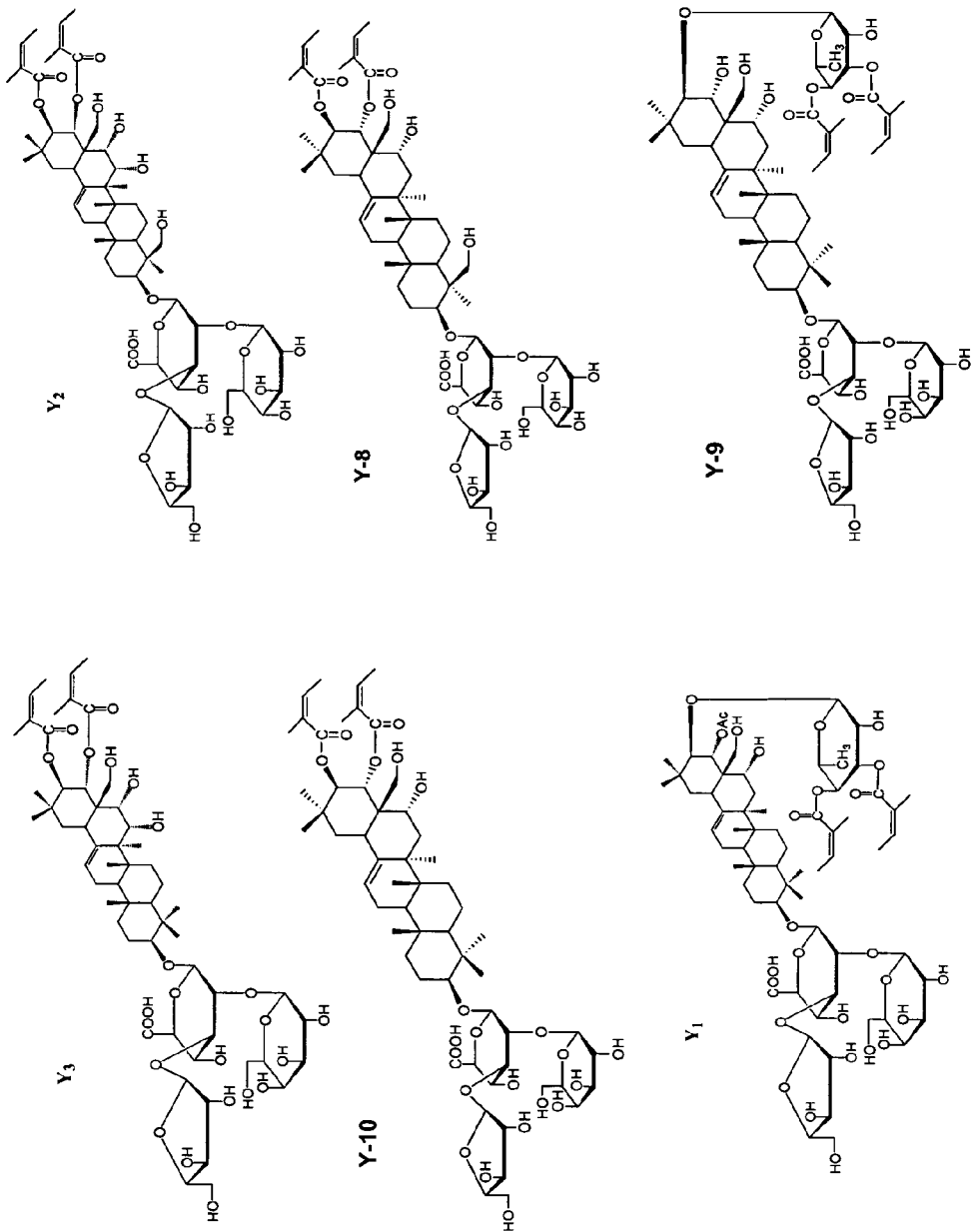
Figure 1. Structure of six anticancer Saponins with biangeloyl groups (Y3 (Y), Y2, Y8, Y10, Y1 and Y9)

Figure 2
Anticancer activity of Compound Y
(A) Points graph
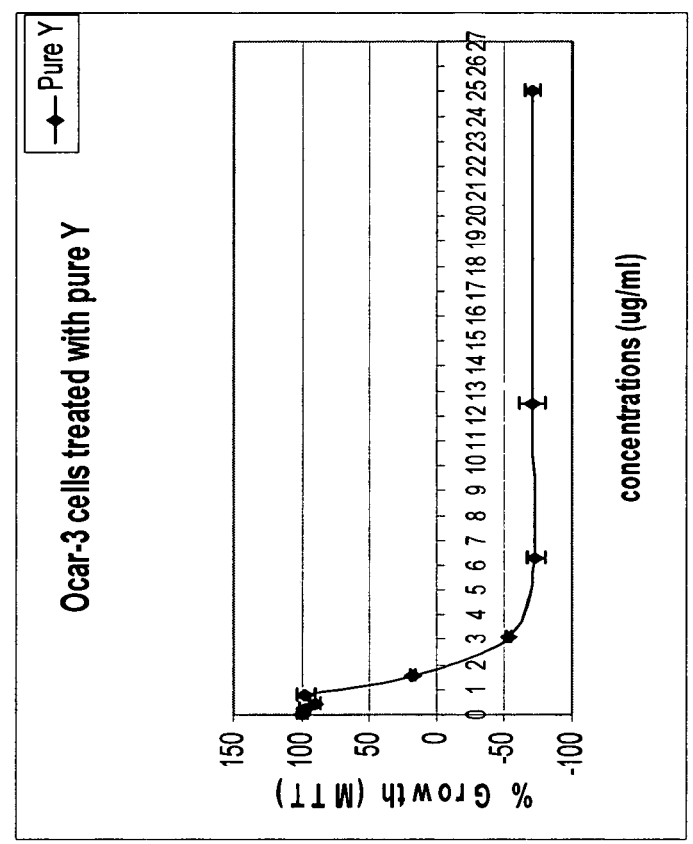
(B) X,Y linear graph
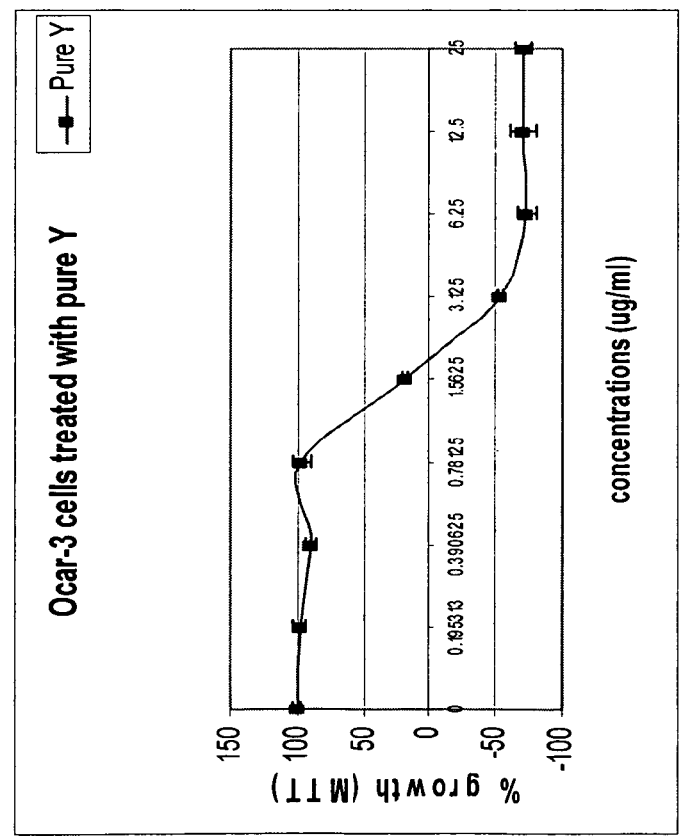

Y1 and Y2 activity on Ovarian caner cells

Anticancer activity of Compounds Y, Y8, Y9 and Y10.

Figure 5. Consensus structure of compound Ys (Y,Y2, Y8 and Y10)
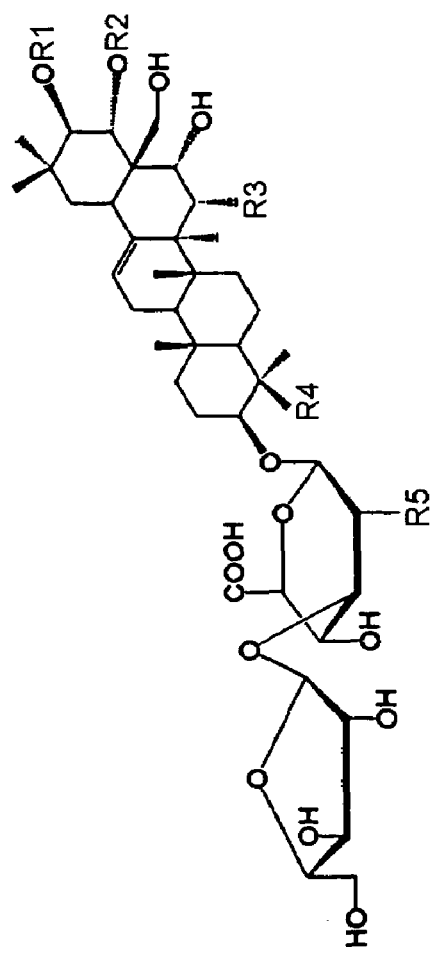
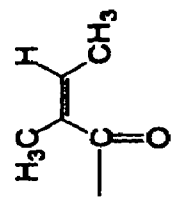
Angeloyl =
R1 = Angeloyl
R2 = Angeloyl
R3 = OH or H
R4 = CH3 or CH₂OH
R5 = D- glucose, D-galactose,

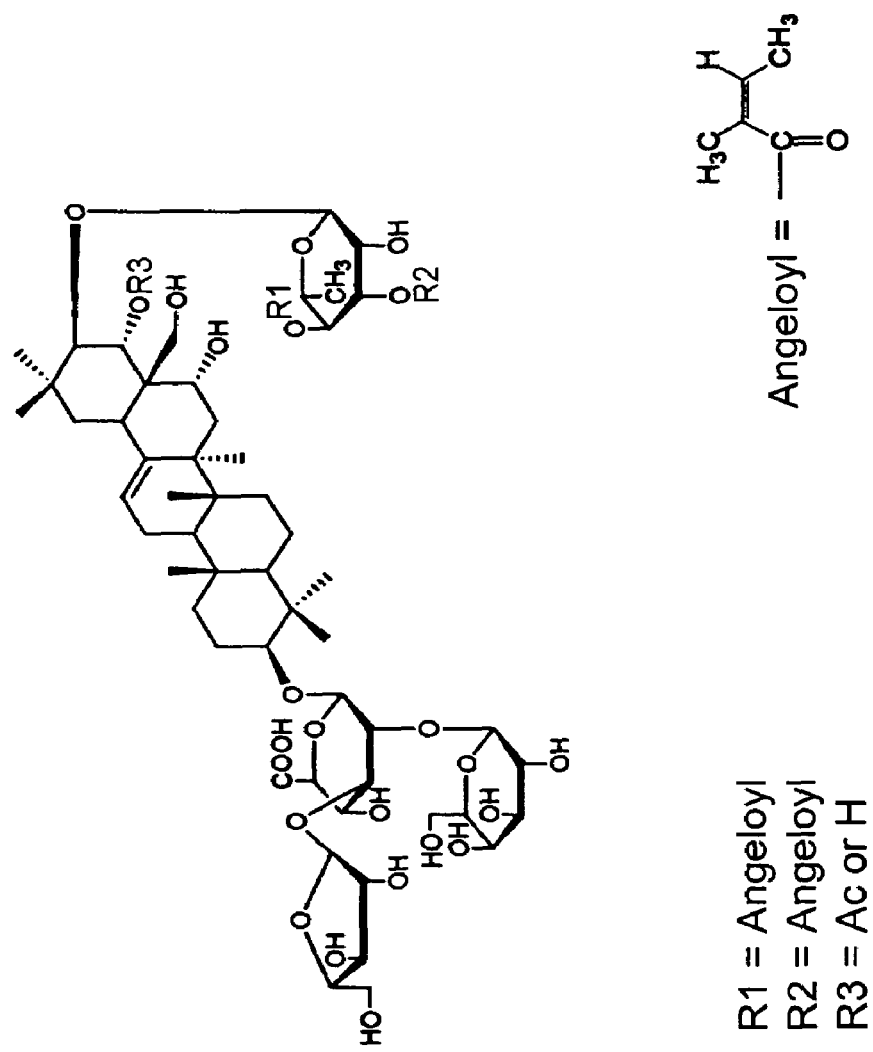
Figure 6. Consensus structure of Ys (Y1 and Y9)
R1 = Angeloyl
R2 = Angeloyl
R3 = Ac or H

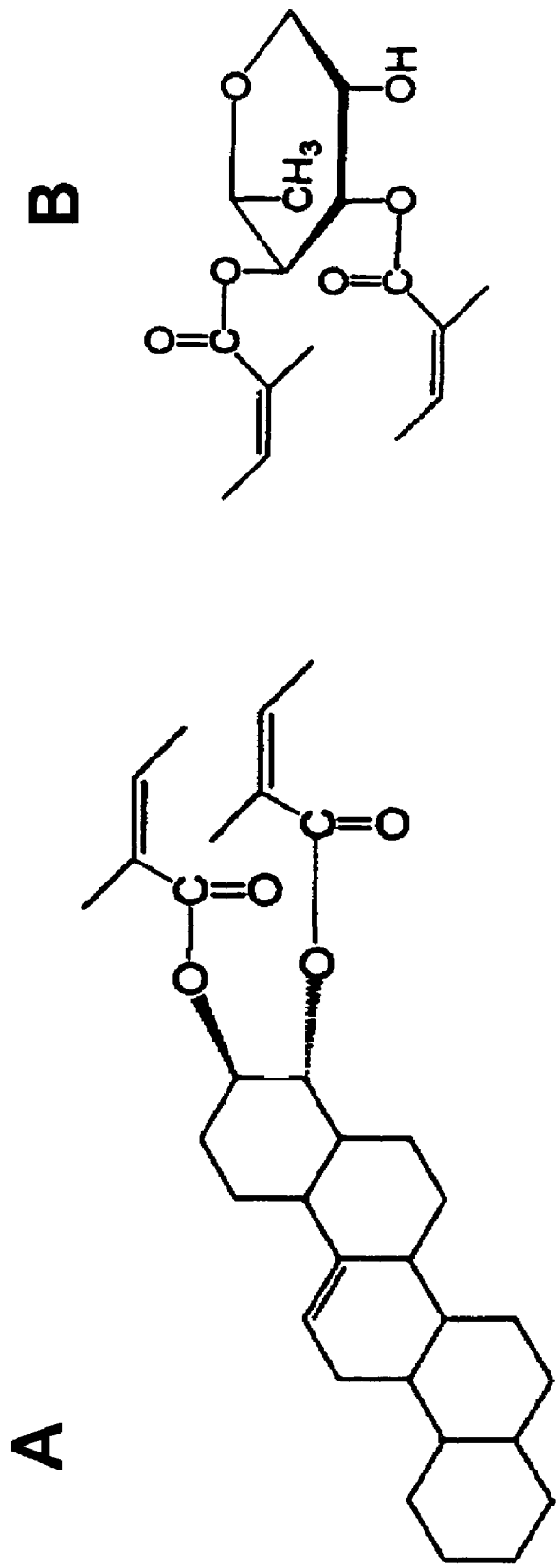
Figure 7. Biangeloyl group situated in trans-position on a planar structure.

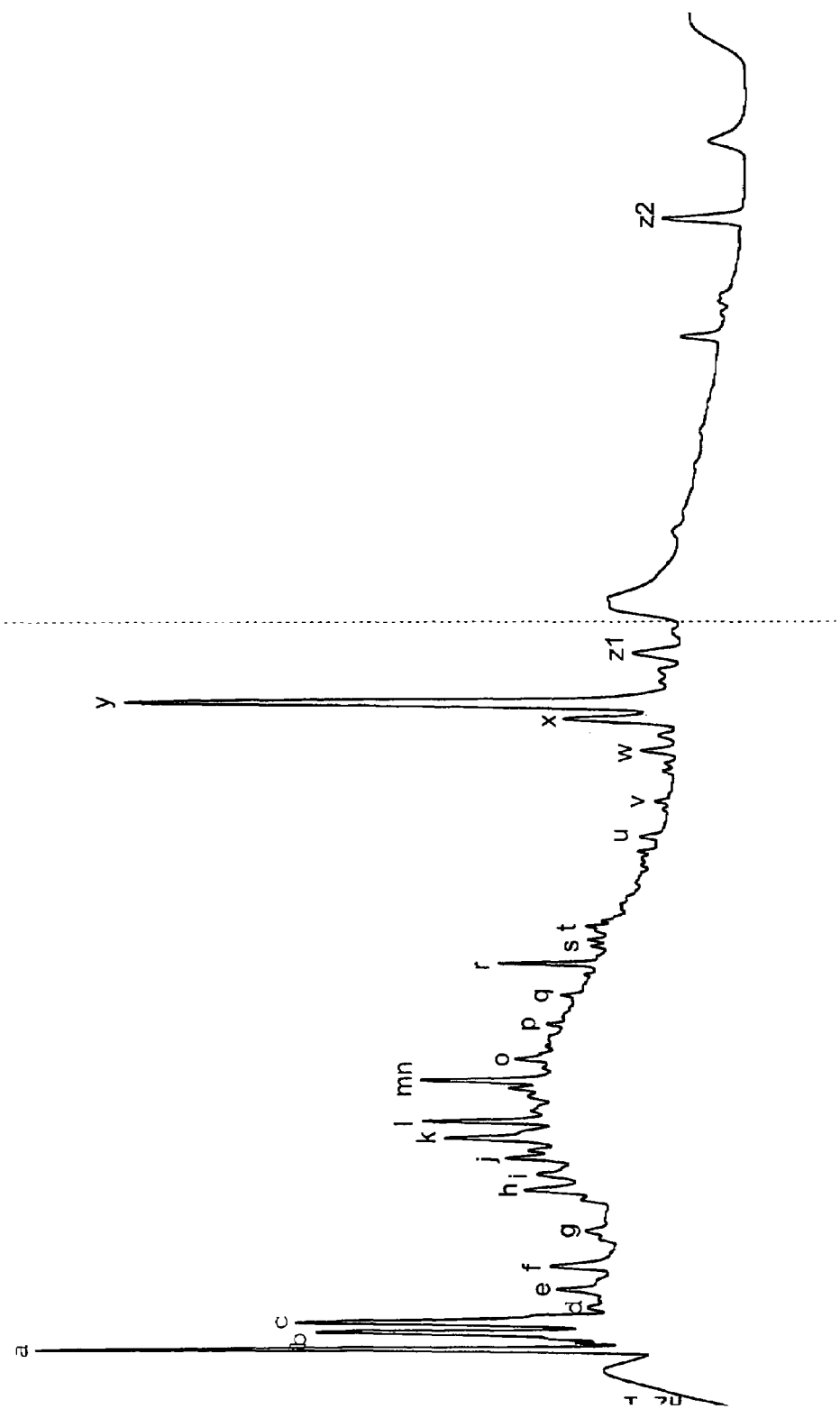

FPLC profile of Plant extract

Cell growth activity of fractions of plant extract

Purification of Factions Ys

Purification of Y8-Y10 with HPLC (iso-45)

Inhibition of Ovarian cancer growth by plant extract

Comparison of Potency of Y in ovary and cervix cancer cells

Growth curve of cancer cells after treatment with extract

Growth curve of cancer cells after treatment with extract

Growth curve of cancer cells after treatment with extract

Growth curve of cancer cells after treatment with extract

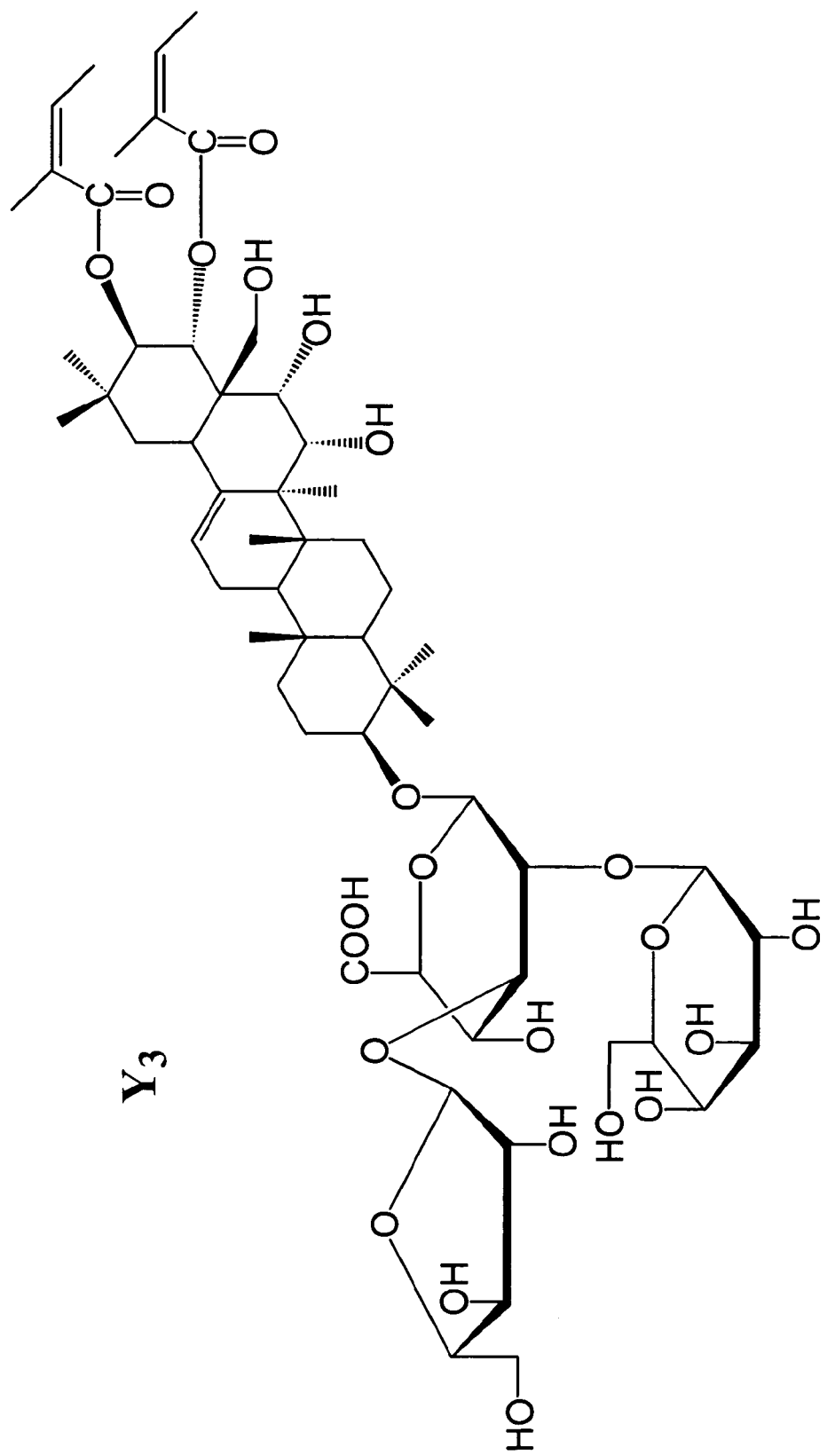
Figure 17. Chemical Structure of compound Y (Y3)

Proton NMR of Y

2D NMR (HMQC) of Y

HMBC of Y

MS (MALDI-TOF) of Y
Y + Matrix (CHCA) + Angiotensin 1 "two point Calibration"

Figure 22 MS-ESI of Y

Figure 23. Chemical Structure of Y1

Proton NMR of Y1

HMQC of Y1

HMBC of Y1

Figure 28. Chemical Structure of Y2

H-NMR Spectrum of Y2

Y2 HMQC-level-1

Y2 C13 H-NMR spectrum

Y2-HMBC-level 1

Y2-HOHAHA-level-1

Figure 34: Mass spectrum of Y2 + Matrix + Standards

Figure 35. Structure of Y8

Y8-H-NMR-full

Y8-HMQC-level-1

Y8-C13 NMR (or HMQC-level 2)

Figure 39. Structure of Y9

Y9-H-NMR

Y9-HMQC-level-1

Y9 2D NMR (HMQC) level 2

Figure 43. Structure of Y10

Y10-H-NMR

Y10-HMQC-level-1

Y10-HMQC-level-2

R1-Structure

R1: 3-O-[angeloyl-(1→3)-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β, 21β, 22α, 28-tetrahydroxyolean-12-ene

R1-H-NMR

R1-HMQC

R1-HMBC-level 1

R1-COSY

R1-C13-1

Structure of Compound O54

O54-H-NMR

O54-HMQC

O54-HMBC

H-NMR of Y4

HMQC of Y4

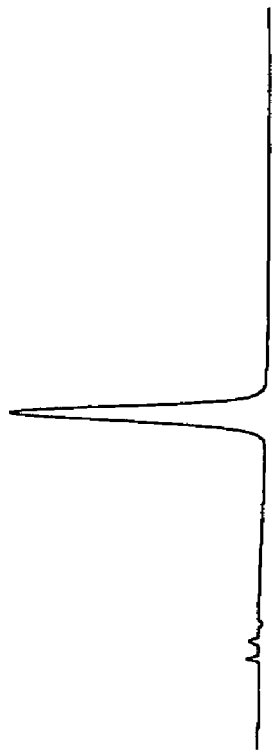
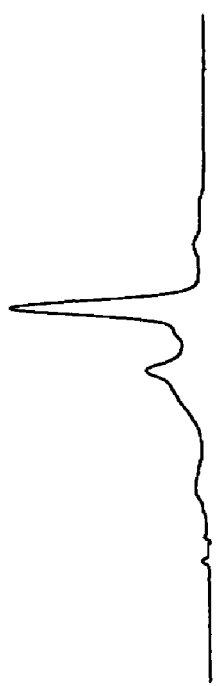
Figure 60

Figure 61 (iso-20)

Re-chromatography of #28 and #34 (from iso-20)

Re-chromatography of #54 (from iso-20)

ANTICANCER BIANGELOYL SAPONINS

This application claims benefit of U.S. Ser. No. 10/906,303, filed Feb. 14, 2005, Continuation-In-Part application of International Application No. PCT/US04/43465, filed Dec. 23, 2004, which is a Continuation-In-Part application of Int'l App'l No. PCT/US04/33359, filed Oct. 8, 2004, which claims benefit of U.S. Ser. Nos. 60/532,101, filed Dec. 23, 2003, and 60/509,851, filed Oct. 9, 2003; and which claims benefit of U.S. Ser. Nos. 60/617,379, filed Oct. 8, 2004, 60/613,811, filed Sep. 27, 2004, and 60/607,858, filed Sep. 7, 2004. The contents of these preceding applications are hereby incorporated in their entireties by reference into this application.

Throughout this application, various publications are referenced. Disclosures of these publications in their entireties are hereby incorporated by reference into this application in order to more fully describe the state of the art to which this invention pertains.

FIELD OF THE INVENTION

This invention relates to extracts from a plant called Wenguanguo or *Xanthoceras sorbifolia*, their uses and functions, and methods of their preparation. This invention further relates to novel compounds obtainable from *Xanthoceras sorbifolia* and plants from the sapindaceae family.

BACKGROUND OF THE INVENTION

Wenguanguo is a species of the sapindaceae family. Its scientific name is *Xanthoceras sorbifolia* Bunge. Wenguanguo is the common Chinese name. Others are Wenguannguo, Wenguanmu, Wenguanhua, Xilacedeng, Goldenhorn and Yellowhorn. Wenguanguo is grown in Liaoning, Jilin, Hebei, Shandong, Jiangsu, Henan, Shanxi, Shaanxi, Gansu, Ningxia and Inner Mongolia, China. Its seeds, leaves and flowers are edible and have been used as a folk or traditional medicine to treat enuresis for centuries. Its branches and woods are also used as a folk or traditional medicine. For more detailed information and background or relevent art of the present invention, please refer to page 1, lines 25-38, to page 13 of International PCT Application No. PCT/US04/33359, filed Oct. 8, 2004, and U.S. Ser. No. 10/906,303, filed Feb. 14, 2005. The contents of these preceding applications are hereby incorporated in their entireties by reference into this application.

Yingjie Chen, Tadahiro Takeda and Yukio Ogihara reported in Chem. Pharm. Bull 33(4)1387-1394(1985) described a study on the constituent of *Xanthoceras sorbifolia* Bunge. See Section V. Saponins from the Fruits of *Xanthoceras sorbifolia*. Four new saponins were isolated from the fruits of *Xanthoceras sorbifolia* Bunge. The structures of these saponins are bunkankasaponins A, B, C and D. The chemical name of these compounds are:

22-O-acetyl-21-O-(4-O-acetyl-3-O-angeloyl)-β-D-fucopyranosyl-3-O-[β-D-glucopyranosyl-(1→2)-β-D-glucuronopyranosyl]protoaecigenin 22-O-acetyl-21-O-(3,4-di-O-angeloyl)-β-D-fucopyranosyl-3-O-[β-D-glucopyranosyl-(1→2)-β-D-glucuronopyranosyl]protoaecigenin 28-O-acetyl-21-O-(4-O-acetyl-3-O-angeloyl)-β-D-fucopyranosyl-3-O-[β-D-glucopyranosyl-(1→2)-β-D-glucuronopyranosyl]protoaecigenin 28-O-acetyl-21-O-(3,4-di-O-angeloyl)-β-D-fucopyranosyl-3-O-[β-D-glucopyranosyl-(1→2)-β-D-glucuronopyranosyl]protoaecigenin.

The functions of these compounds were not previously disclosed.

Yingjie Chen, Tadahiro Takeda and Yukio Ogihara reported in Chem. Pharm. Bull 33(3)1043-1048(1985) described studies on the constituent of *Xanthoceras sorbifolia* Bunge. See Section IV. Structures of the Miner Prosapogenin. The prosapogenins from the partial hydrolyzate of fruit saponin of *Xanthoceras sorbifolia* were examined, and are characterized as:

16-O-acetyl-21-O-(3,4-di-O-angeloyl-β-D-fucopyranosyl)protoaecigenin

22-O-acetyl-21-O-(3,4-di-O-angeloyl-β-D-fucopyranosyl)protoaecigenin 3-O-β-D-glucuronopyranoside.

The functions of these compounds were not previously disclosed.

Yingjie Chen, Tadahiro Takeda and Yukio Ogihara. Chem. Pharm. Bull 33(1)127-134(1985) described studies on the constituent of *Xanthoceras sorbifolia* Bunge. See Section III. Minor Prosapogenins aponins from the Fruits of *Xanthoceras sorbifolia* Bunge. The structure of 3 minor prosapogenins, obtained by acid hydrolysis of the crude saponin faction, were characterized as:

21-O-(3,4-di-O-angeloyl)-β-D-fucopyranosyltheasapogenol B

21-O-(4-O-acetyl-3-O-angeloyl)-β-D-fucopyranosyltheasapogenol B

21-O-(4-O-acetyl-3-O-angeloyl)-β-D-fucopyranosyl-22-O-acetylprotoaescigenin.

The functions of these compounds were not previously disclosed.

Yingjie Chen, Tadahiro Takeda and Yukio Ogihara in Chem. Pharm. Bull 33(4)1387-1394(1985) described a study on the constituent of *Xanthoceras sorbifolia* Bunge. See Section II. Major Sapogenol and prosapogenin from the Fruits of *Xanthoceras sorbifolia*. In addition to above studies, saponins with angeloyl groups attached were also reported in the following reports.

Laurence Voutquenne, Cecile Kokougan. Catherine Lavaud, Isabelle Pouny, Marc Litaudon. "Triterpenoid saponins and Acylated prosapogenins from Harpullia austrocalcdonica." Phytochemistry 59 (2002) 825-832.

Zhong Jaing, Jean-francois Gallard, Marie-Therese Adeline, Vincent Dumontet, Mai Van Tri, Thierry Sevenet, and Mary Pais "Six Triterpennoid Saponins from Maesa laxiflora." J. Nat. Prod. (1999), 62, 873-876.

Young Seo, John M. Berger, Jennine Hoch, Kim M Neddermann, Isia Bursuker, Steven W. Mamber and David G. Kingston. "A new Triterpene Saponin from Pittosporum viridiflorum from the Madagascar Rainforest". J. Nat. Prod. 2002, 65, 65-68.

Xiu-Wei Yang, Jing Zhao, Xue-Hui Lui, Chao-Mei Ma, Masao Hattori, and Li He Zhang "Anti-HIV-1 Protease Triterpenoid Saponins from the Seeds of *Aesculus chinensis*." J. Nat. Prod. (1999), 62, 1510-1513.

Yi Lu, Tatsuya Umeda, Akihito Yagi, Kanzo Sakata, Tirthankar Chaudhuri, D.K. Ganguly, Secion Sarma. "Triterpenoid Saponins from the roots of the tea plant (*Camellia sinensis* var. *Assamica*)." Phytochchemistry 53 (2000) 941-946.

Sandra Apers, Tess E. De Bruyne, Magda Claeys, Arnold J. Viletinck, Luc A.C. Pieters. "New acylated triterpenoid saponins from Maesa laceceolata." Phytochemistry 52 (1999) 1121-1131.

Ilaria D'Acquarica, Maria Cristina, Di Giovanni, Francesco Gasparrini, Domenico Misiti, Claudio D'Arrigo, Nicolina Fagnano, Decimo Guarnieri, Giovanni Iacono, Giuseppe Bifulco and Raffaele Riccio. "Isolation and structure elucidation of four new triterpenoid estersaponins from fruits of the Pittosporumtobira AIT." Tetrahedron 58 (2002) 10127-10136.

Cancer cells are defined by two heritable properties: (1) they reproduce in defiance of normal restraints on cell division; and (2) they invade and colonize territories normally reserved for other cells.

Cancers require mutations of one to many genes for its development, and they are classified according to the tissue and cell type from which they arise. Cancers arising from epithelial cells are named carcinomas; those arising from connective tissue or muscle cells are named sarcomas. In addition, there are cancers called leukemias, which are derived from hemopaietic cells. Cancers can also develop from cells of the nervous system.

Cancers originating from different types of cells are, in general, very different diseases. Each cancer has characteristics that reflect its origin. Even when a cancer has metastasized and proliferated out of control, its origins can be traced back to a single, primary tumor. Therefore, it is important to develop drugs or compounds capable of targeting various types of cancer cells.

Ovarian cancer is the 5th leading cause of cancer death in women and the leading cause of death from gynecologic malignancies. In the United States, females have a 1.4 to 2.5%, or 1 out of 40-60 women, lifelong chance of developing ovarian cancer. Older women are at highest risk. More than half of the deaths from ovarian cancer occur in women between 55 and 74 years of age, and approximately one quarter of ovarian cancer deaths occur in women between 35 and 54 years of age. See MedlinePlus Encyclopedia on ovarian cancer at http://www.nlm.nih.gov/medlineplus/ency/article/000889.htm.

Ovarian cancer is disproportionately deadly for a number of reasons. First, symptoms are vague and non-specific, so women and their physicians frequently attribute them to more common conditions. By the time the cancer is diagnosed, the tumor has often spread beyond the ovaries. Also, ovarian cancers shed malignant cells that frequently implant on the uterus, bladder, bowel, and lining of the bowel wall (omentum). These cells can begin forming new tumor growths before cancer is even suspected. Second, because no cost-effective screening test for ovarian cancer exists, more than 50 percent of women with ovarian cancer are diagnosed in the advanced stages of the disease.

This invention provides compounds or compositions extracted from *Xanthoceras sorbifolia* or plants from the sapindaceae family, or synthesized which have substantial potency against ovarian cancer.

SUMMARY OF THE INVENTION

In accordance with these and other objects of the invention, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

The invention provides six novel compounds of structure (Y1, Y2, Y or Y3, Y8, Y9, Y10) as shown in FIG. 1. As used herein, "Y" is also referred to as "Y3".

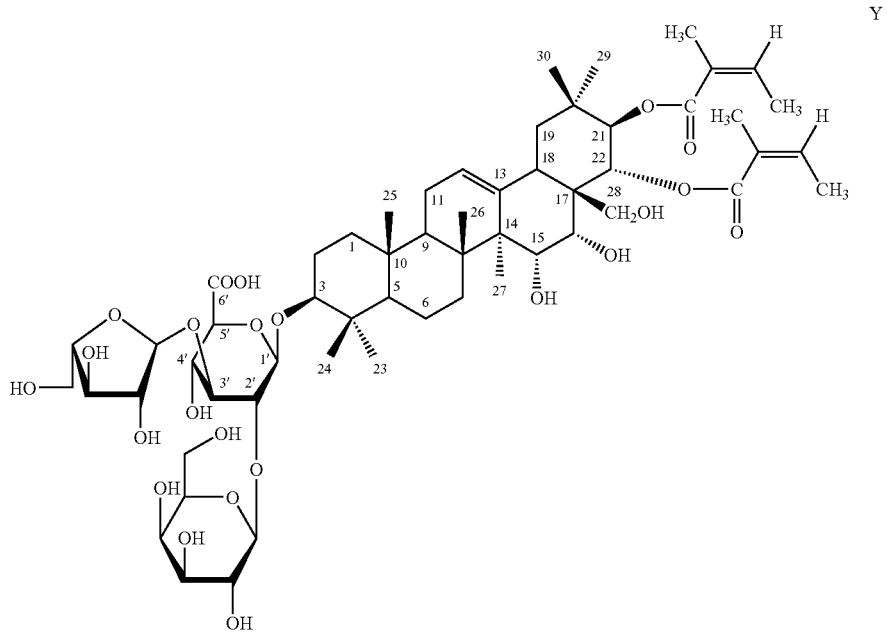

-continued
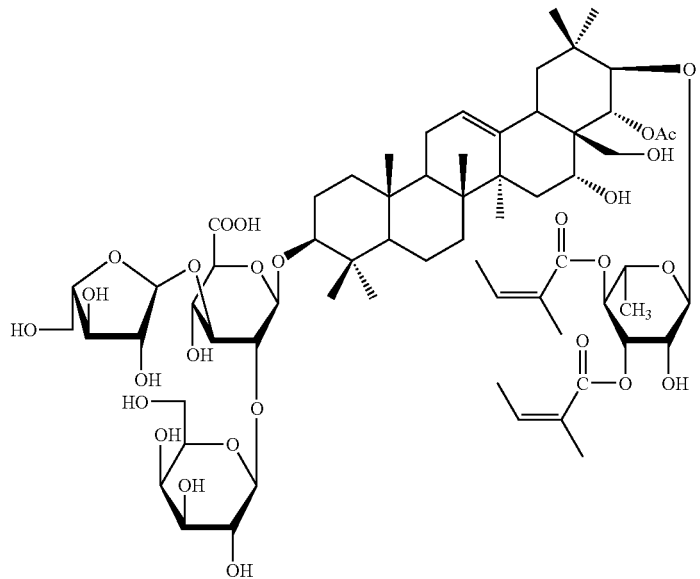
Y₁
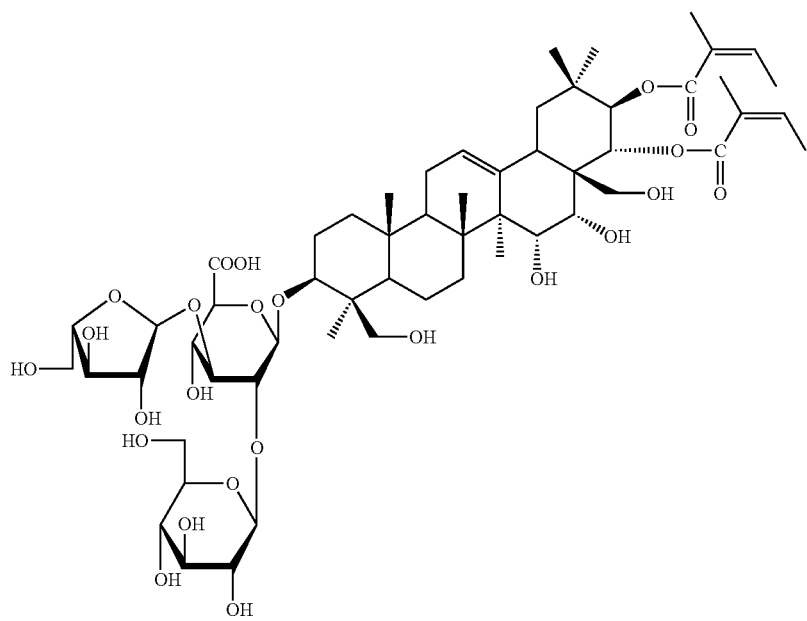
Y₂

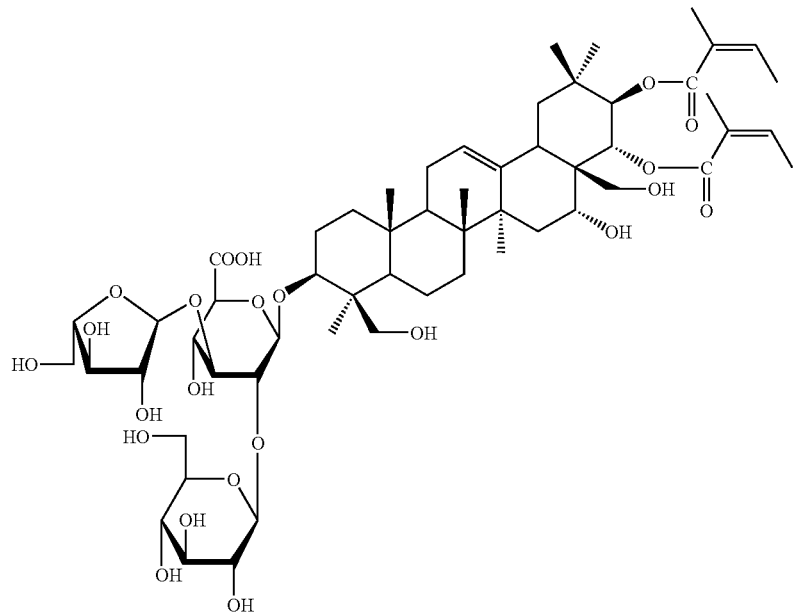
Y-8
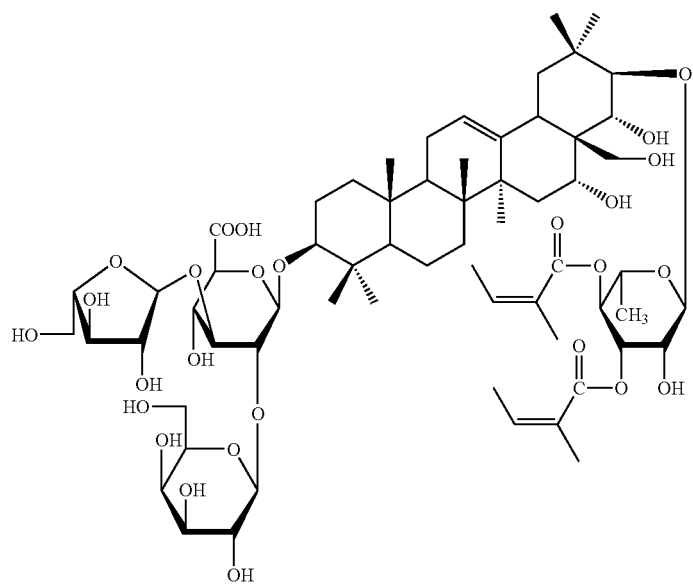
Y-9

-continued

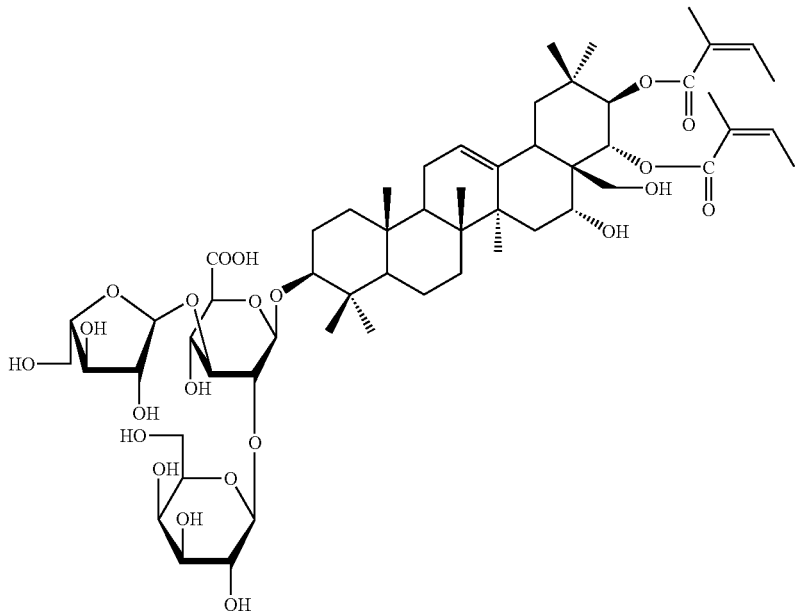

Y-10

The formula, chemical name and common name of these compounds are presented in Table 1 below.

TABLE 1

Formula, Chemical Name and Common Name Six Novel Compounds of structure (Y, Y$_1$, Y$_2$, Y8, Y9, Y10)

| Names | Formula | Chemical Name |
|---|---|---|
| Y (Y3) | C$_{57}$H$_{88}$O$_{23}$ | 3-O-[β-D-galactopyranosyl(1→2)]-α-L-arabinofuranosyl(1→3)-β-D-glucuronopyranosyl-21,22-O-diangeloyl-3β,15α,16α,21β,22α,28-hexahydroxyolean-12-ene, |
| Y1 | C$_{65}$H$_{100}$O$_{27}$ | 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β,16α,21β,22α,28-pentahydroxyolean-12-ene |
| Y2 | C$_{57}$H$_{88}$O$_{24}$ | 3-O-[β-D-glucopyranosyl-(1→2)]-α-L-arabinofuranosyl(1→3)-(-D-glucuronopyranosyl-21,22-O-diangeloyl-3(,15(16(,21(,22(,24(,28-heptahydroxyolean-12-ene |
| Y8 | C$_{57}$H$_{87}$O$_{23}$ | 3-O-[β-galactopyranosyl(1→2)]-α-arabinofuranosyl(1→3)-β-glucuronopyranosyl-21,22-O-diangeloyl-3β,16α,21β,22α,28-pentahydroxyolean-12-ene |
| Y9 | C$_{63}$H$_{98}$O$_{26}$ | 3-O-[β-galactopyranosyl(1→2)]-α-arabinofuranosyl(1→3)-β-glucuronopyranosyl-21-O-(3,4-diangeloyl)-α-rhamnopyranosyl-3β,16α,21β,22α,28-pentahydroxyolean-12-ene |
| Y10 | C$_{57}$H$_{87}$O$_{22}$ | 3-O-[β-galactopyranosyl(1→2)]-α-arabinofuranosyl(1→3)-β-glucuronopyranosyl-21,22-O-diangeloyl-3β,16α,21β,22α,28-pentahydroxyolean-12-ene |

The above six compounds (Y, Y1, Y2, Y8, Y9 and Y10) have anti-cancer effect. These compouns inhibit the growth of human ovarian and other cancer cells. See FIGS. 2, 3 and 4.

A concensus sub-structure is identified from these active compounds (Y, Y1, Y2, Y8, Y9 and Y10). The concensus sub-structure of these compounds is the biangeloyl groups located on adjacent carbons.

For Y, Y2, Y8 and Y10, the biangeloyl are located at 21β and 22α of the triterpene backbone. See FIG. 5.

For Y1 and Y9, the biangeloyl are located at C3 and C4 of the sugar ring. See FIG. 6. Accordingly, the biangeloyl groups of these active compounds (Y, Y1, Y2, Y8, Y9 and Y10) are situated in trans-position in respect to each other on a planar structure. See FIG. 7.

Studies of the structure and function relationship of these six structures indicate that changes of the functional groups at C15 and C24 of the triterpene do not affect anticancer activity.

These compounds (Y, Y1, Y2, Y8, Y9 and Y10) are active for inhibition of tumor growth. See FIGS. 2, 3 and 4. These compounds are purified by methods of chromatograpy involving FPLC and HPLC as described in FIGS. 8, 9, 10, 11, 12 and 13.

The compound Y is purified, as shown in FIG. 11A, with procedure described in this application. The purified compound Y shows potence (IC50=1.5 ug/ml) 10 times higher than the original extract (IC50=25 ug/ml) by comparing FIG. 2 with FIG. 14. Compound Y has a high selectivity toward ovarian cancer. See FIG. 15.

The purified compound Y1, Y2, Y8, Y9, and Y10 also show inhibitory activity toward human cancer cells with a higher potency toward ovarian carcinoma. See FIGS. 3 and 4.

The plant extract containing compound Ys shows inhibitory activity toward the following human cancer cells, i.e., eleven human cancer cell lines were tested in this study, with a higher potency toward ovarian carcinoma. See comparison of activities among these cells in FIGS. 14, 15 and 16 and Table 3.1. As used herein, Ys or compound Ys is used to denote compound Y or Y3, Y1, Y2, Y8, Y9, Y10 or other compounds obtainable from *Xanthoceras sorbifolia* extract.

This invention provides an extract of *Xanthoceras sorbifolia* capable of inhibiting cancer growth. The cancer includes, but is not limited to ovary cancer, bladder cancer, prostate cancer, leukocytes cancer, and bone cancer.

The compounds can be isolated from the plant called *Xanthoceras sorbifolia* or can be synthesized chemically, or extracted from other biological sources.

This invention provides a process of producing active compounds from husks, leaves, branches or stems, and fruit-stems, roots and barks of the Wenguanguo and can be employed separately or be combined. This invention further discloses methods of their preparations.

In addition to saponin, the extracts contain saccharides, proteins, glycosides, flavonoids, curmarin extracts, alkaloid extracts, organic acid extracts, tannin and others. In this application saponins were investigated and have been shown to possess inhibitory activity against cancer growth.

The compounds or compositions of the present invention may regulate many cellular pathways including the receptors or components of a cell such as G-protein receptor, Fas protein, receptor Tyrosine Kinases, Mitogen, mitogen receptor. The compounds can be isolated from the plant called *Xanthoceras sorbifolia* or can be synthesized chemically, or extracted from other biological sources.

This invention provides compounds, including compound of structures Y, Y1, Y2, Y8, Y9 and Y10, obtainable from *Xanthoceras sorbifolia* and capable of inhibiting cancer growth. In an embodiment, the cancer includes, but is not limited to bladder cancer, cervix cancer, prostate cancer, lung cancer, breast cancer, leukocytes cancer, colon cancer, liver cancer, bone cancer, brain cancer, and ovary cancer.

This invention provides a compound of oleanene triterpenoidal saponin comprising a side chain at Carbon 21 and Carbon 22 of said compound, wherein the side chain comprises angeloyl groups. In an embodiment, the compound comprises one or more sugars, wherein C3 and C4 of the sugar are acylated with angeloyl groups.

This invention provides a triterpinoidal saponin compound comprising a triterpene backbone and biangeloyl groups, wherein the biangeloyl groups are attached to $21\beta$ and $22\alpha$ of the triterpene backbone, wherein the presence of the biangeloyl group produces anticancer activity.

This invention provides a triterpenoidal saponin compound comprising a triterpene backbone and a sugar moiety or sugar chain, wherein the sugar moiety or sugar chain is attached to the triterpene backbone, wherein the sugar moiety or sugar chain further comprises a biangeloyl group, and wherein the presence of the biangeloyl group produces anticancer activity.

This invention provides a triterpenoidal saponin compound comprising a triterpene backbone, said triterpene backbone is acylated at either $21\beta$ or $22\alpha$ position or at both $21\beta$ and $22\alpha$ position with a sugar moiety or sugar chain, wherein at least one sugar in the sugar moiety or sugar chain comprises angeloyl groups attached to the C3 and C4 position of said sugar.

As used herein, moiety means one of two or more parts into which something may be divided, such as the various parts of a molecule.

In an embodiment, the biangeloyl groups are in the trans-position on a planar structure, and the presence of the biangeloyl group produces anticancer activity.

This invention provides a salt of the above-described compounds.

This invention provides a pharmaceutical composition comprising an effective amount of the above-described compounds and a pharmaceutically acceptable carrier(s).

This invention provides a method for isolating compounds from *Xanthoceras sorbifolia* comprising the steps of: extracting *Xanthoceras sorbifolia* powder with an appropriate amount of an organic solvent for an appropriate amount of time to obtain an extract, identifying the bioactive components in the extract; purifying the bioactive components in the extract with FPLC to obtain a fraction of the bioactive component; and isolating the pure bioactive component with preparative HPLC.

This invention provides a compound having a structure verified by NMR spectral data derived from proton NMR, carbon NMR, 2D NMR of the Heteronuclear Multiple Quantum Correlation (HMQC), Heteronuclear Multiple Bond Correlation (HMBC), NOESY and COSY, and Mass spectral data derived from MALDI-TOF and ESI-MS.

This invention provides the chemical features of a compound and its derivatives which are effective against cancer. Due to complexity of nature, the compounds or compositions of the present invention regulate various cellular pathways including but not limiting the followings: the receptors or components such as G-protein receptor, Fas protein, receptor for Tyrosine Kinases, mitogens, or mitogen receptors. TGF Beta-smad, FGF, TGF-beta and TGF-alpha, ras-GTPase-MAP kinase, jun-fos, Src-fyn, Jak-Jnk-STAT, BMP, Wnt, myc-cell proliferation, etc. The *Xanthoceras Sorbifolia* derived compound and/or composition may regulate the components and receptors and re-activates the cell death program.

DETAILED DESCRIPTION OF THE FIGURES

FIG. 1 shows the structures of six active anticancer saponins isolated from *Xanthoceras Sorbifolia* extract.

FIG. 2 shows the anticancer activity of purified Compound Y. The experiment was performed on ovarian cancer cells (OCAR-3) and the inhibition activity was determined by MTT assay. For details, refer to Experiment 3. Abscissa: Concentration (ug/ml). Ordinate: % Cell Growth. The IC50 is approximately 1-1.5 ug/ml. A: Point scale. B: Linear scale.

FIG. 5 shows the consensus structure derived from four active anticancer saponins (Y, Y2, Y8 and Y10).

FIG. 6 shows the consensus structure derived from two active anticancer saponins (Y1 and Y9).

FIG. 7 shows a general structural formula derived from the consensus structures of the six active compounds (Y, Y1, Y2, Y8, Y9 and Y10). (A) A consensus active functional group is the biangeloyl group attached to $21\beta$ and $22\alpha$ of the triterpene backbone. (B) A consensus active functional group is the biangeloyl group attached at C3 and C4 of a sugar ring (or rhamnose). In both cases, the functional active structure is a biangeloyl group situated in trans-position on a planar structure.

FIG. 8 shows the separation of the components of *Xanthoceras sorbifolia* extract by HPLC with a μbondapak C18 column. Details of experiment were presented in Experiment 2.

Figure 9:
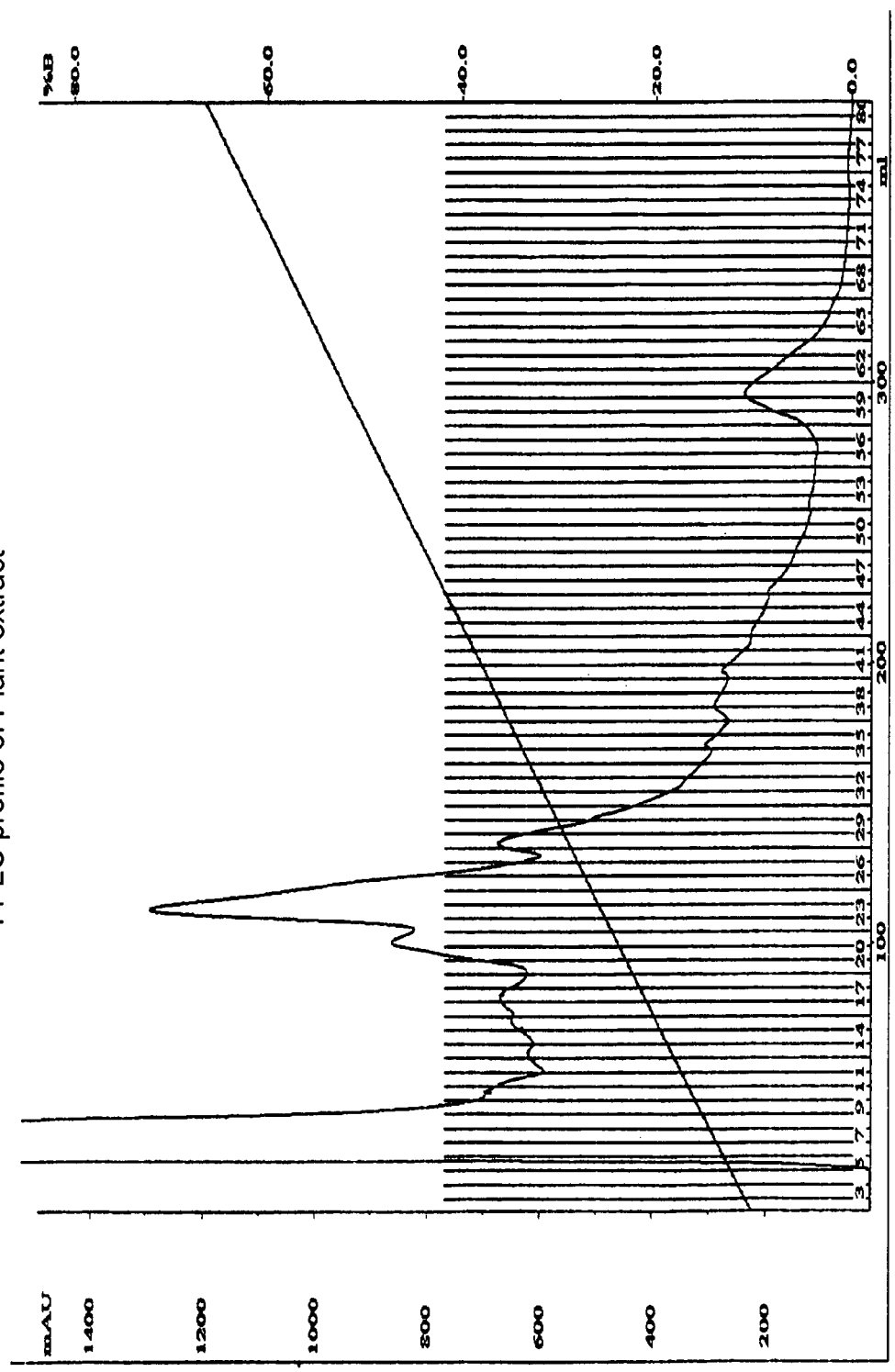

FIG. 9 shows the elution profile of an extract of *Xanthoceras sorbifolia* in FPLC with 10-80% gradient. Ordinate: Optical density (at 245 nm). Abscissa: Fractions (5 ml/fraction).

Figure 10:
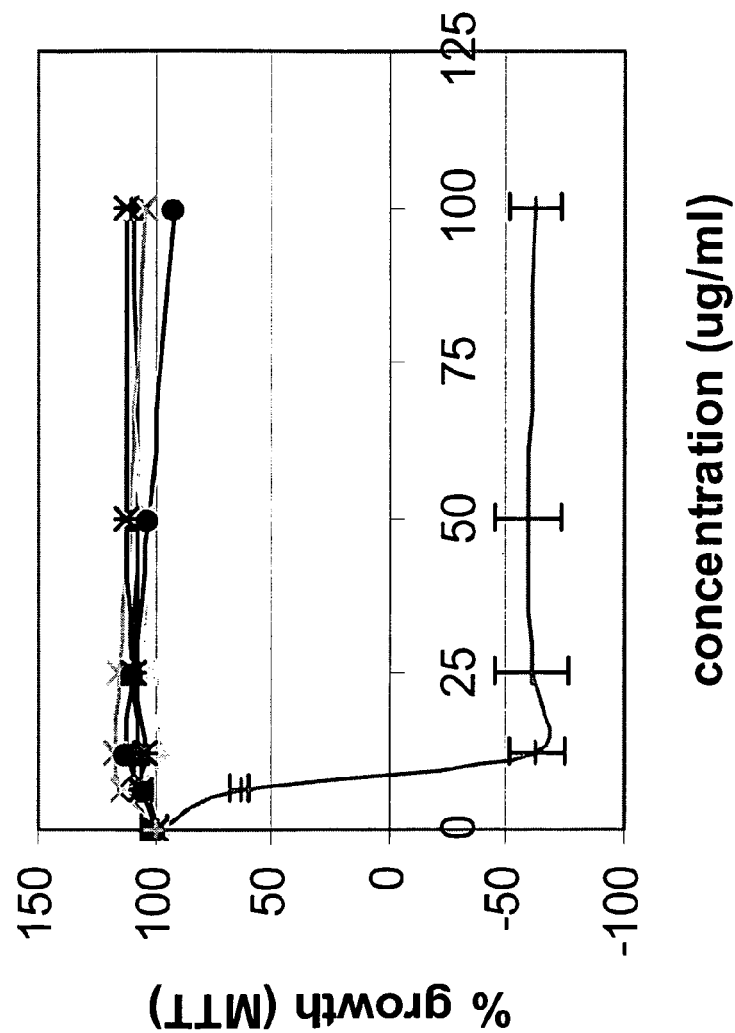

FIG. 10 shows the results of the screening of cell growth activity of fractions obtained from FPLC chromatography. The assay was conducted in bladder cells. The fractions obtained from FPLC as shown in FIG. 9 were used. As shown in this figure, different components of *Xanthoceras sorbifolia* extracts cause either growth or inhibition effects on cells. Only fraction 5962 (Fraction Y) causes cell inhibition. Fractions 610, 1116 and 1724 cause minor stimulation of cell growth. Abscissa: concentration (ug/ml). Ordinate: % Cell Growth (determined by MTT assay).

Figure 11:
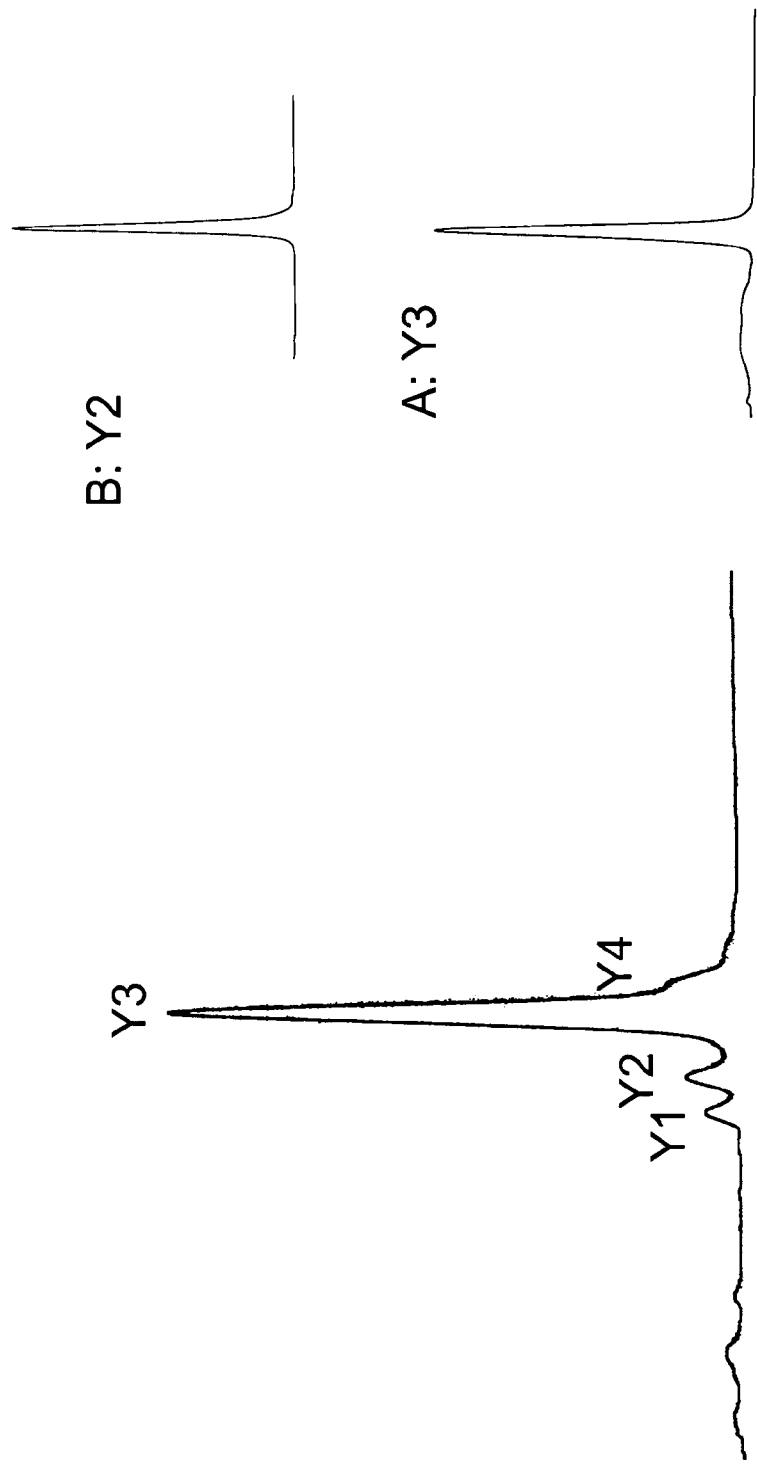

FIG. 11 shows HPLC profile of Fraction Y with 45% acetonitrile isocratic elution in a preparative C18 column (Delta Pak C18). Under these conditions, fractions Y (Y3), Y1 and Y2 are well separated from each other and they are subsequently purified. A and B shows the purity of the collected Y3 and Y2 by HPLC under same conditions.

Figure 12:
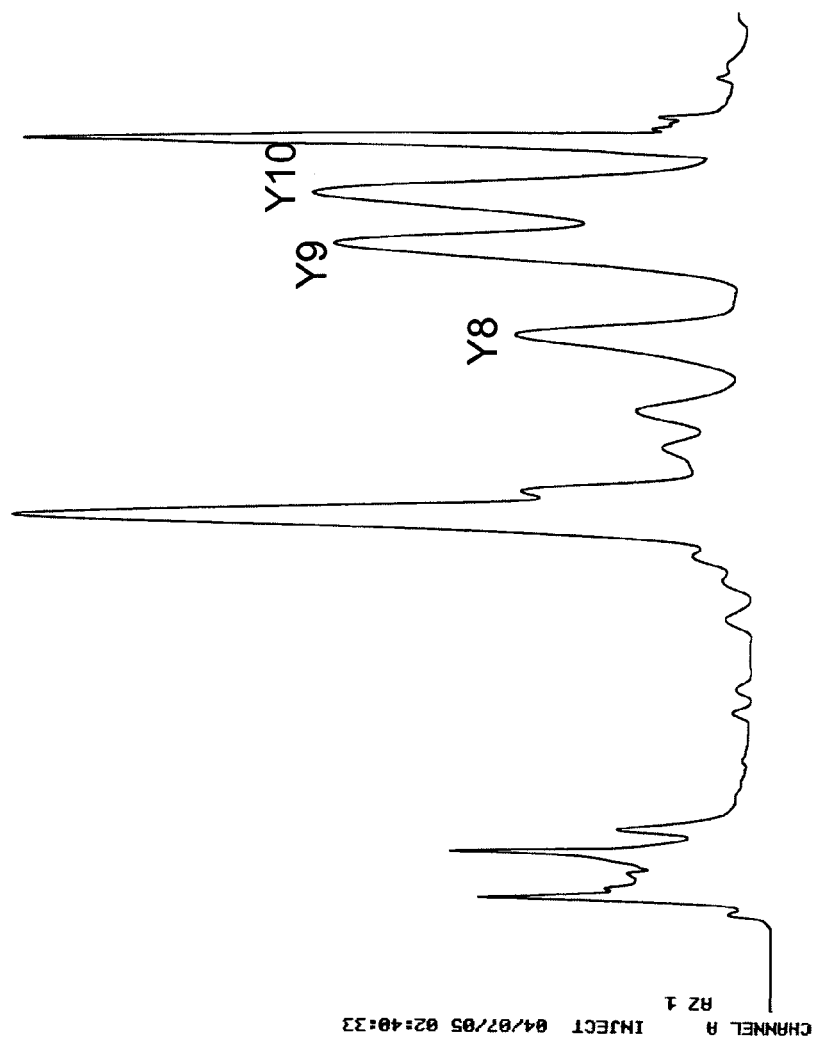

FIG. 12 shows the separation profile of Y8-Y10 with 45% acetonitrile isocratic elution in a preparative C18 column (Delta Pak C18).

Figure 13:
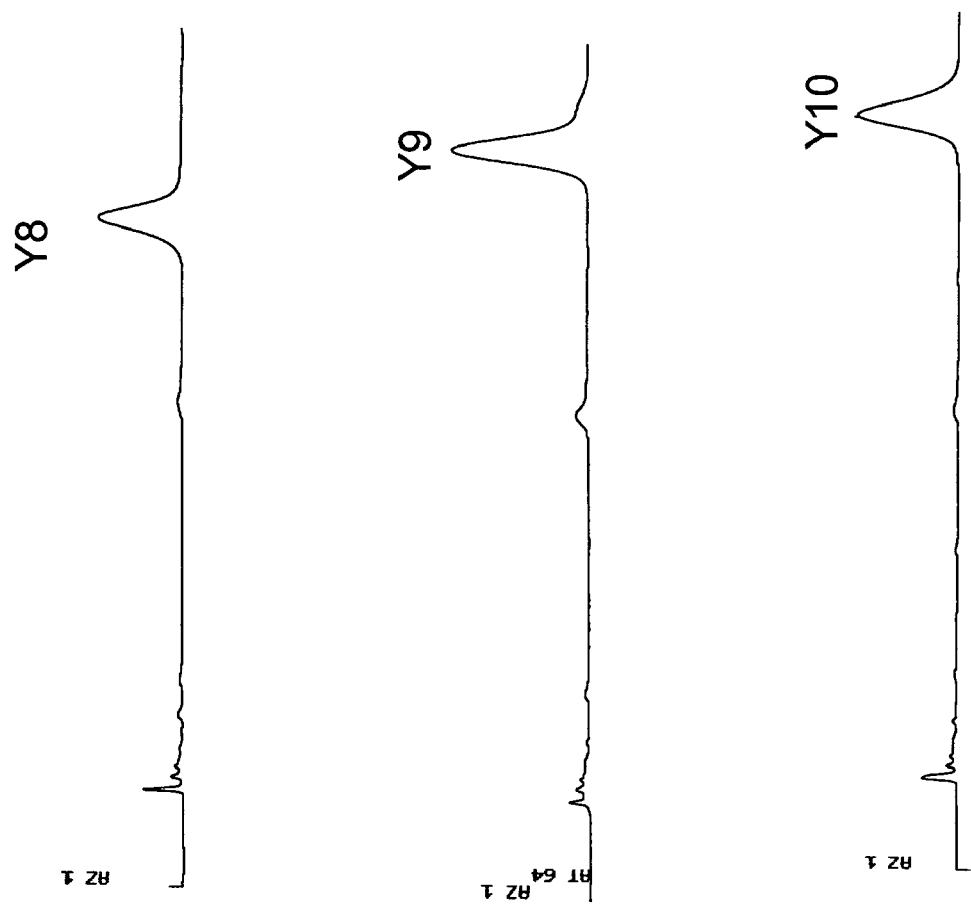

FIG. 13 shows the HPLC profiles of purified Y8, Y9 and Y10.

Figure 14:
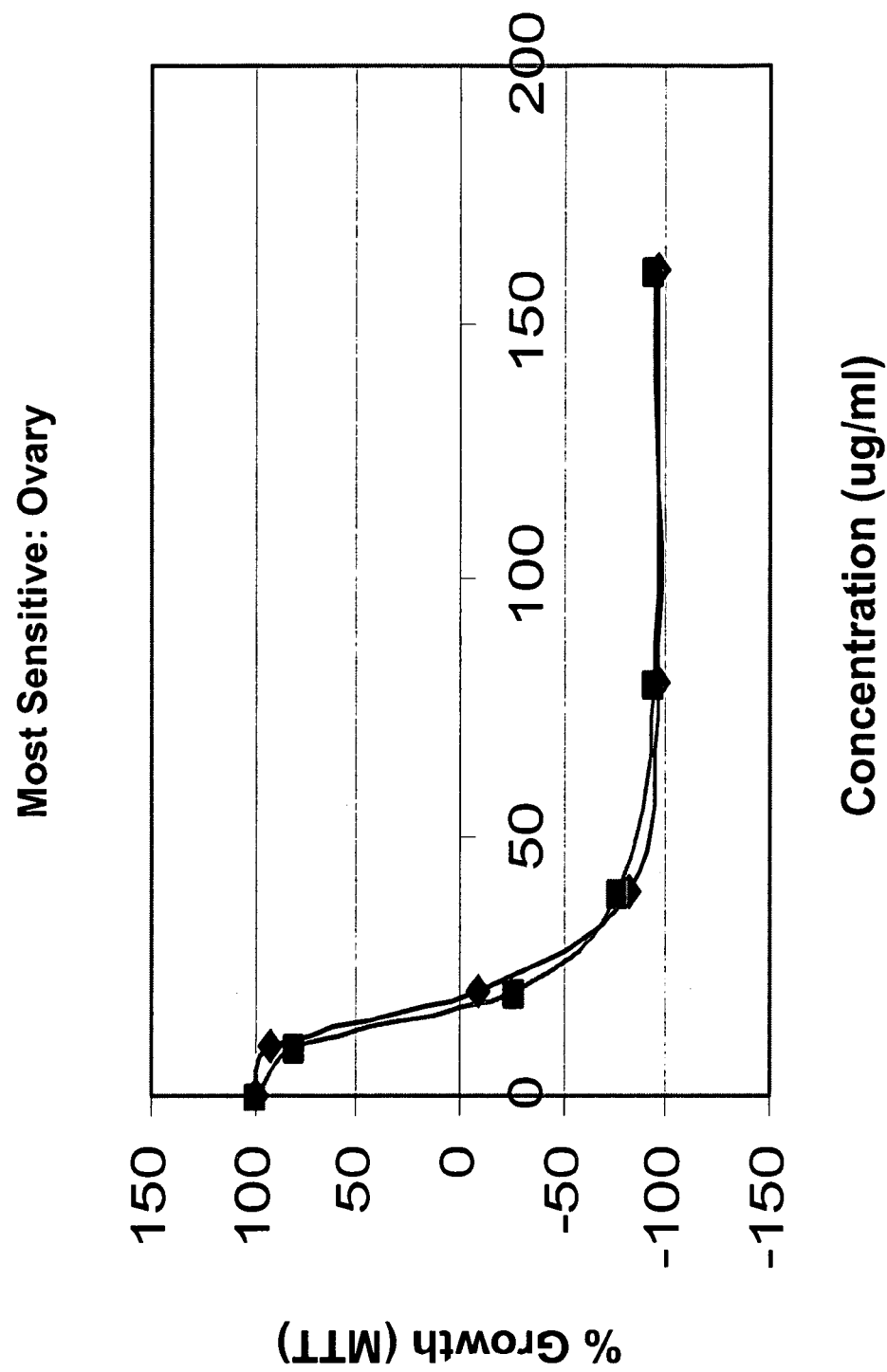

FIG. 14 shows the growth curves of ovarian cancer cells after treatment with the crude extract of *Xanthoceras sorbifolia* as determined by the MTT assay. This study determined the sensitivity of the extract of *Xanthoceras sorbifolia* on cancer cells. In these experiments, cancer cell lines from 11 different human organs were employed. This figure shows that ovary cancer cells are the most sensitive cancer cells in responding to *Xanthoceras Sorbifolia*. Results of other cancer cells were represented in FIGS. 16A-D. Abscissa: concentration (ug/ml). Ordinate: % Cell Growth (determined by MTT assay).

Figure 15:
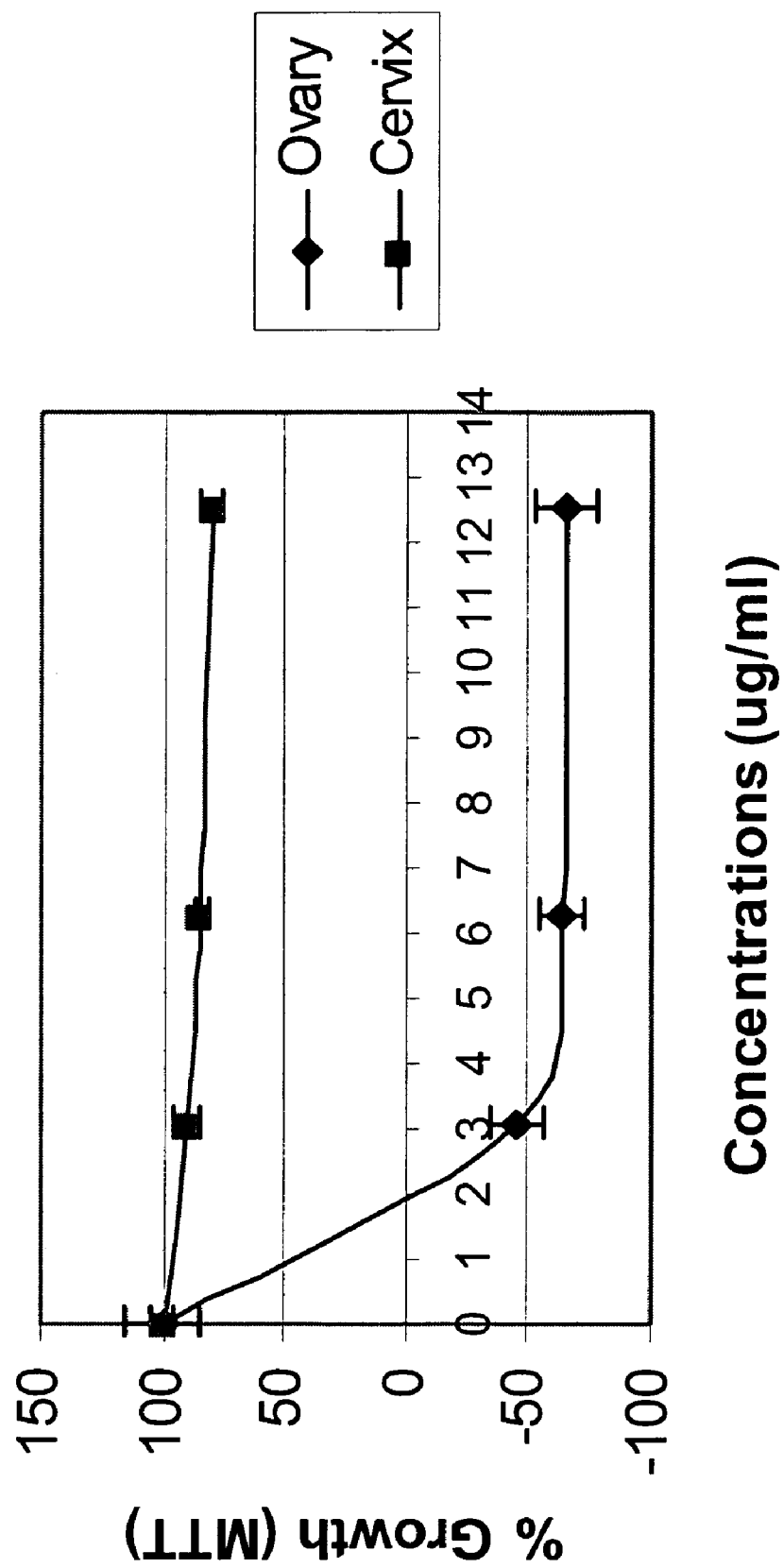
Figure 16A:
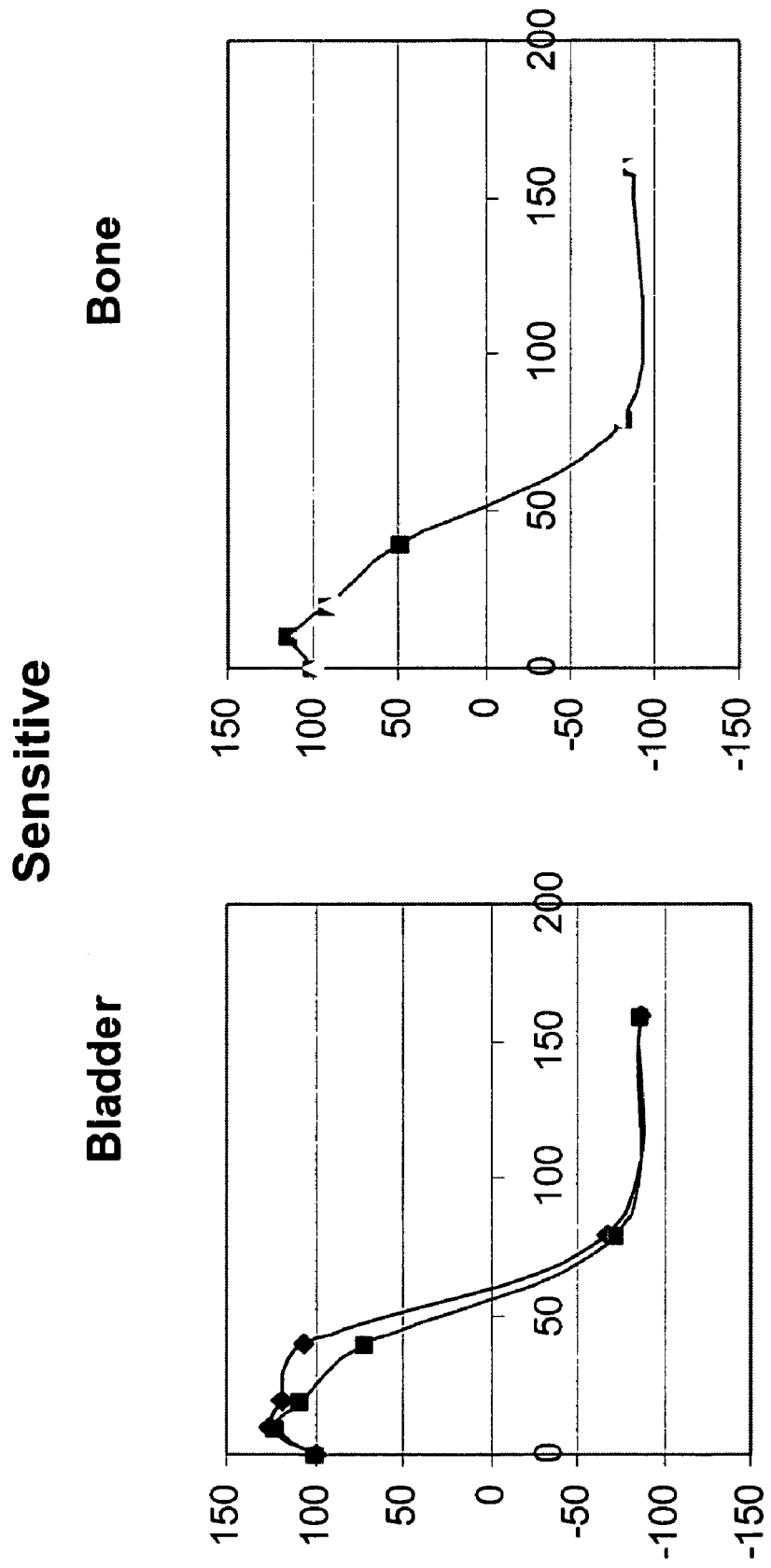
Figure 16B:
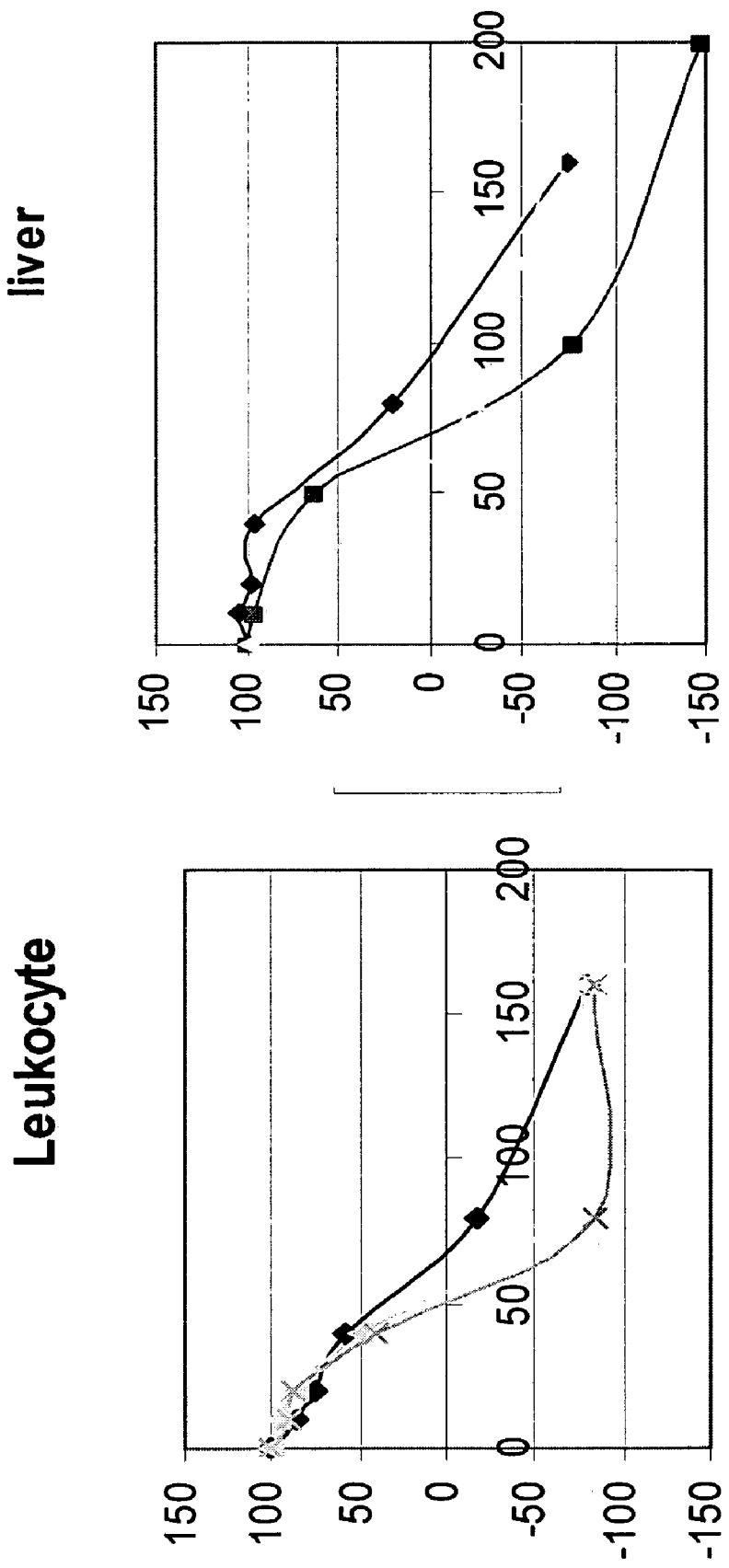
Figure 16C:
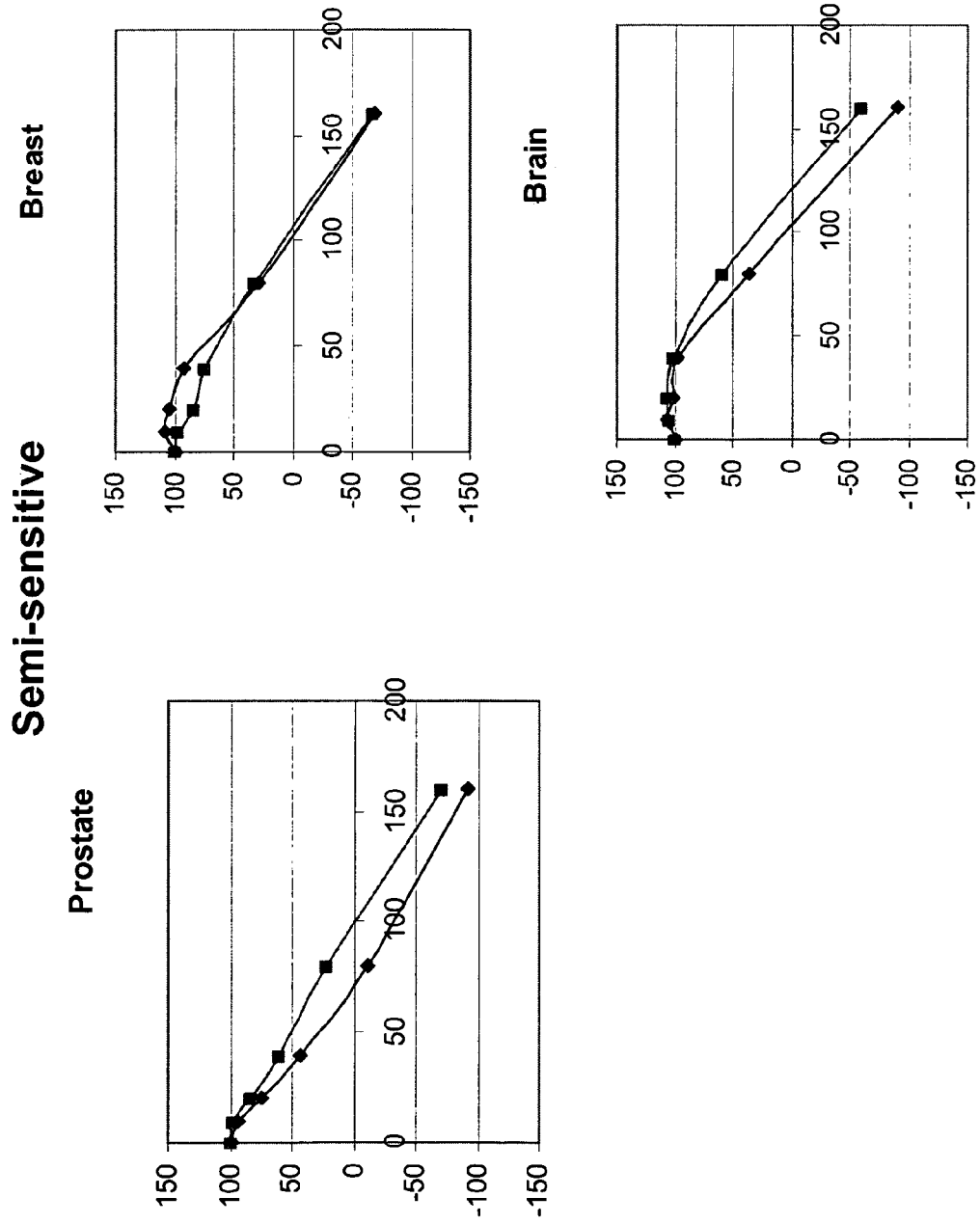
Figure 16D:
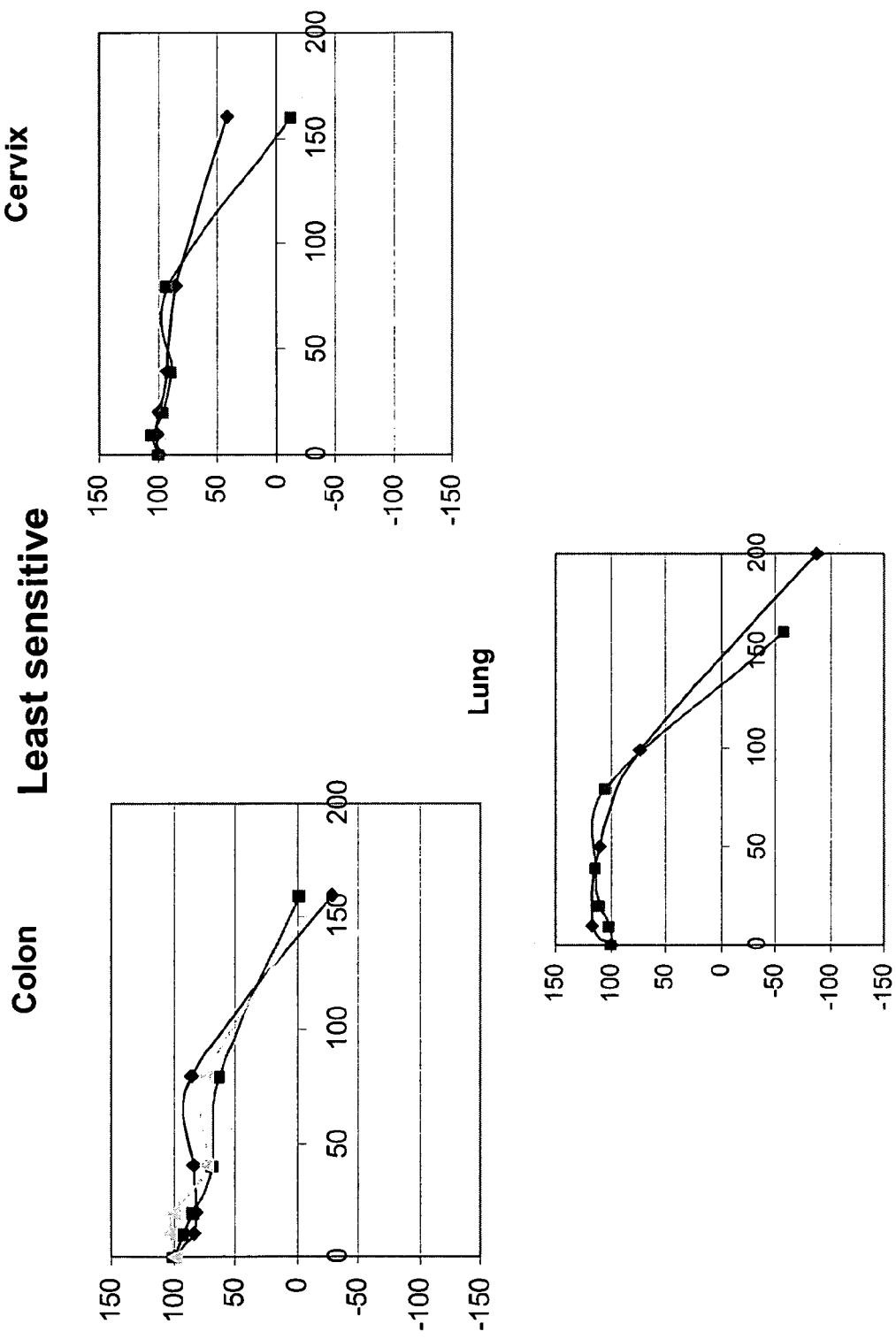

FIG. 15 shows the comparison of potency of Compound Y between ovarian cancer cells and cervical cancer cells. Ovarian cancer cells are much more sensitive than the cervical cancer cells. The IC50 for Compound Y in ovary cells is about 1.5 ug/ml while the IC50 in cervical cancer cells is over 20 ug/ml. See also FIG. 16D. This result confirms that the activity of Compound Y is selective toward ovary cancer.

FIGS. 16A-D show the growth curves of cancer cells derived from different human organs as determined by MTT assay. After treatment with the extract of *Xanthoceras Sorbifolia*, growth curves of different cell lines were presented and their sensitivities (IC50 values) were determined. Sensitivity of cells toward extract can be divided into 4 groups. (1) Most sensitive: ovary cells (presented in FIGS. 14 and 15). (2): Sensitive: bladder and bone (presented in A). (3) Semi-sensitive: leukocyte and liver (presented in B); prostate, breast and brain (presented in C). (4) Least sensitive: colon, cervix and lung (presented in D). Abscissa: concentration (ug/ml). Ordinate: % Cell Growth (determined by MTT assay).

FIG. 17 shows the structure Compound Y with the formula of $C_{57}H_{88}O_{23}$ and the chemical name of 3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene.

Figure 18:
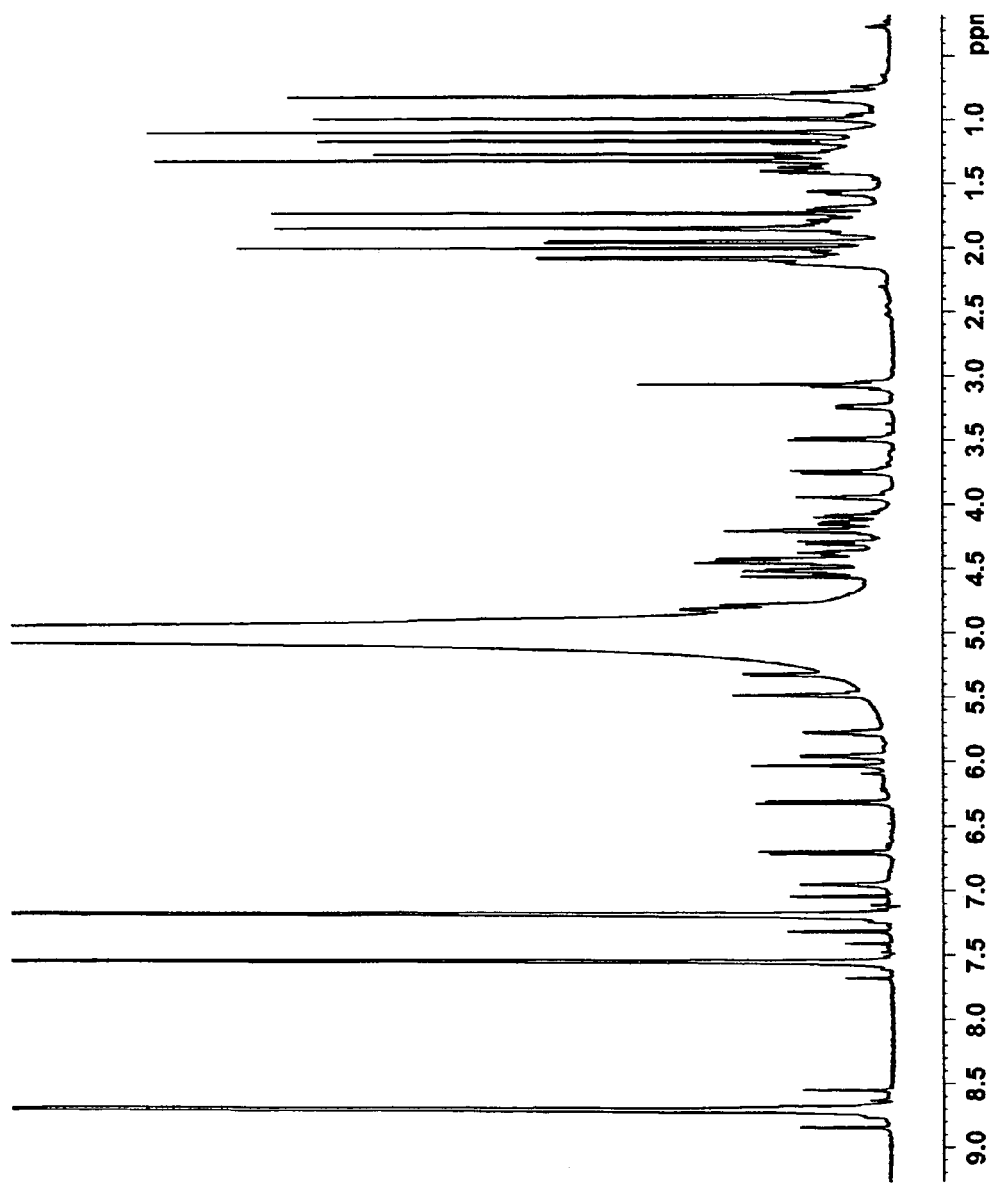

FIG. 18 shows the sprectrum of proton NMR of Compound Y.

Figure 19:
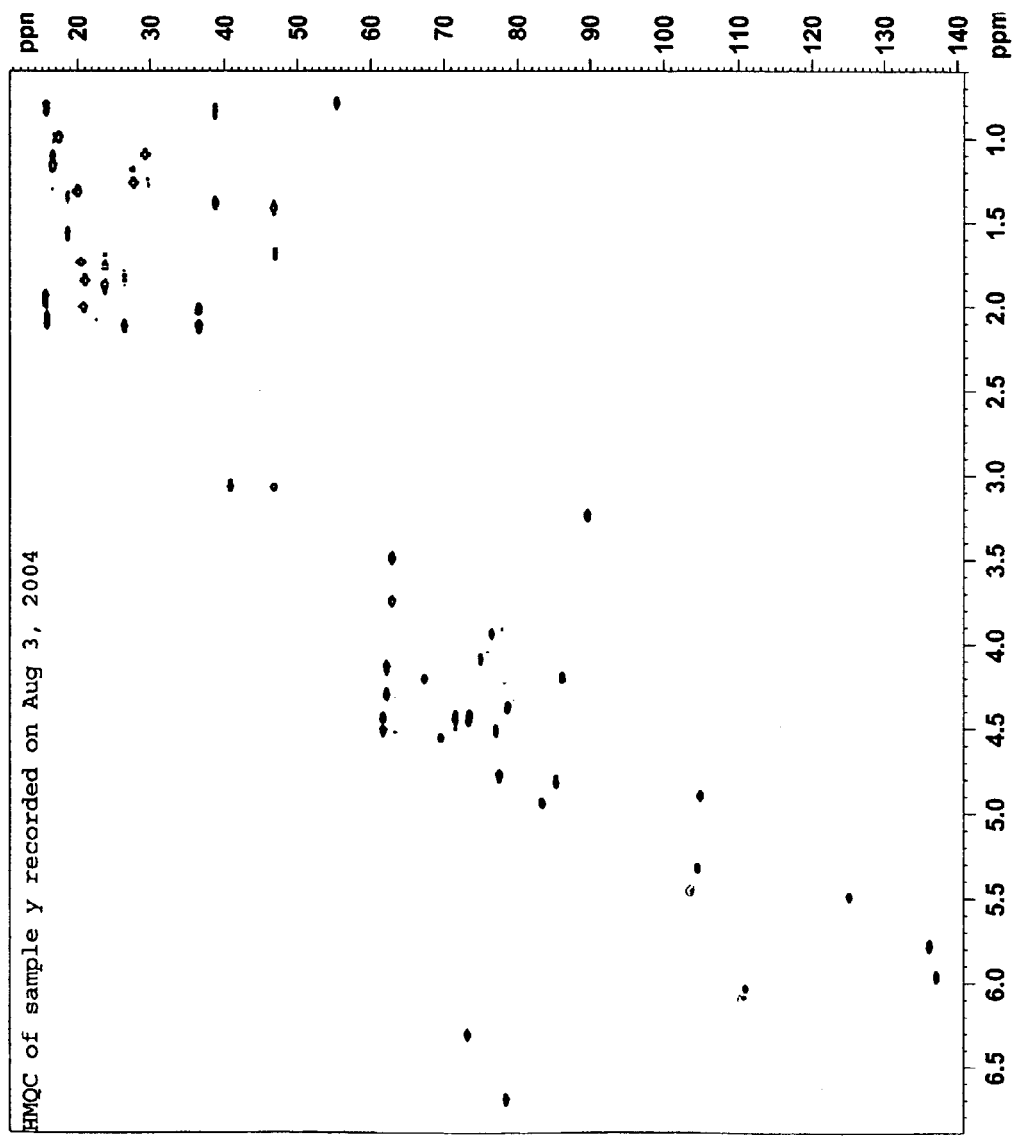

FIG. 19 shows 2D NMR (HMQC) results of Compound Y.

Figure 20:
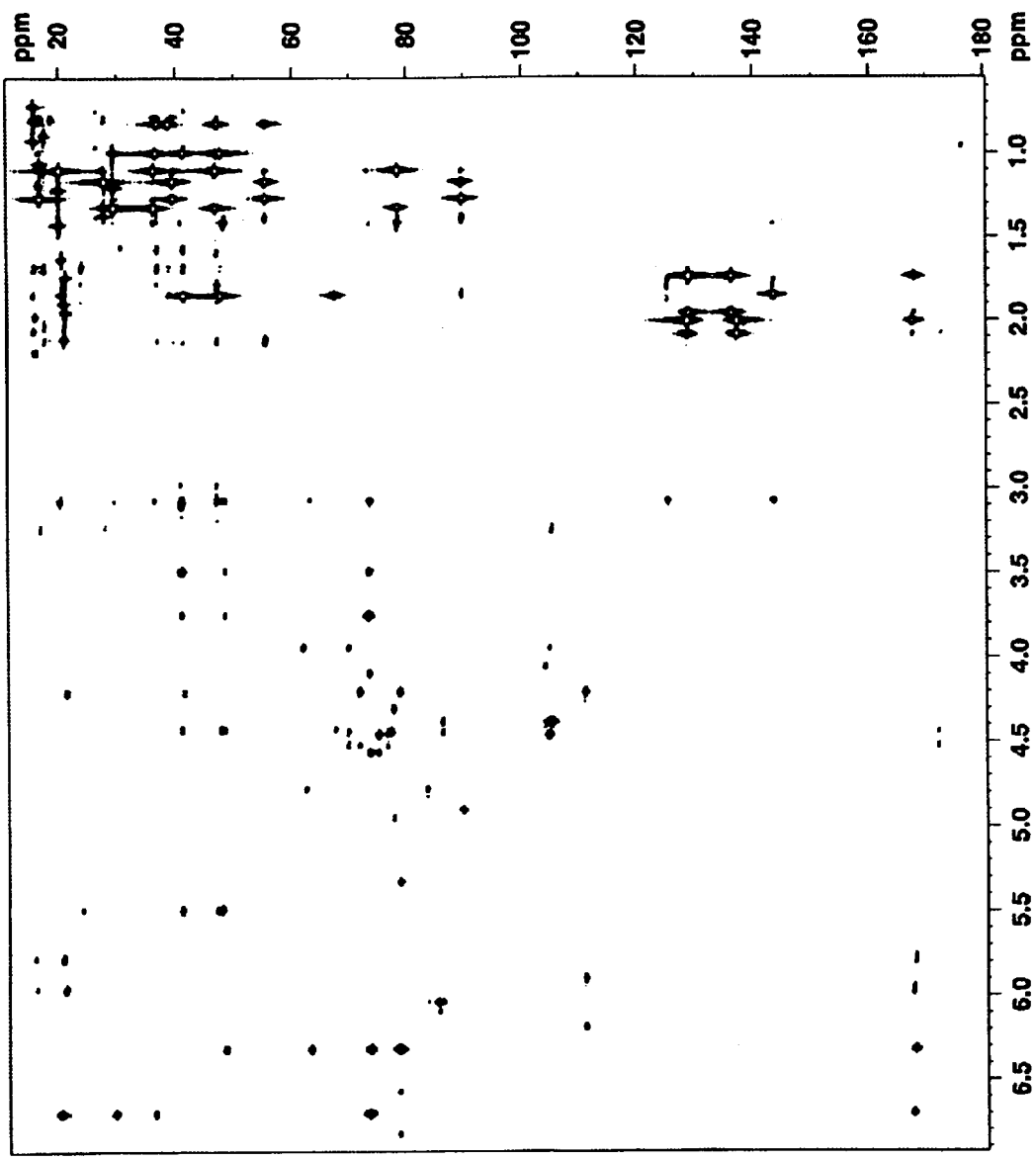

FIG. 20 shows 2D NMR (HMBC) results of Compound Y.

Figure 21:
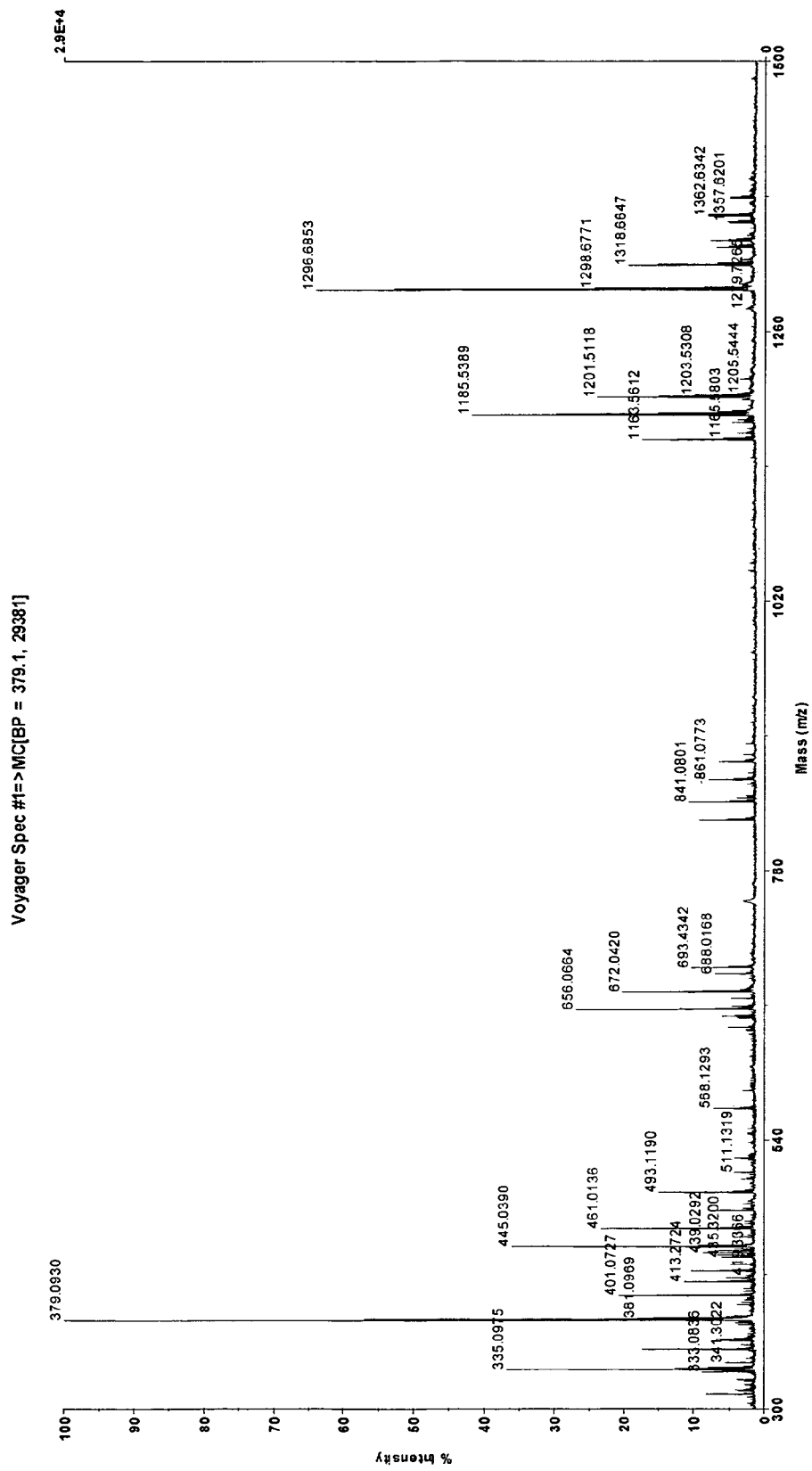

FIG. 21 shows the Mass spectrum of compound Y with MALDI-TOF (high mass): Y+Matrix (CHCA)+Angiotensin 1 "two point calibration".

Figure 22:
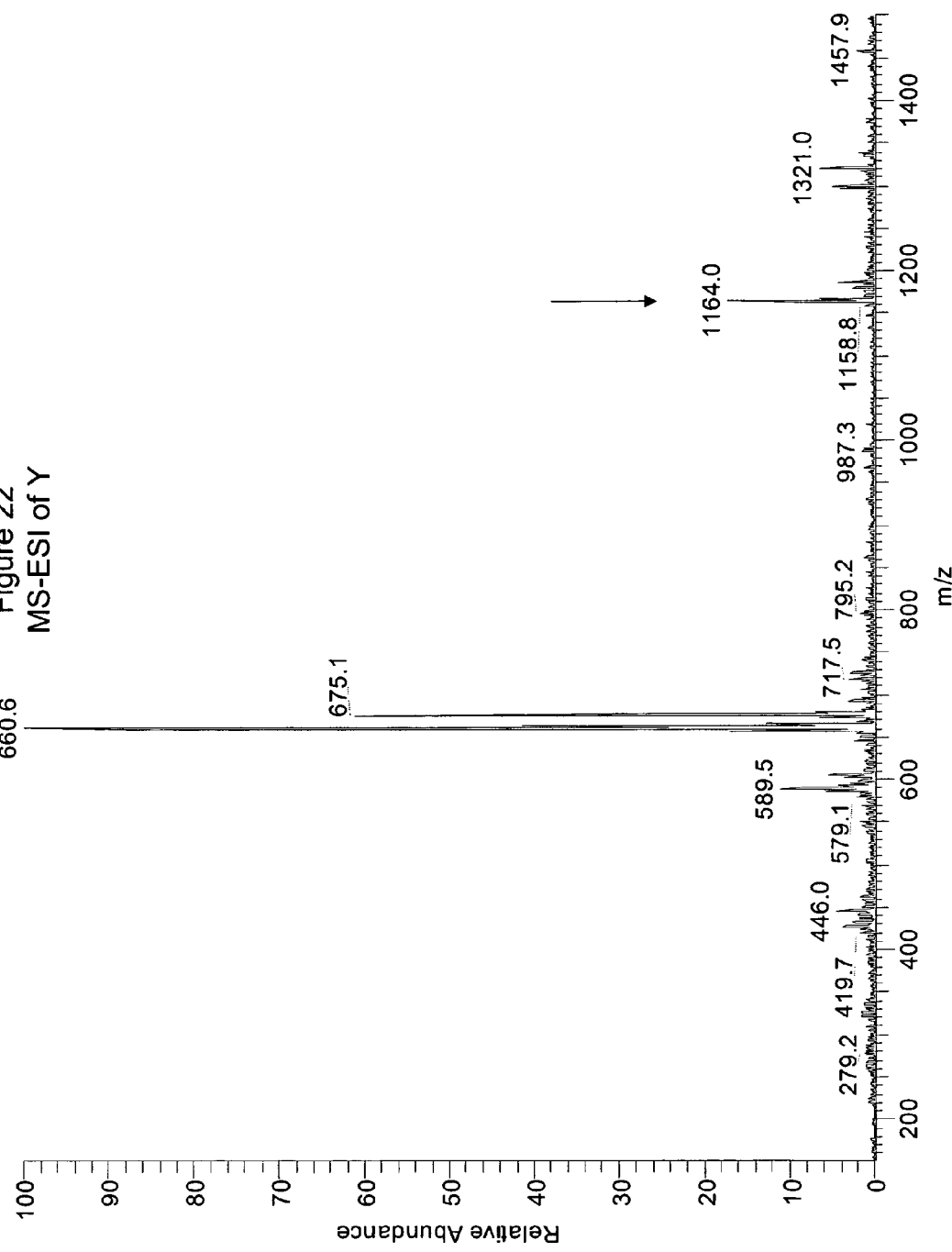

FIG. 22 shows the Mass spectrum of compound Y with ESI-MS.

Figure 23:
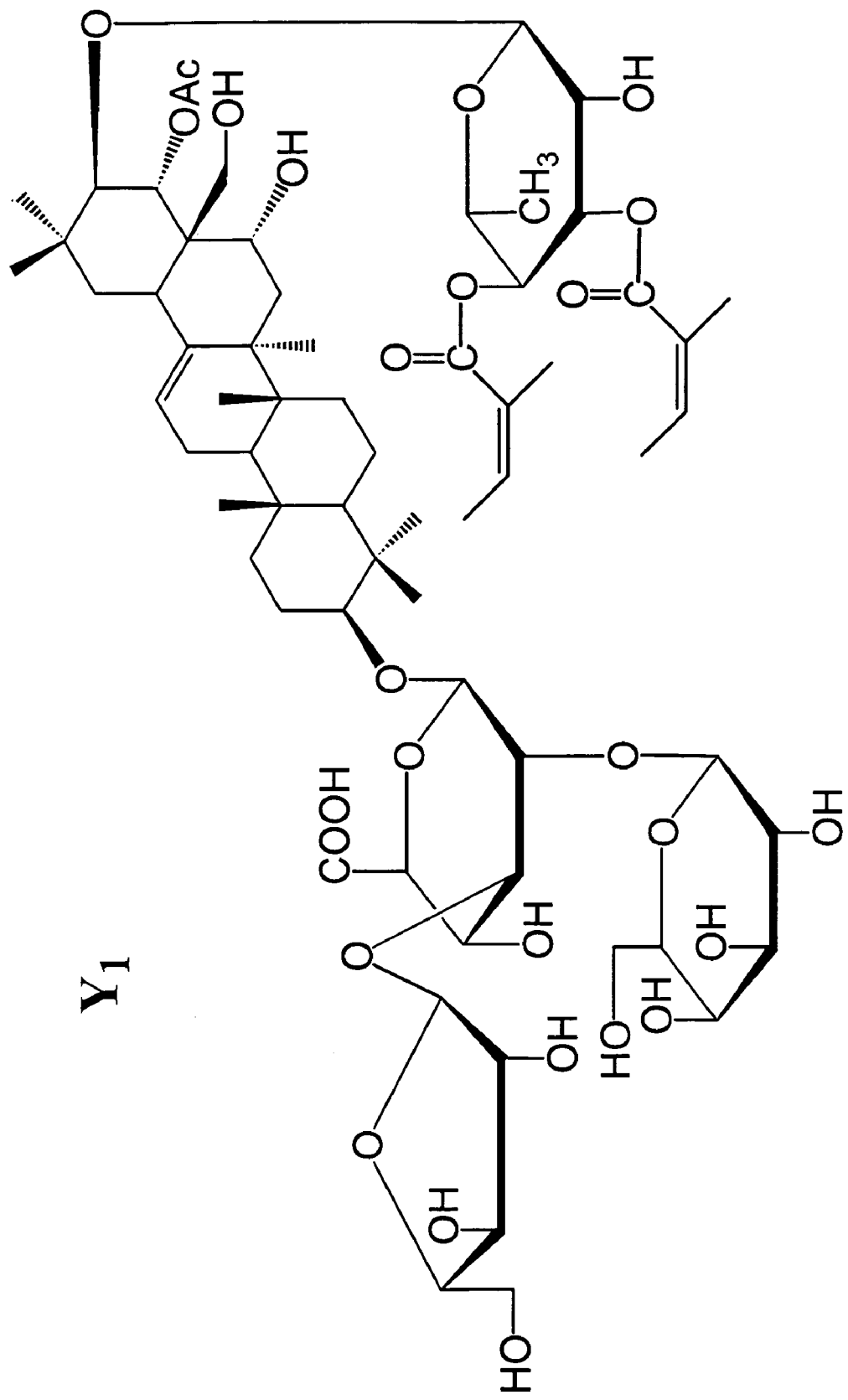

FIG. 23 shows the structure of Compound Y1 with the formula of $C_{65}H_{100}O_{27}$ and the chemical name of 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β, 16α, 21β, 22α, 28-pentahydroxyolean-12-ene.

Figure 24:
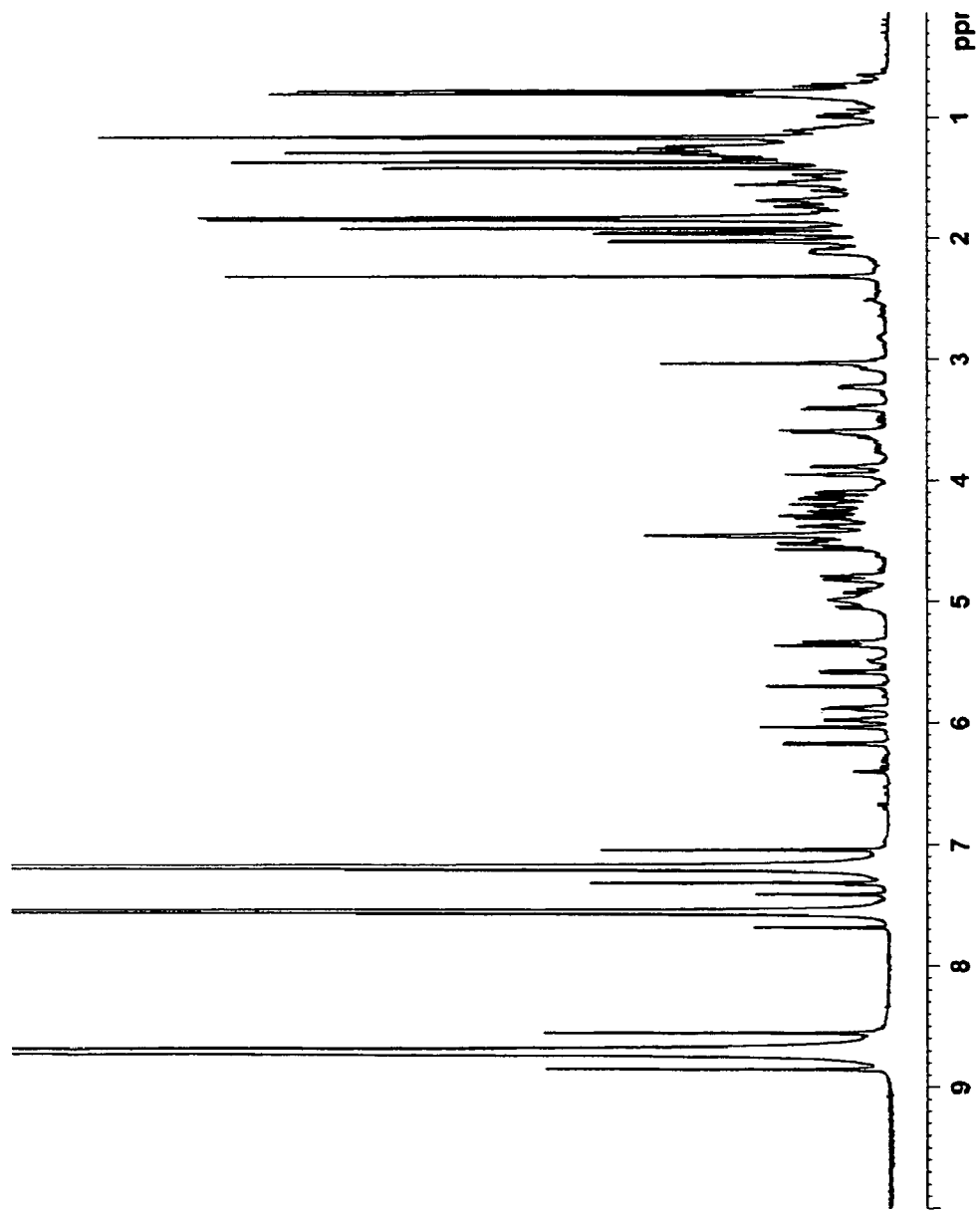

FIG. 24 shows the Proton NMR spectrum of Compound Y1.

Figure 25:
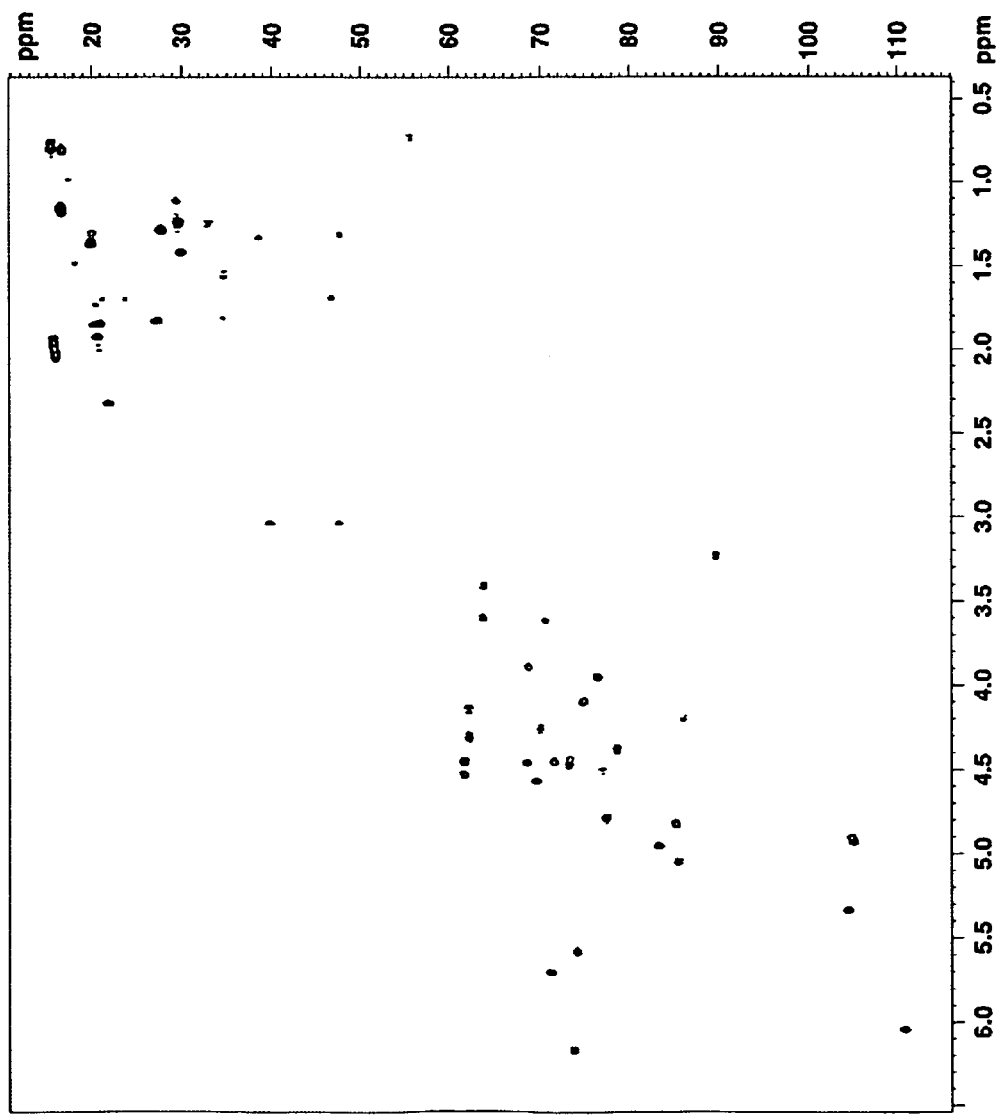

FIG. 25 shows the 2D NMR (HMQC) results of Compound Y1.

Figure 26:
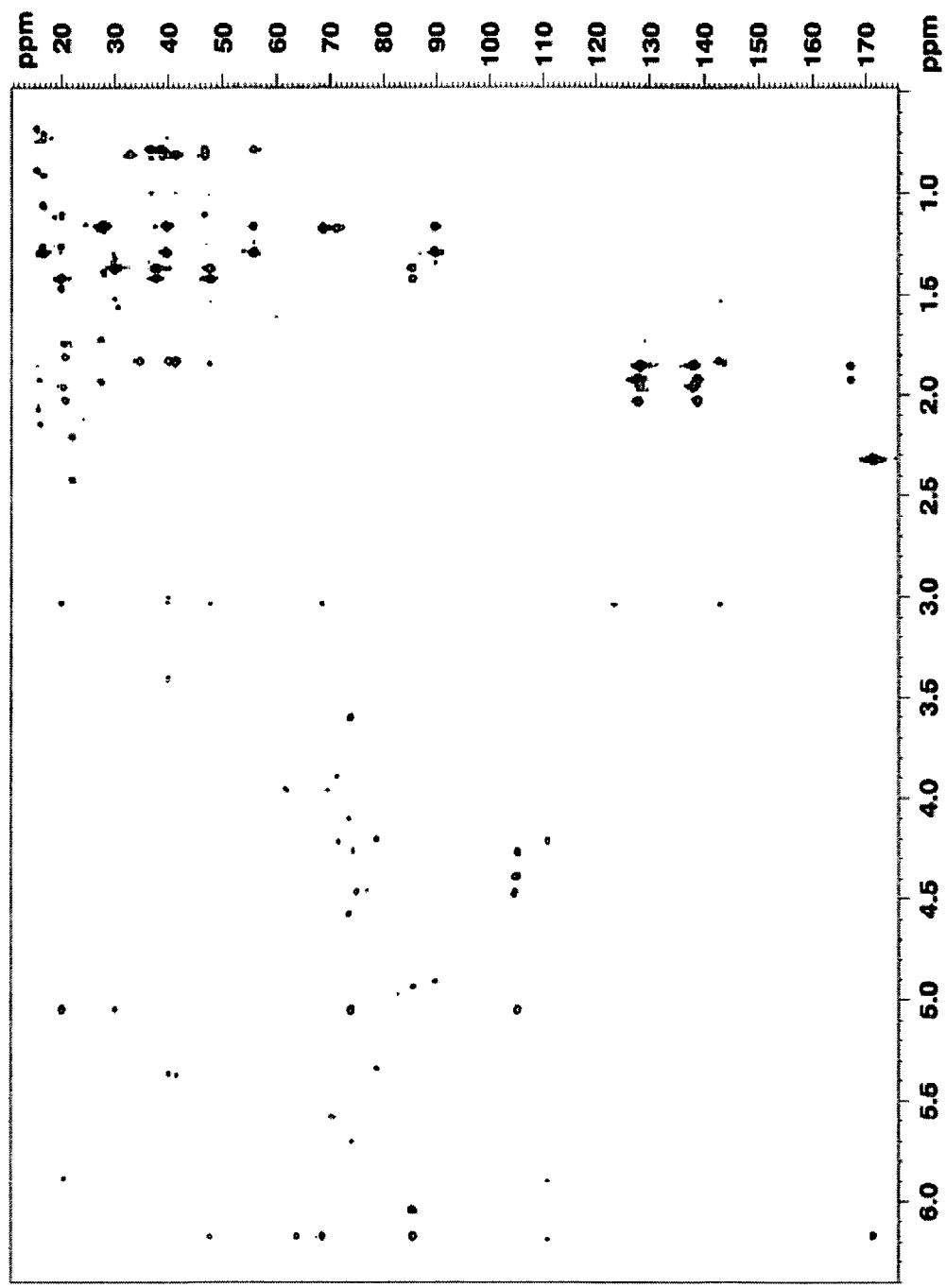

FIG. 26 shows the 2D NMR (HMBC) results of Compound Y1.

Figure 27:
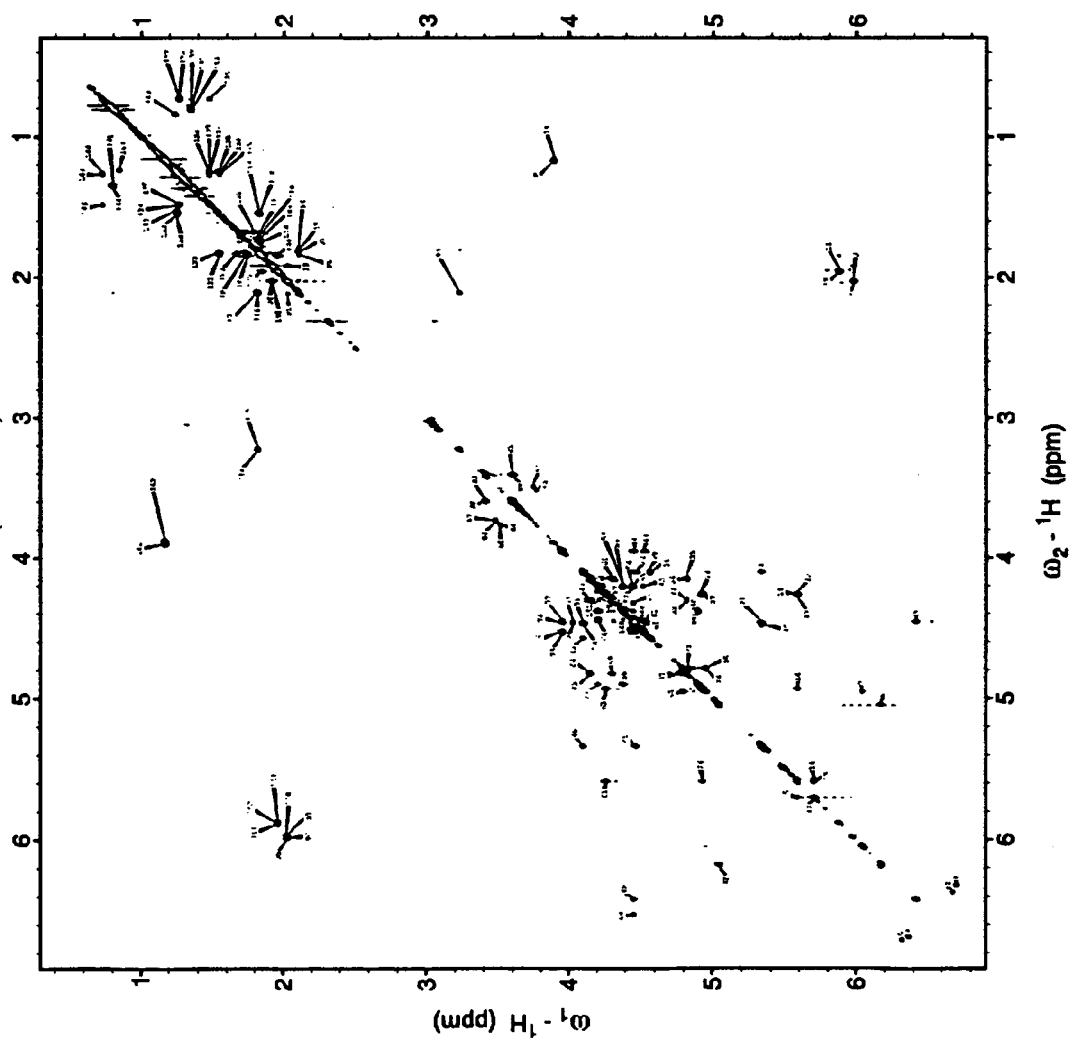

FIG. 27 shows COSY-NMR profile of Compound Y1.

Figure 28:
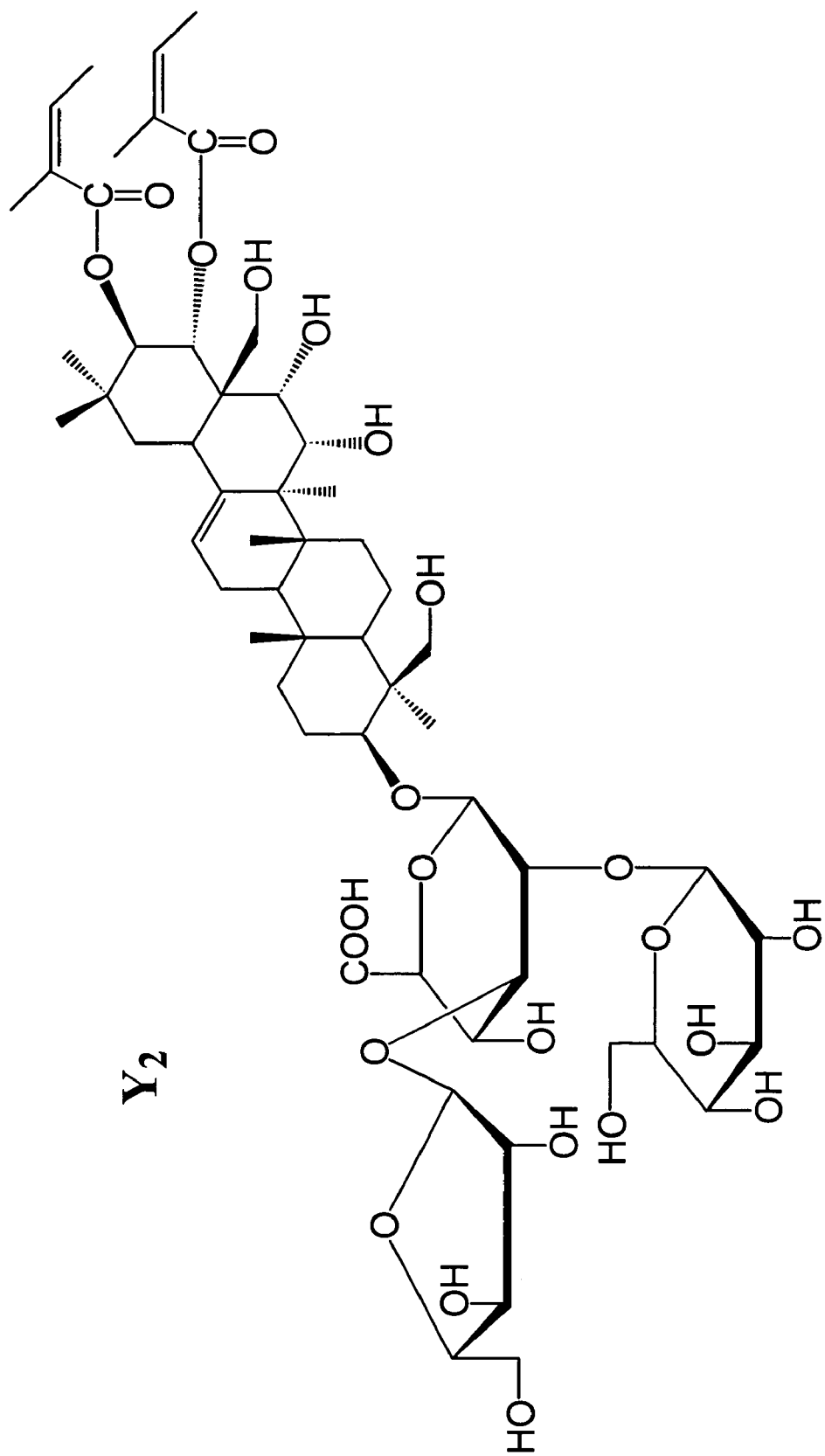

FIG. 28 shows the chemical structure and the chemical name of Compound Y2.

Figure 29:
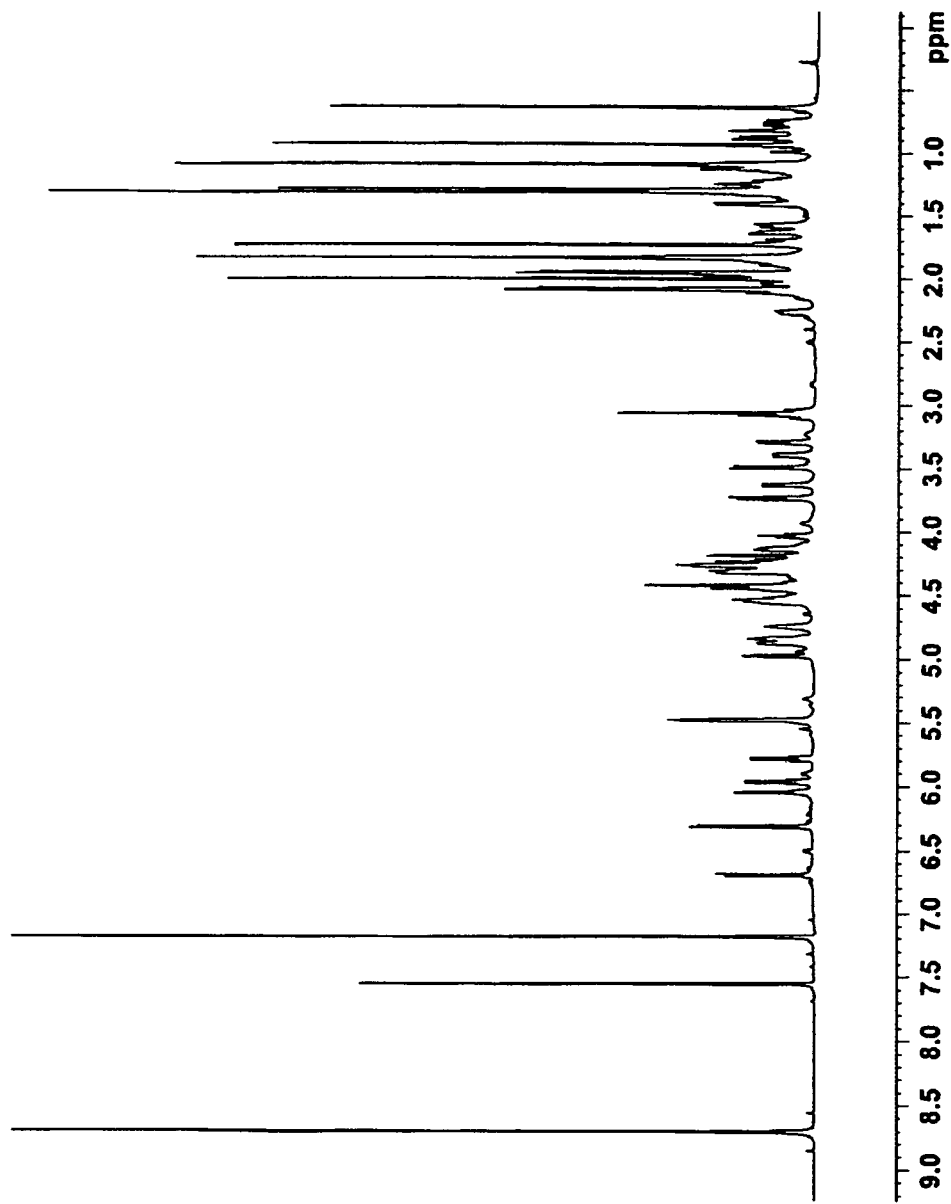

FIG. 29 shows the proton NMR spectrum of Y2.

Figure 30:
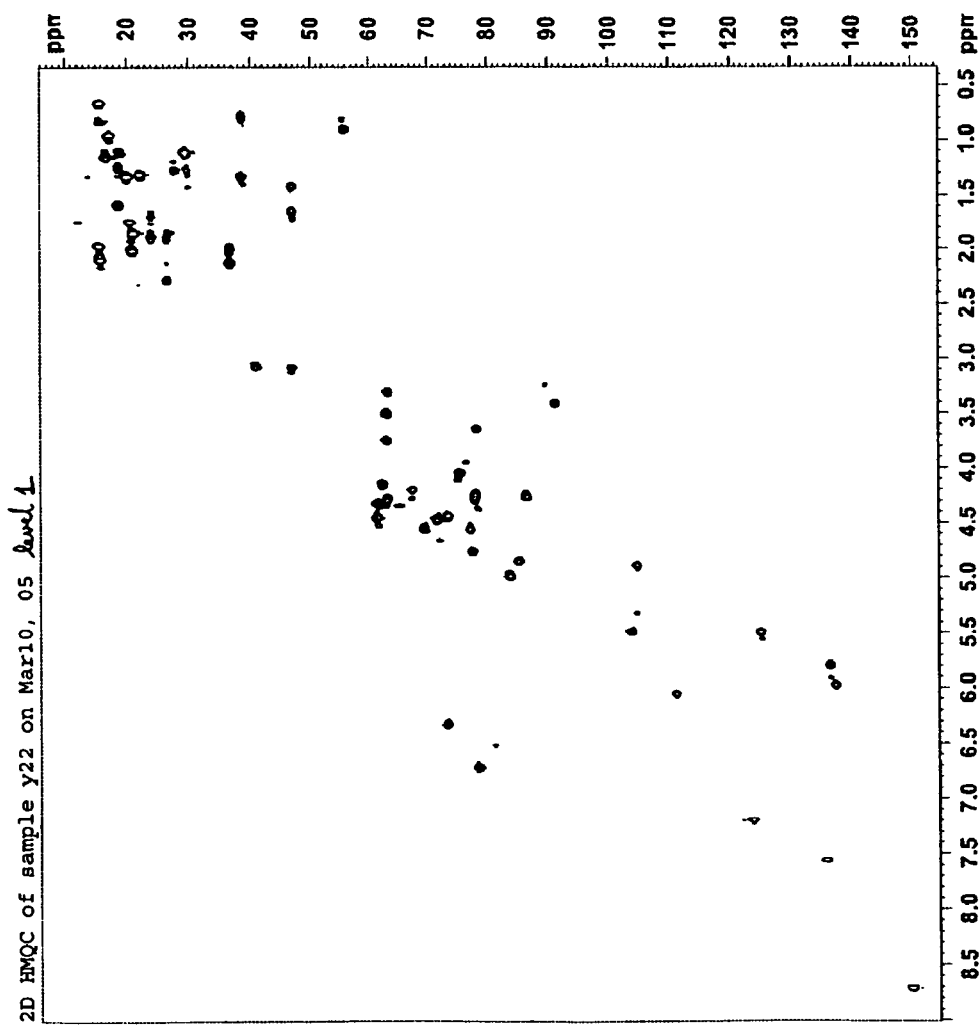

FIG. 30 shows the 2D NMR spectrum of Y2 (HMQC)-level-1.

Figure 31:
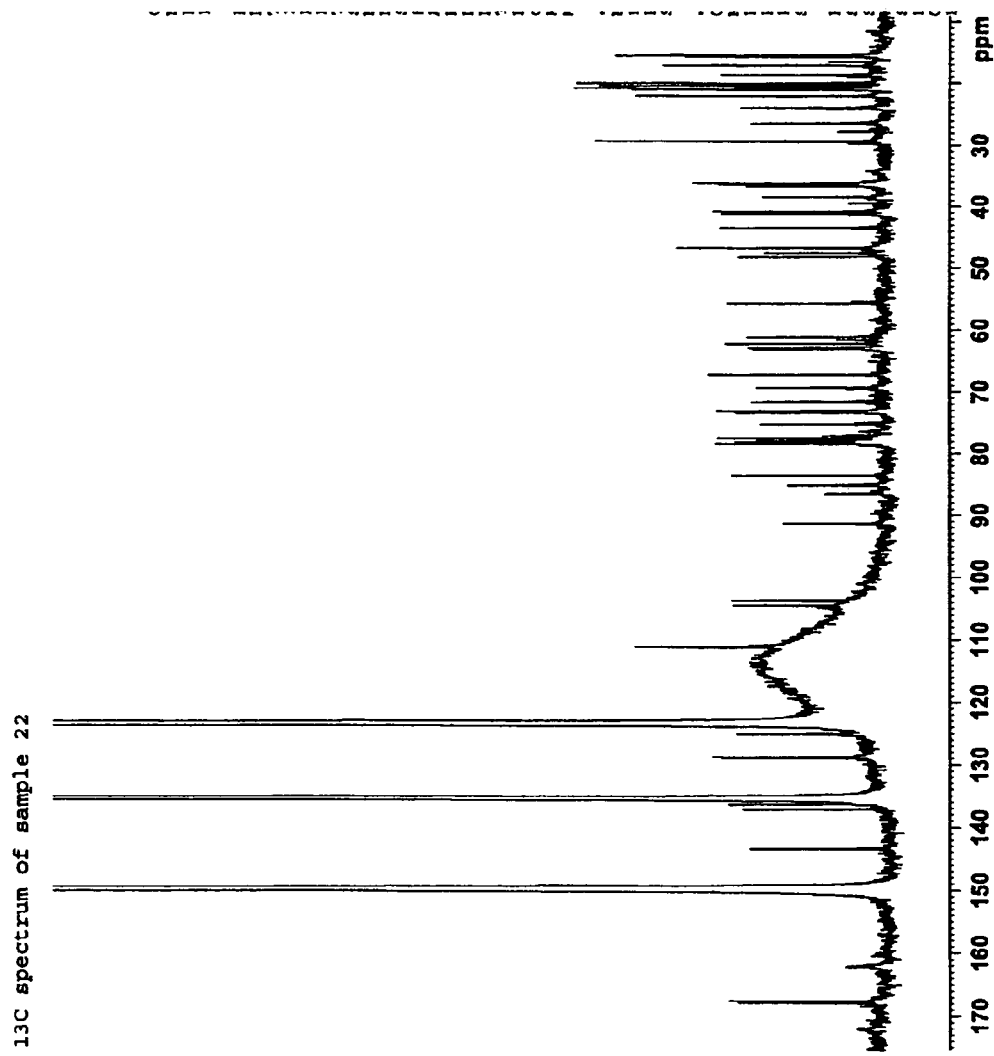

FIG. 31 shows the C13 NMR spectra of compound Y2.

Figure 32:
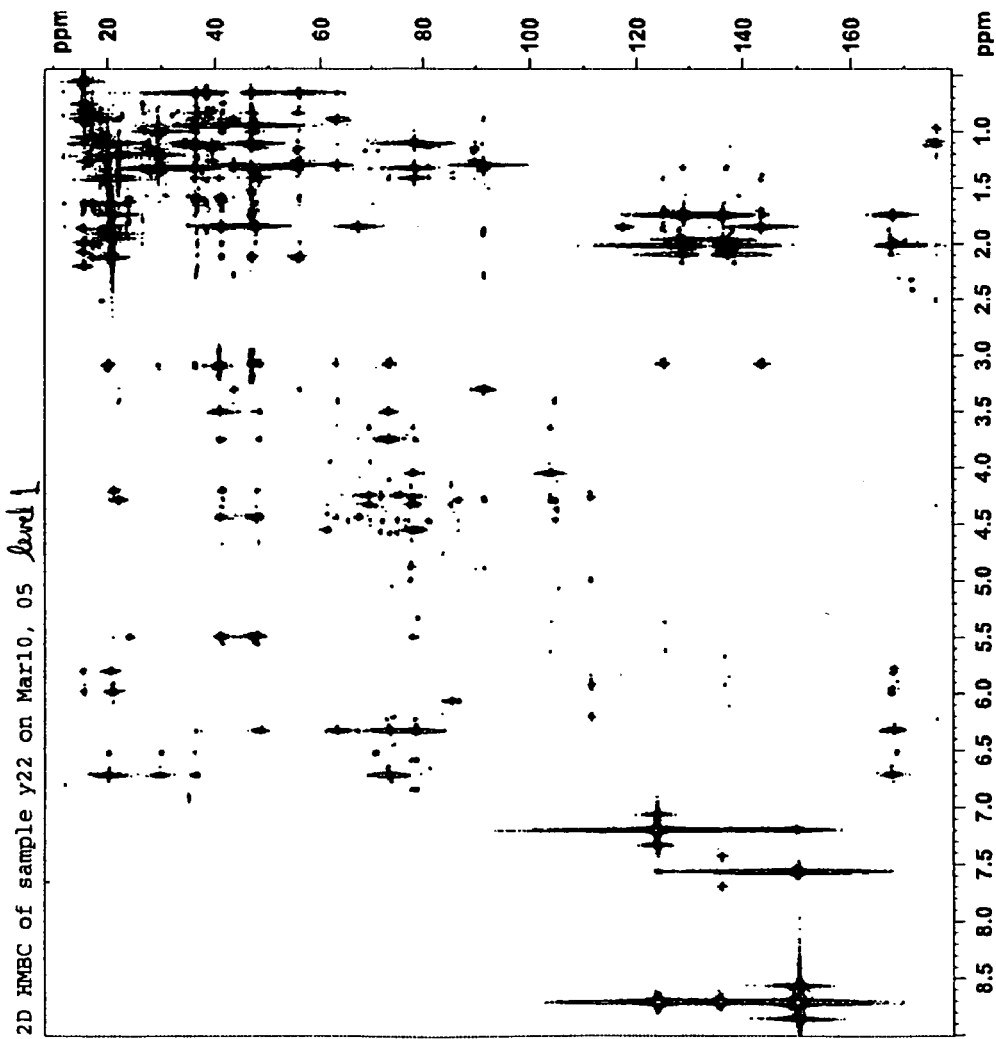

FIG. 32 shows the 2D NMR (HMBC)-level-1 spectra of compound Y2.

Figure 33:
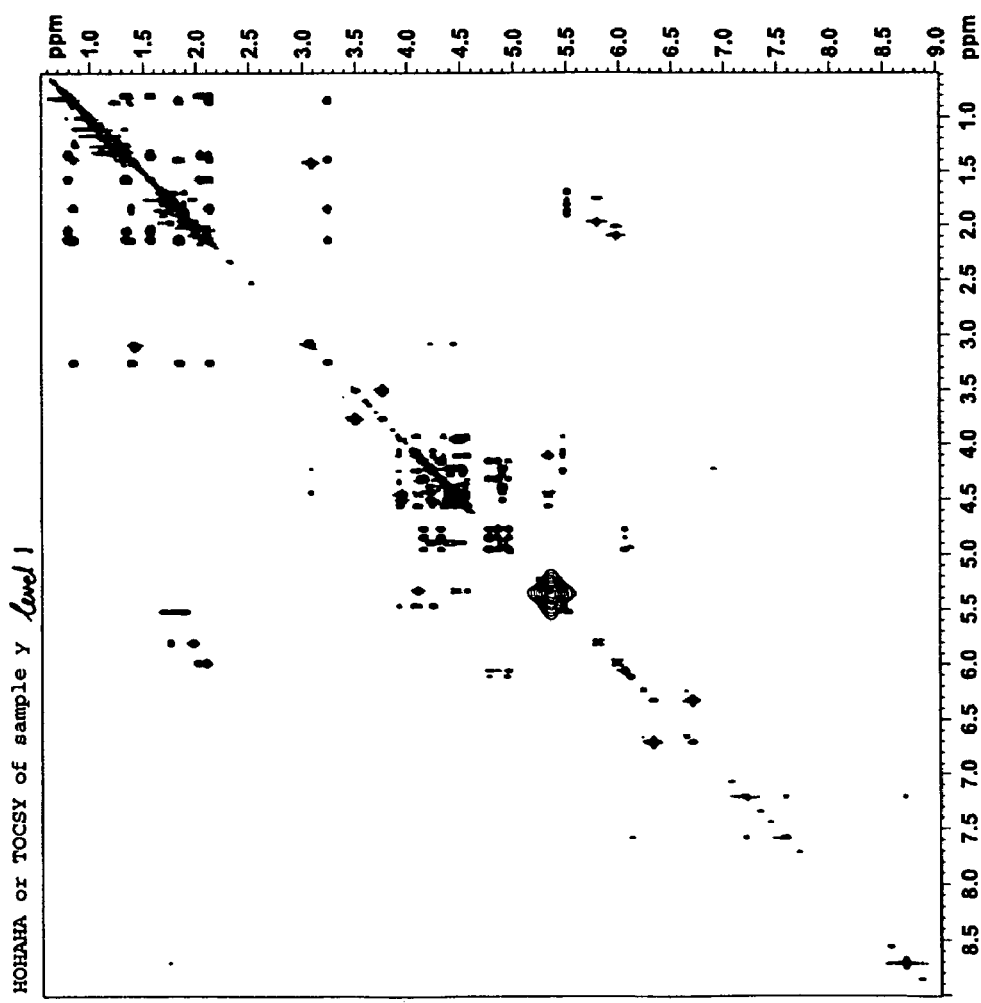

FIG. 33 shows the 2D NMR HOHAHA (TOCSY)-level-1 spectrum of compound Y2.

Figure 34:
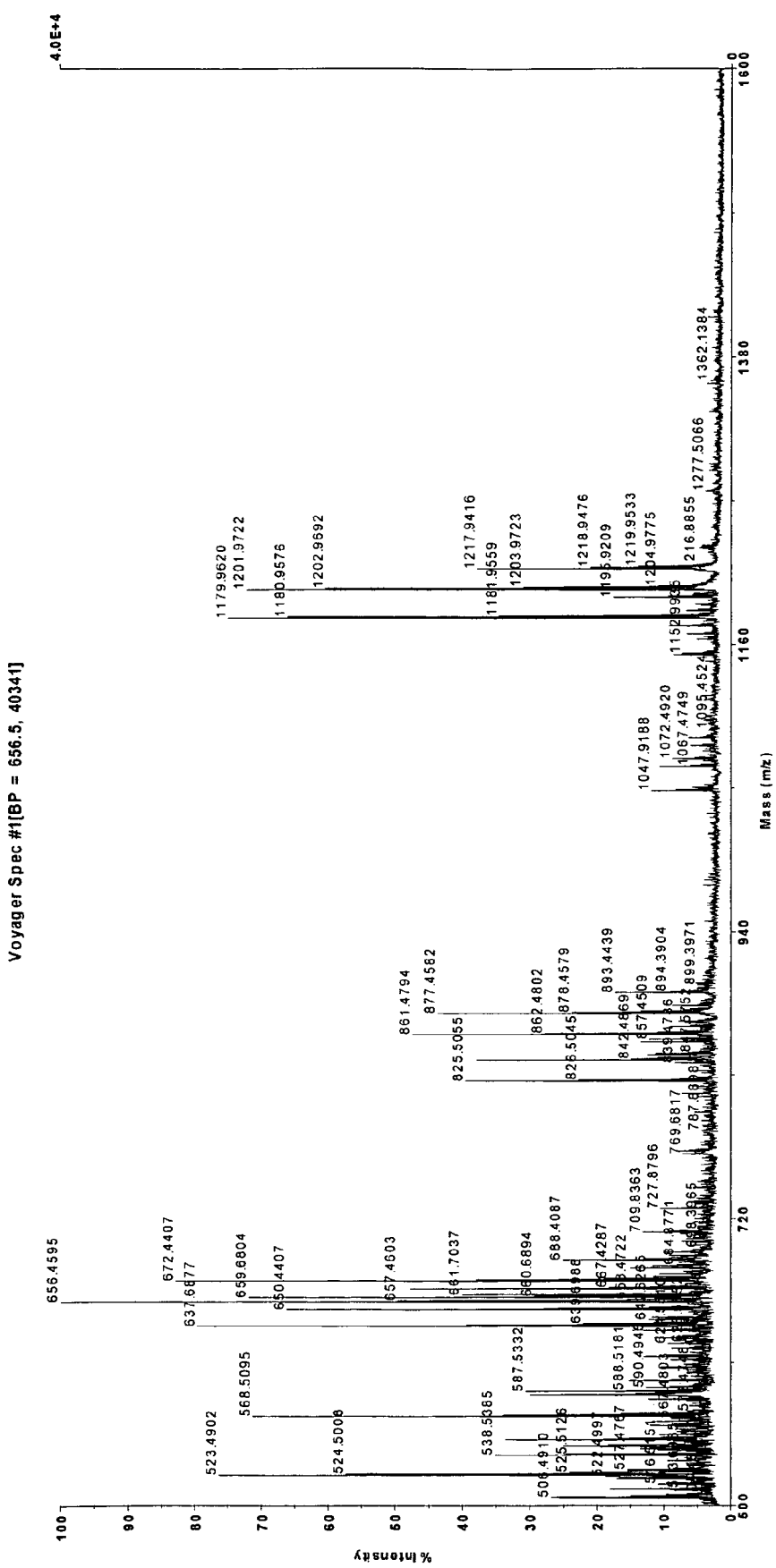

FIG. 34 shows the Mass spectrum of compound Y2+Matrix+Standards.

Figure 35:
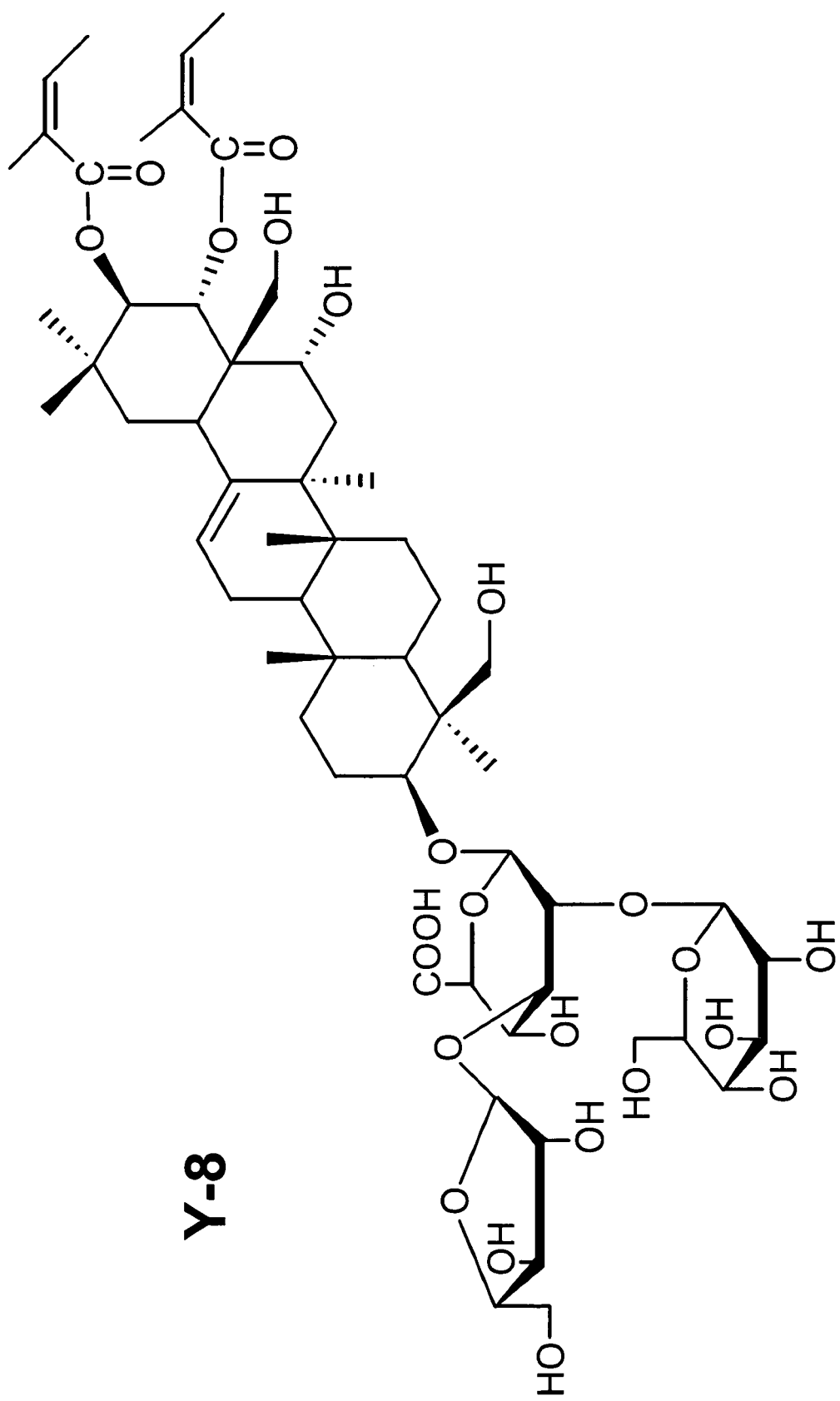

FIG. 35 shows the chemical structure of Y8.

Figure 36:
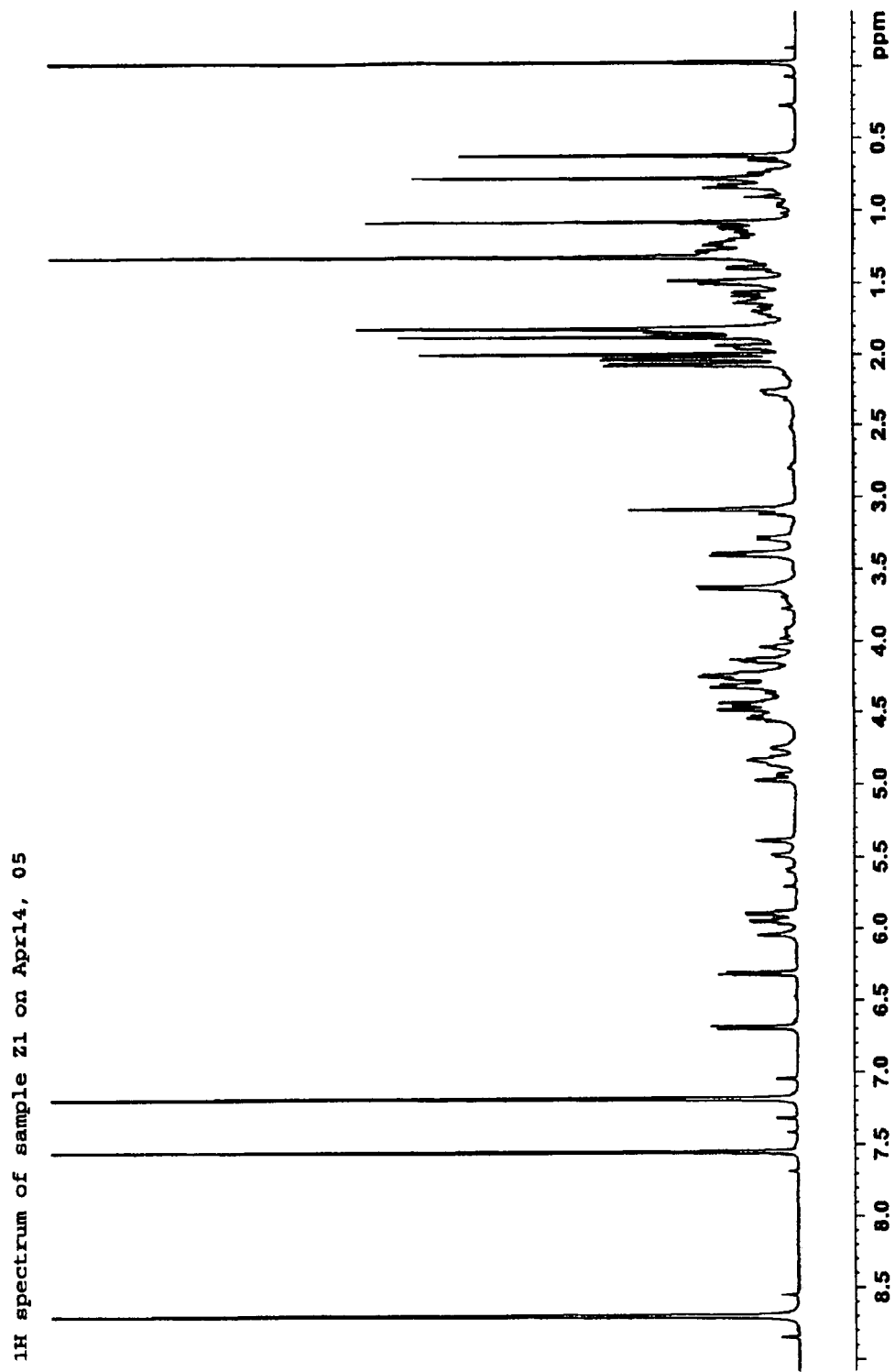

FIG. 36 shows H-NMR spectrum of Y8.

Figure 37:
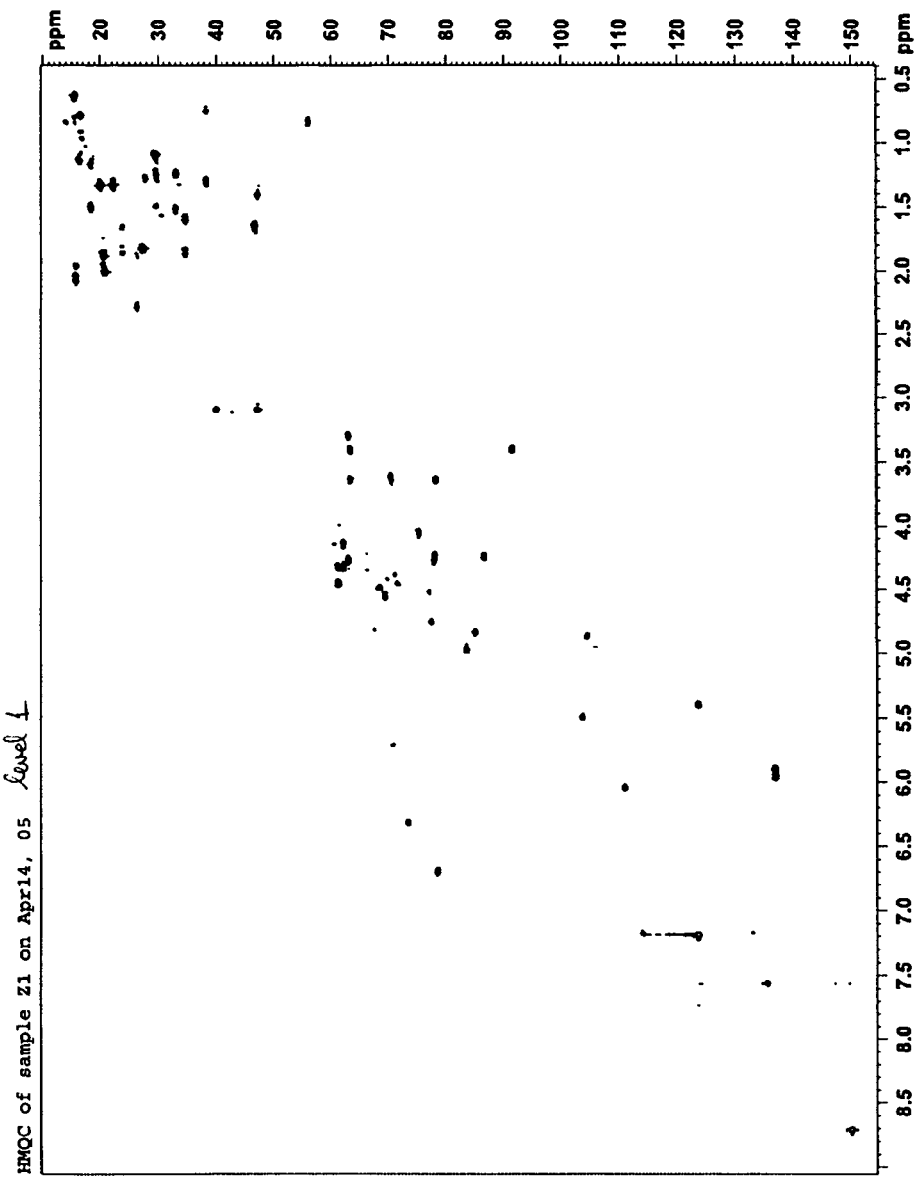

FIG. 37 shows 2D NMR HMQC (level 1) spectrum of Y8.

Figure 38:
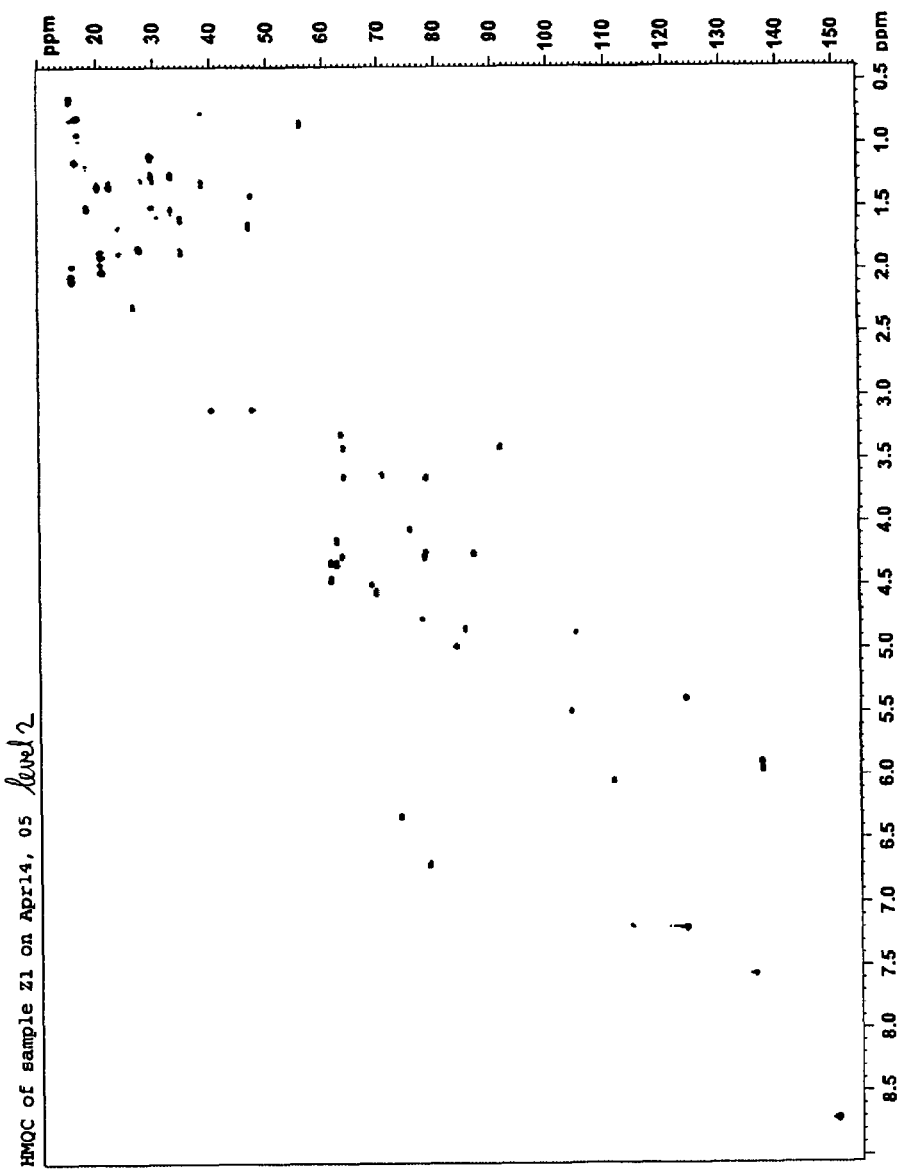

FIG. 38 shows 2D NMR HMQC (level 2) spectrum of Y8.

Figure 39:
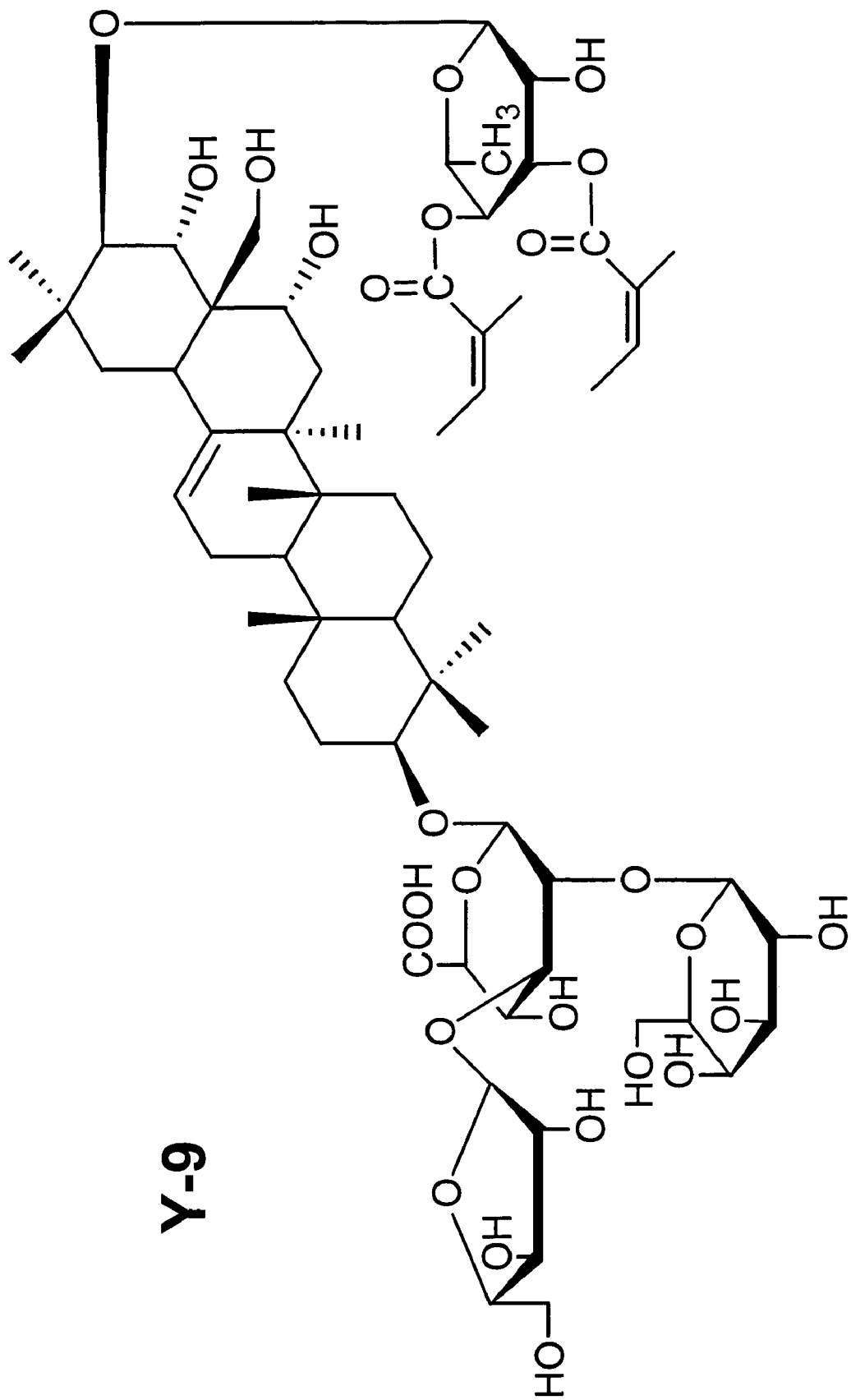

FIG. 39 shows the chemical structure of Y9.

Figure 40:
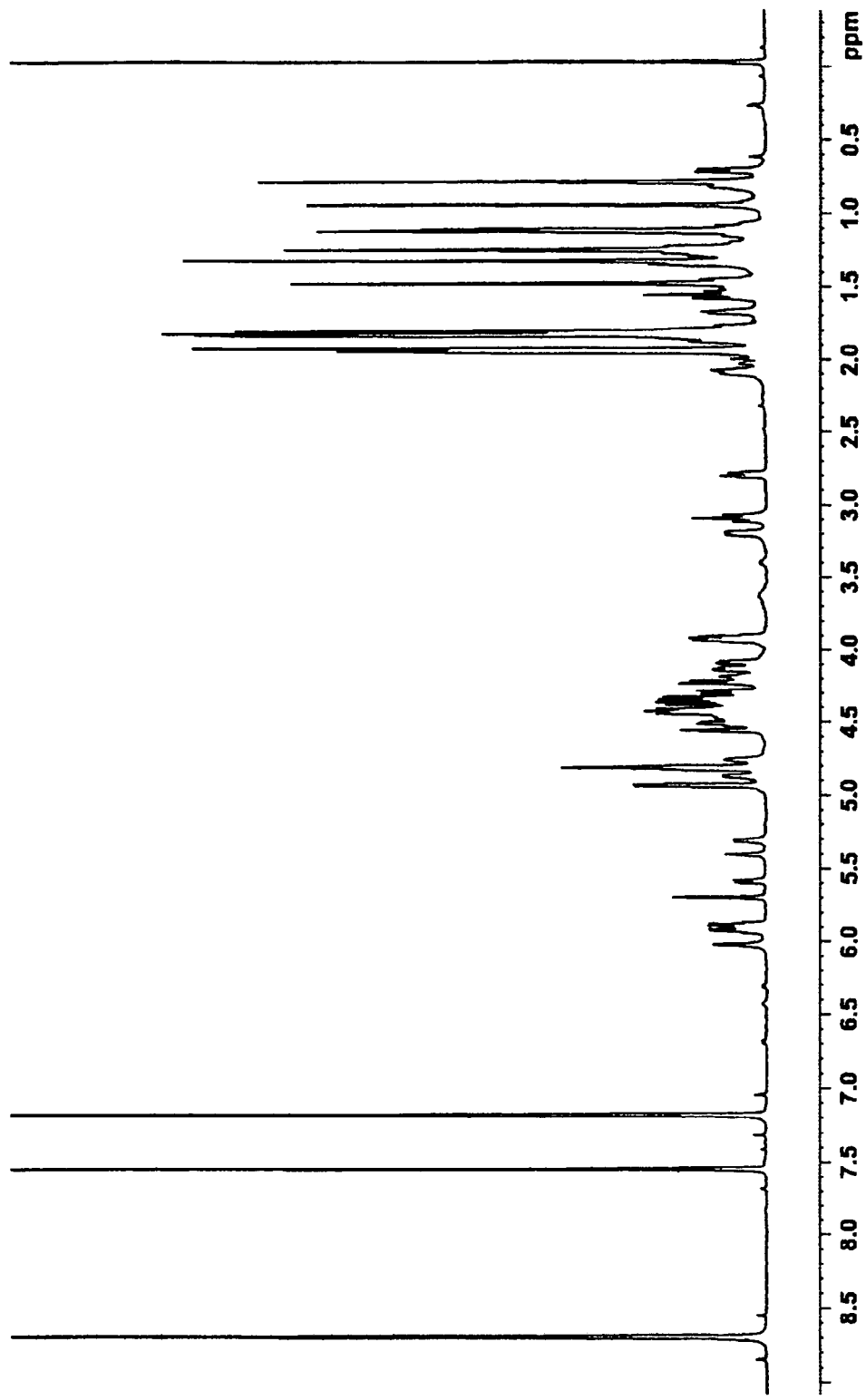

FIG. 40 shows H-NMR spectrum of Y9.

Figure 41:
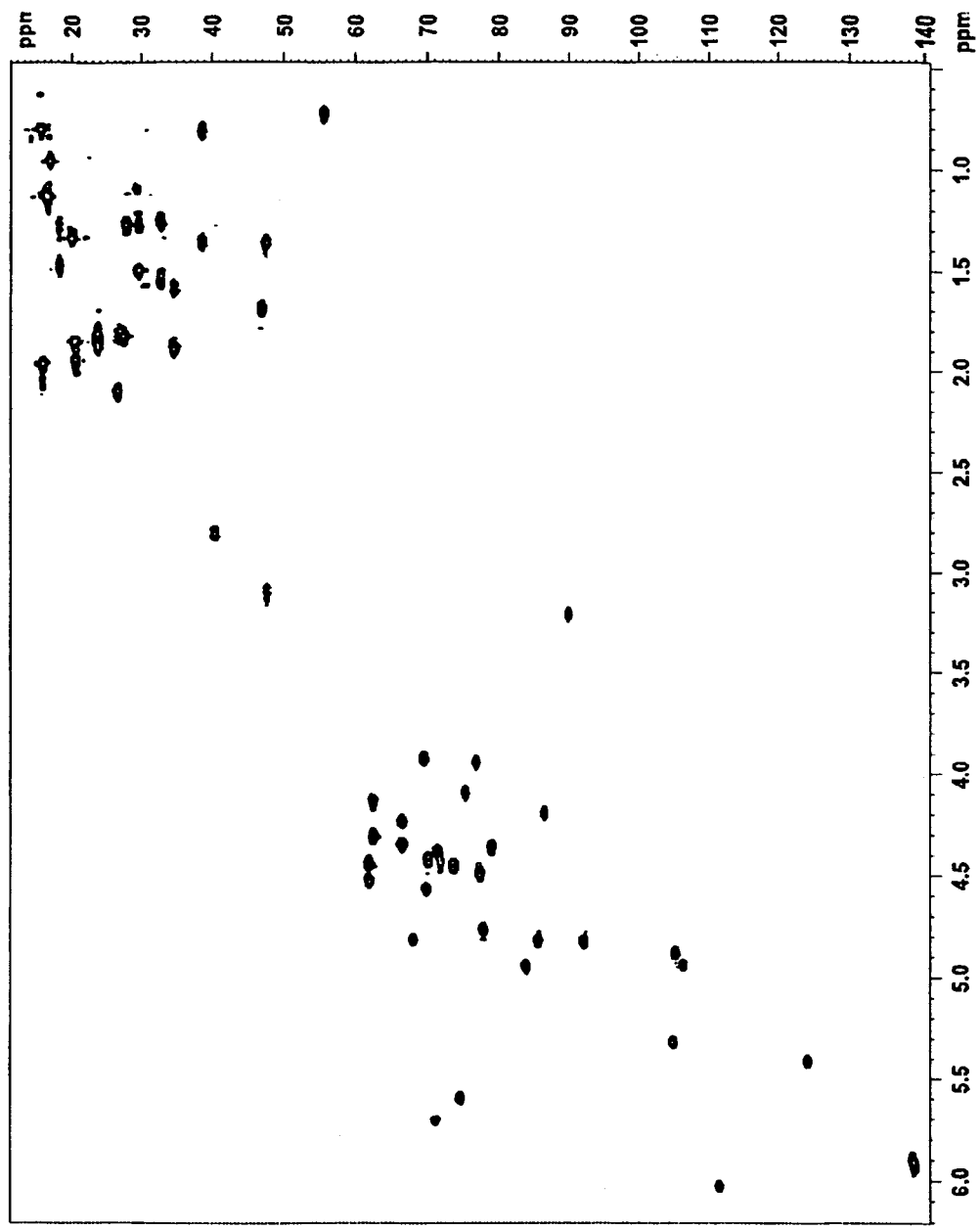

FIG. 41 shows 2D NMR HMQC (level 1) spectrum of Y9.

Figure 42:
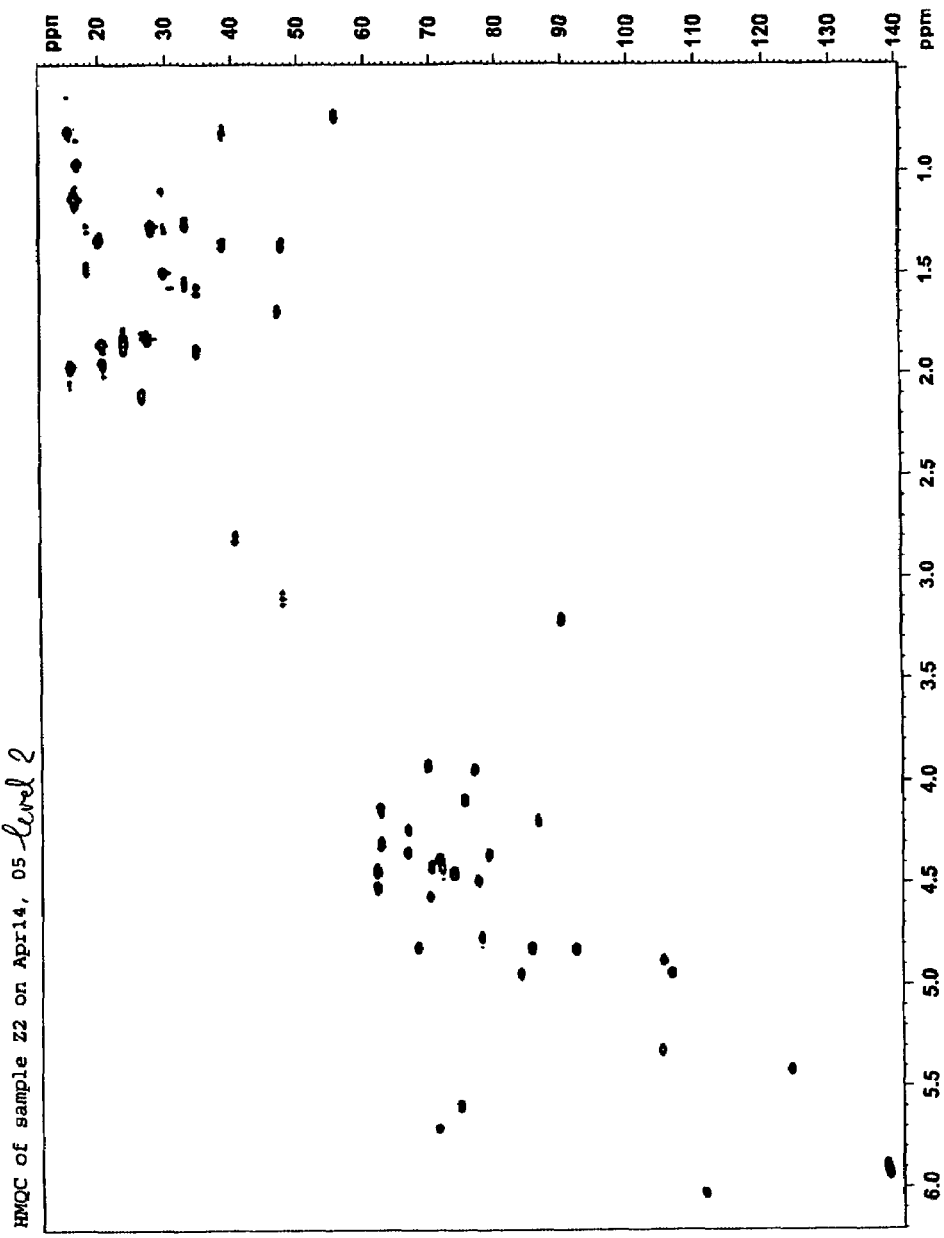

FIG. 42 shows 2D NMR HMQC (level 2) spectrum of Y9.

Figure 43:
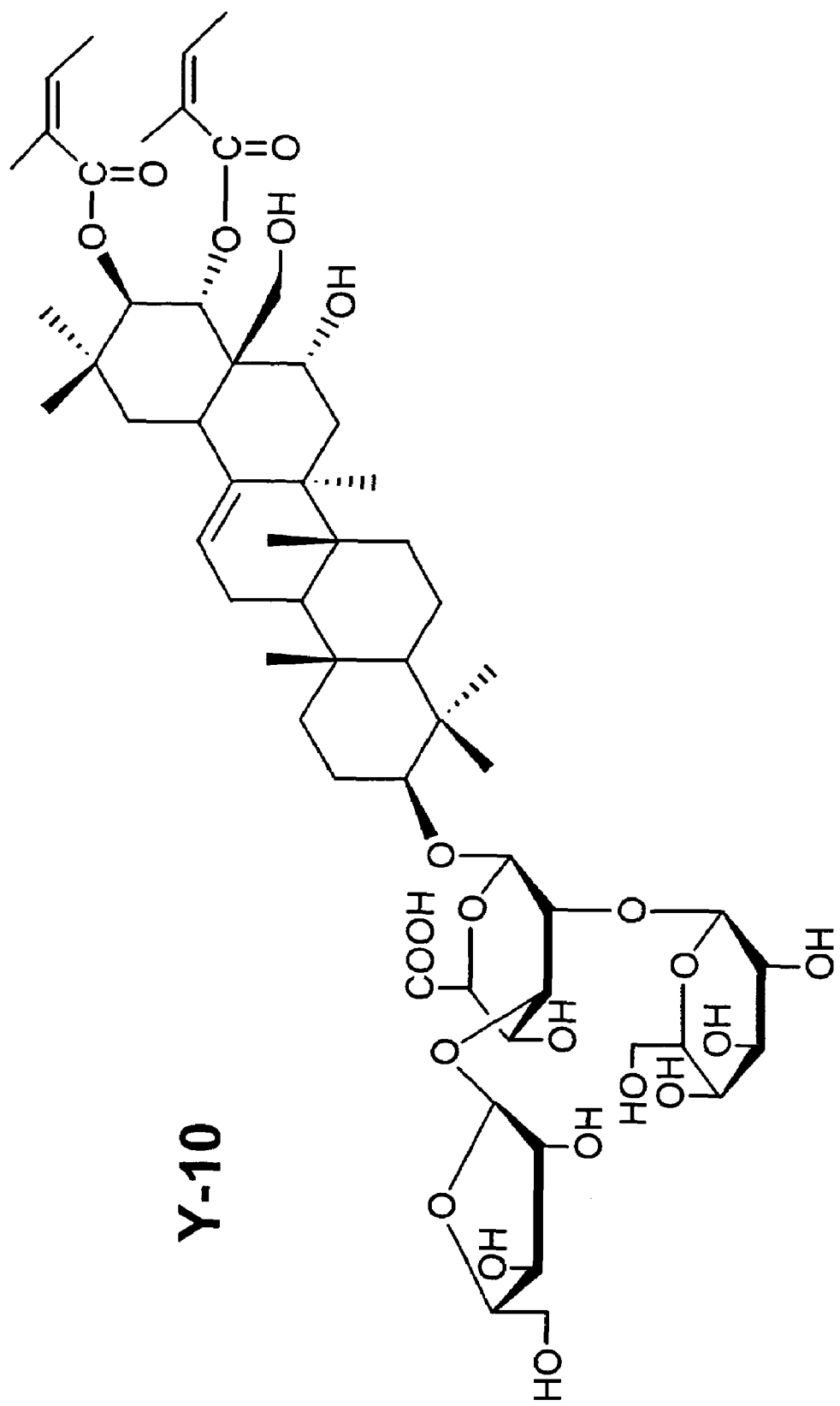

FIG. 43 shows the chemical structure of Y10.

Figure 44:
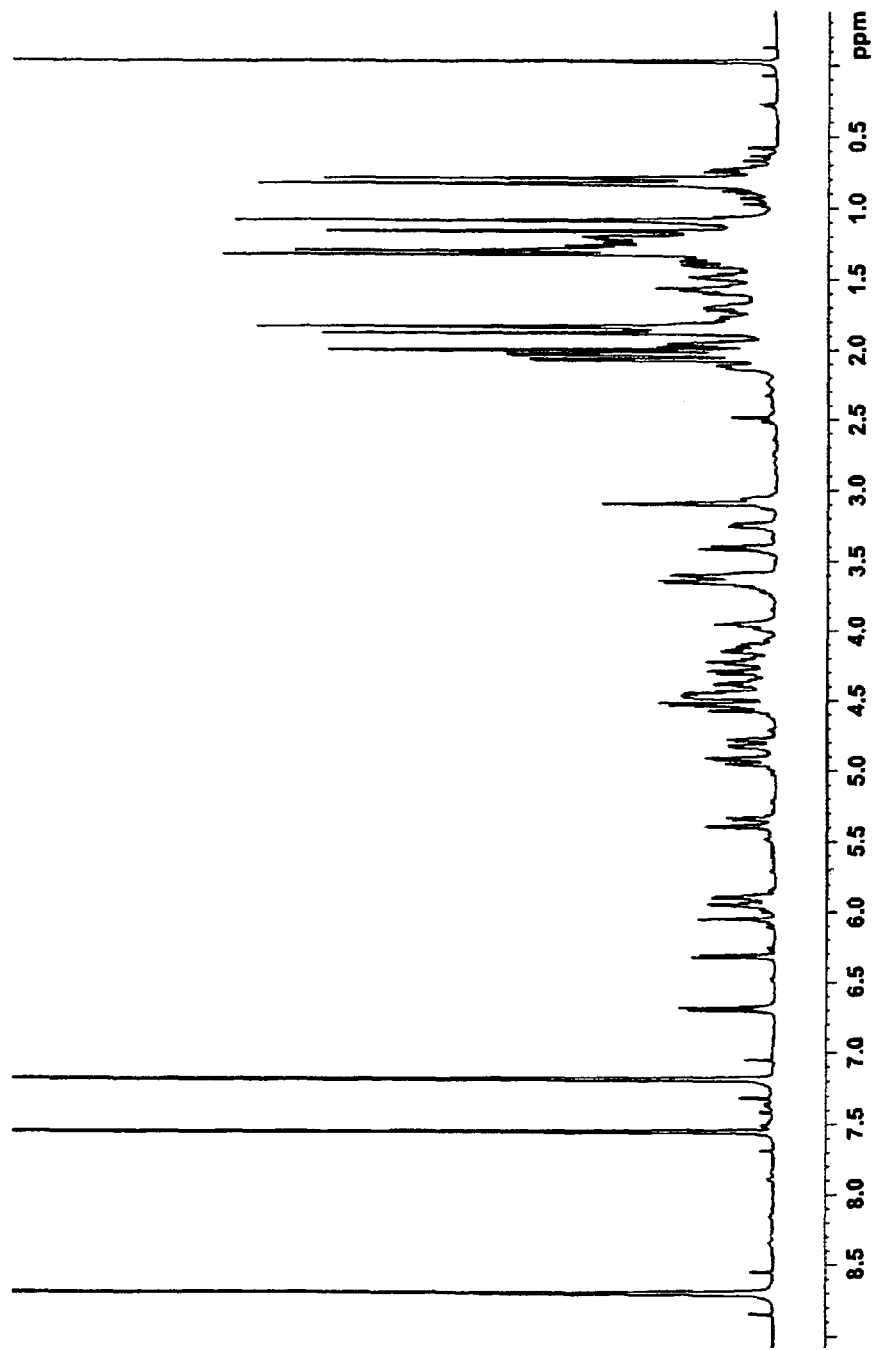

FIG. 44 shows H-NMR spectrum of Y10.

Figure 45:
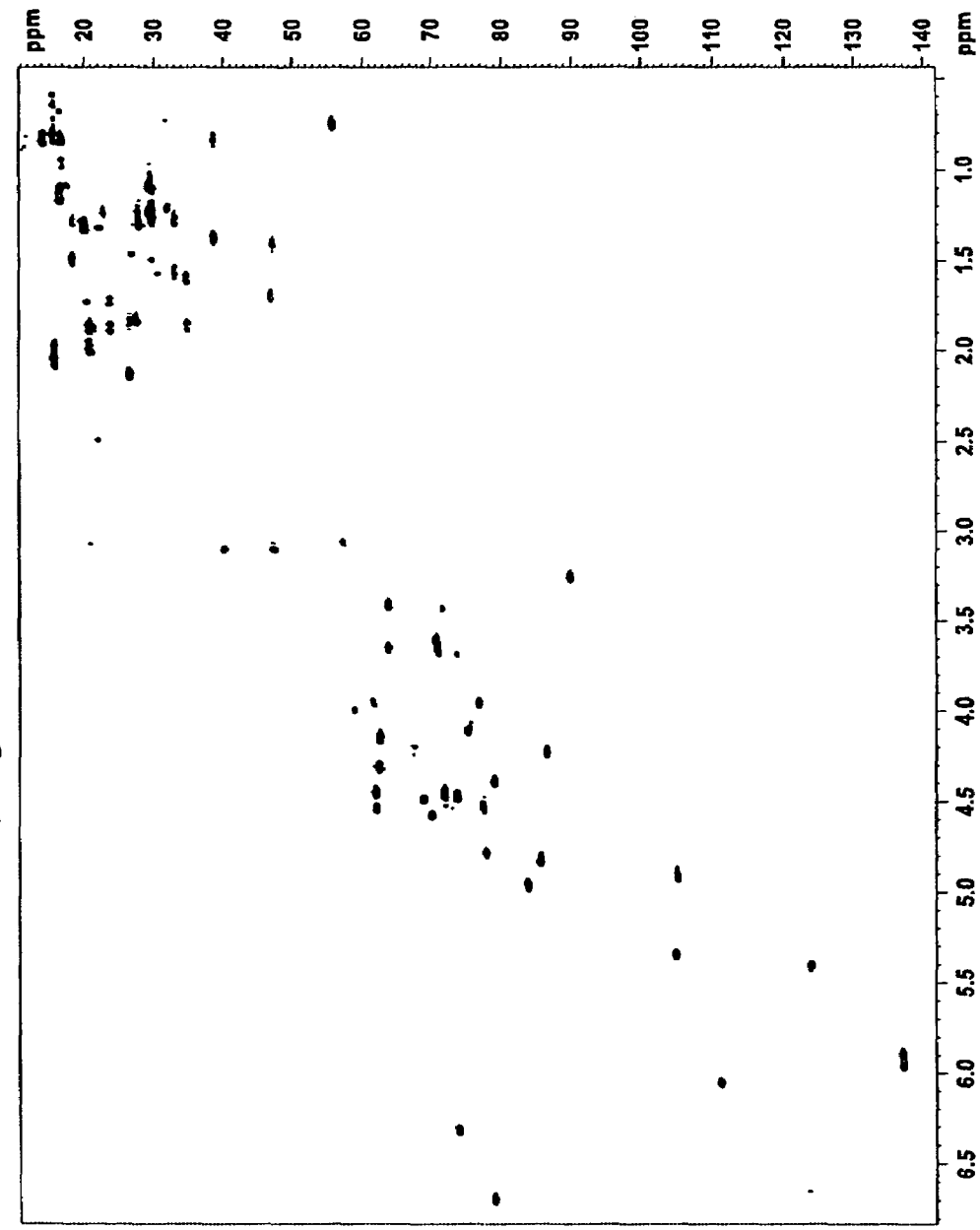

FIG. 45 shows 2D NMR HMQC (level 1) spectrum of Y10.

Figure 46:
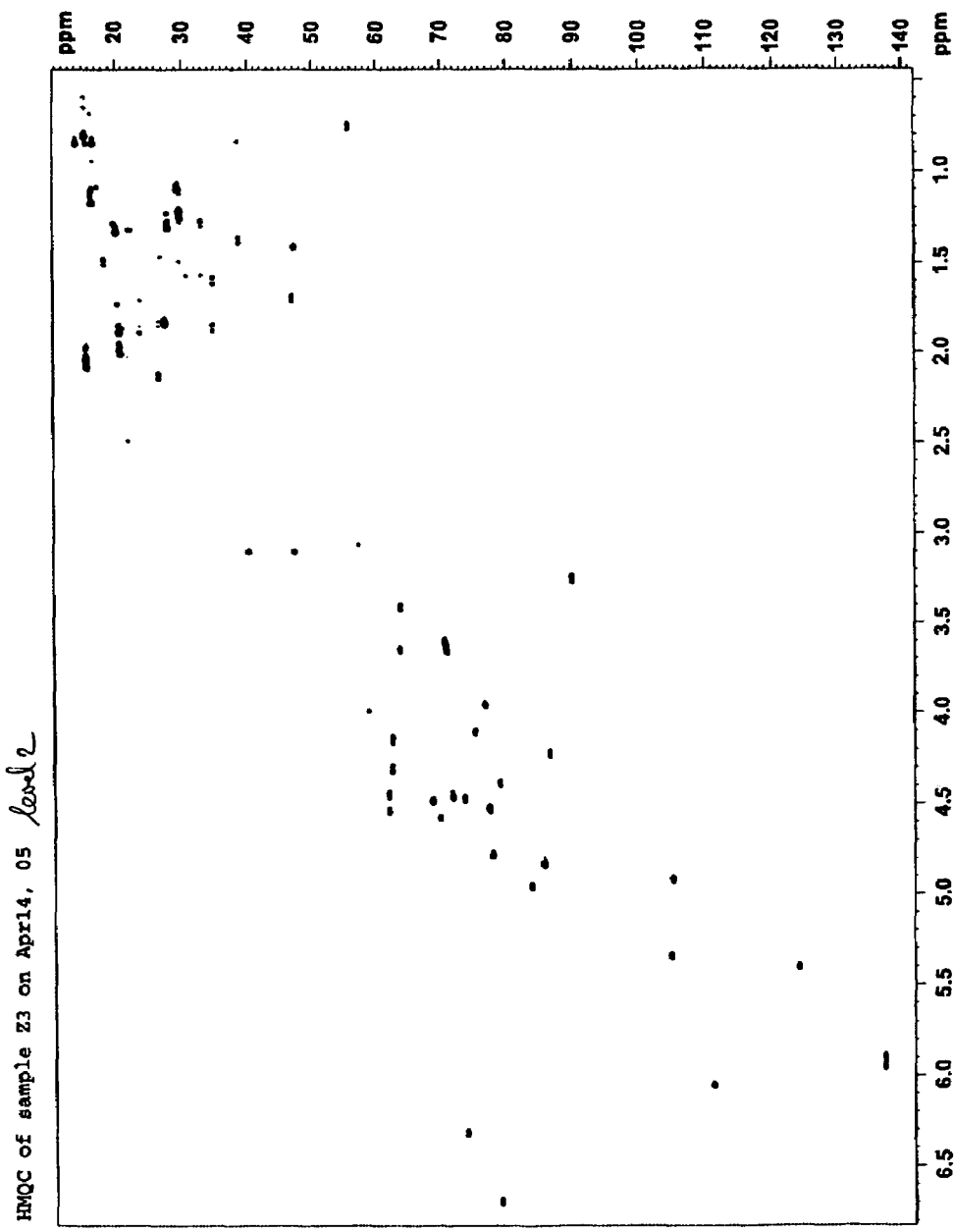

FIG. 46 shows 2D NMR HMQC (level 2) spectrum of Y10.

Figure 47:
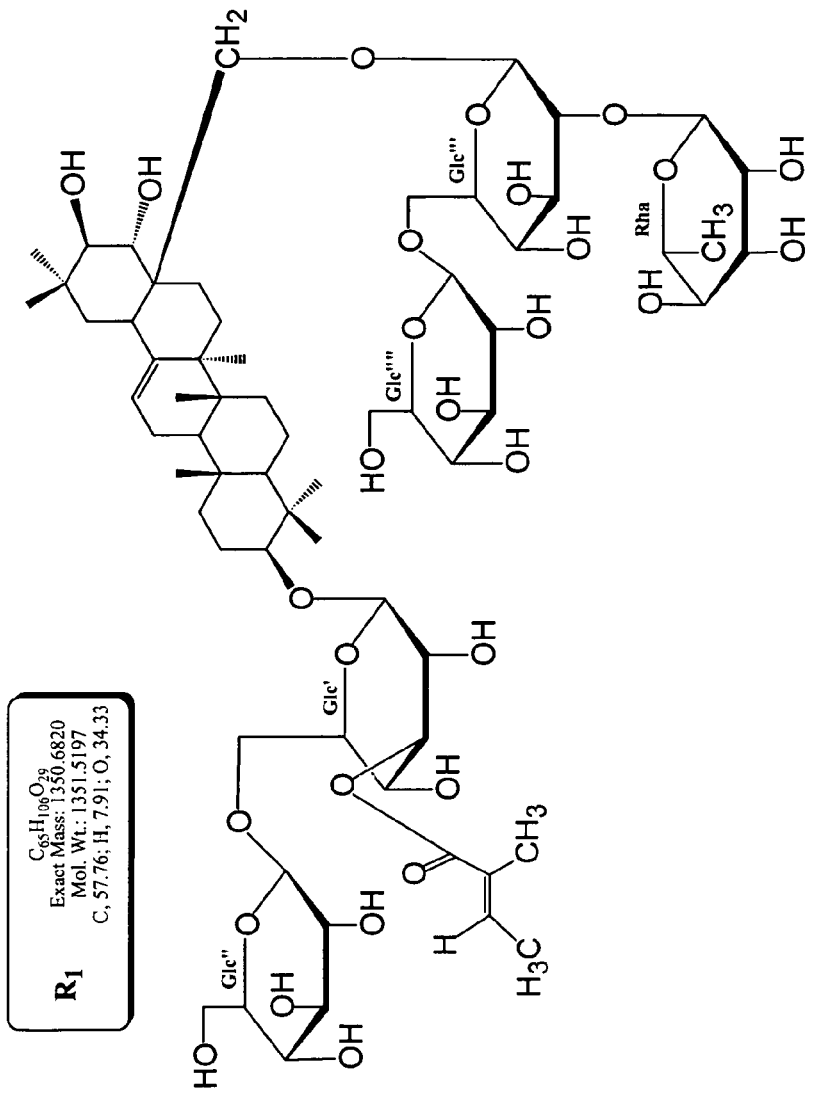

FIG. 47 shows the chemical structure and the chemical name of Compound R1.

Figure 48:
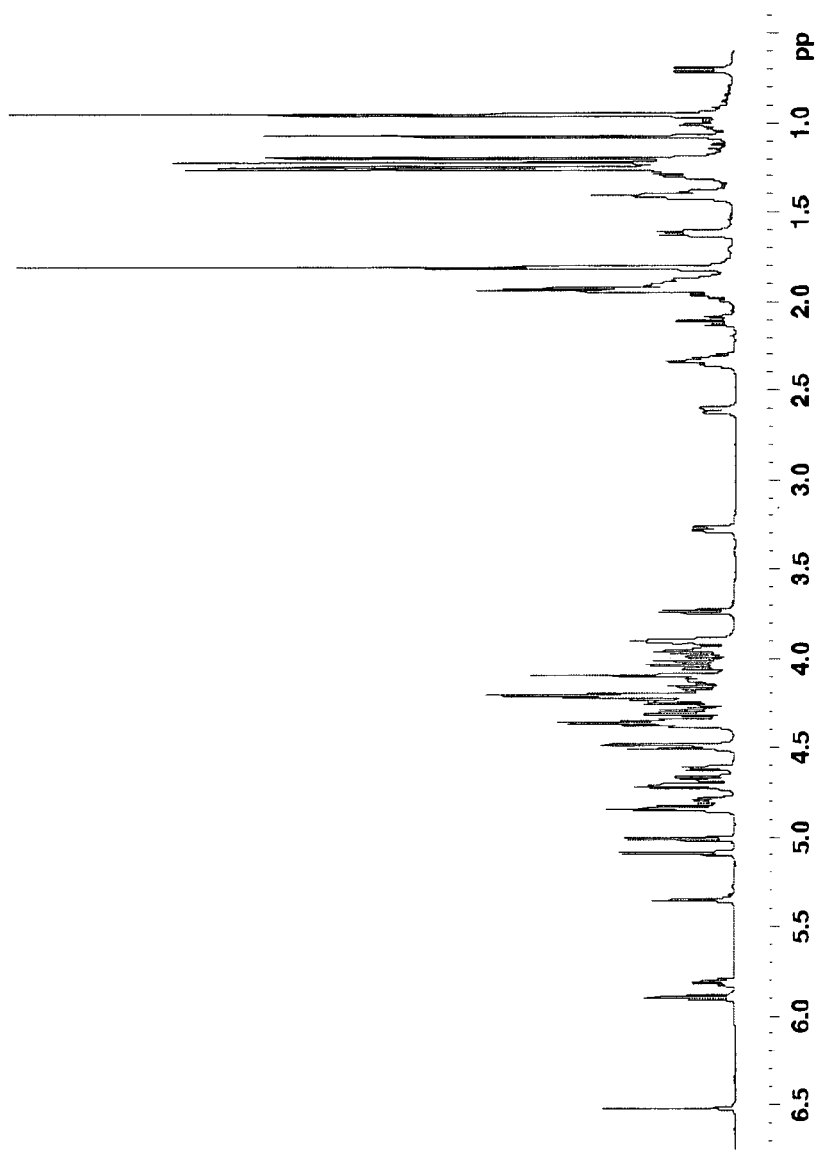

FIG. 48 shows the Proton-NMR spectrum of compound R1.

Figure 49:
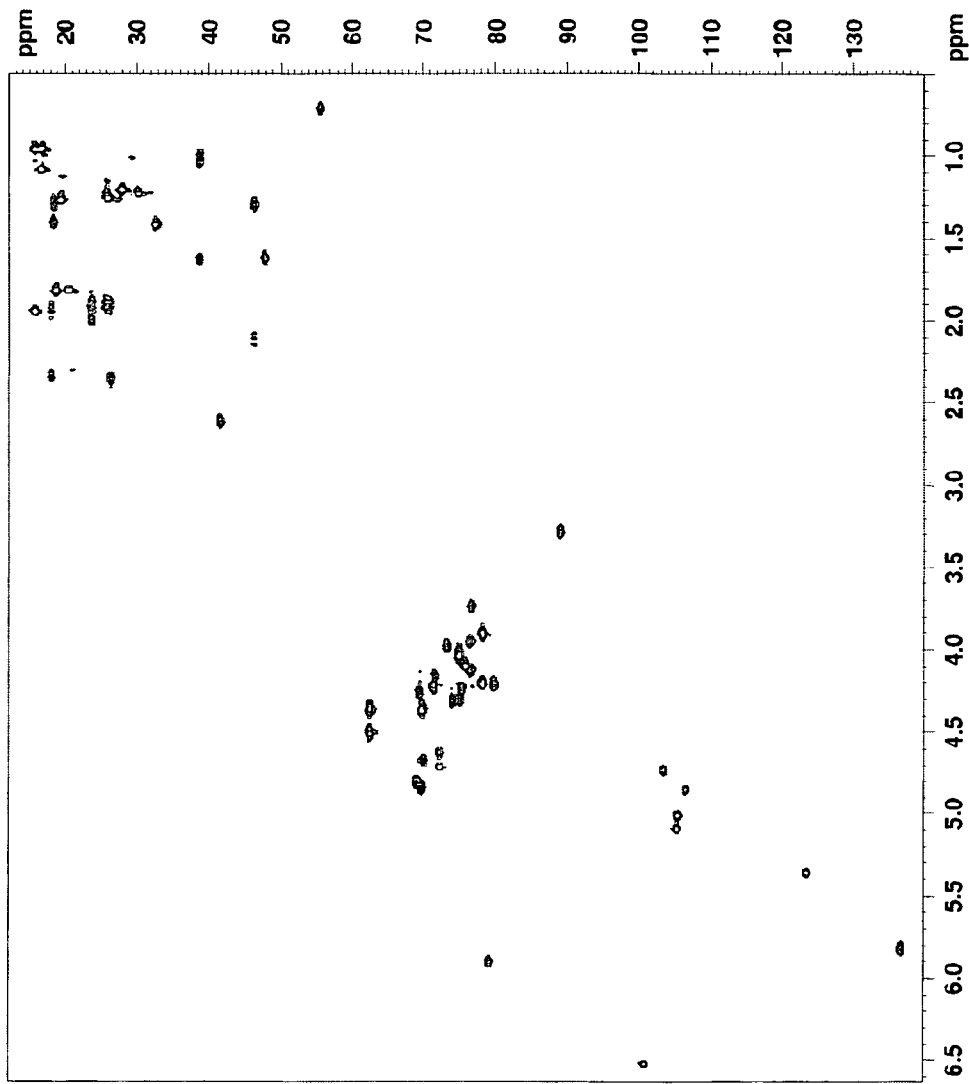

FIG. 49 shows the 2D NMR (HMQC) spectrum of compound R1.

Figure 50:
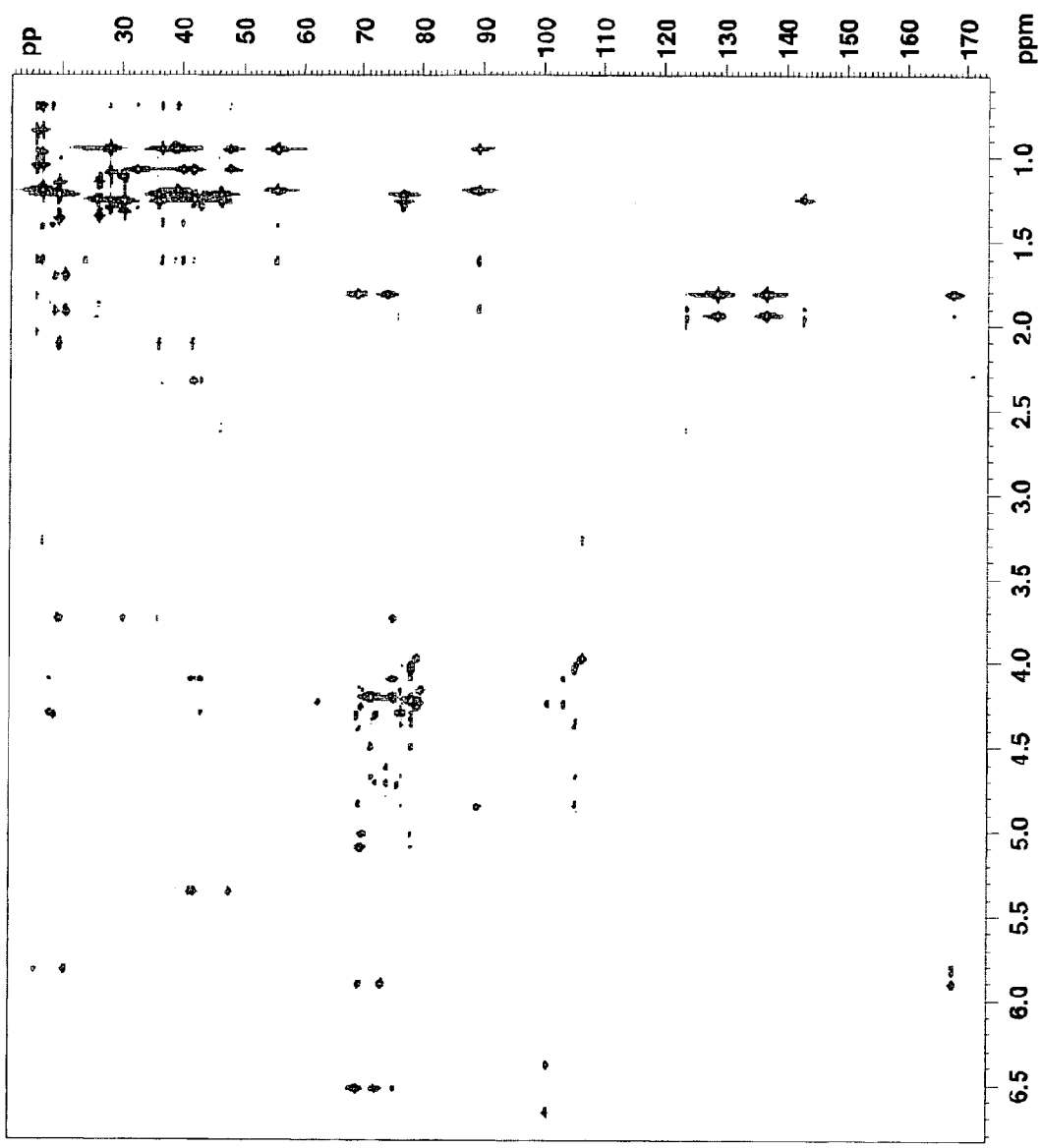

FIG. 50 shows the 2D NMR (HMBC) spectrum of compound R1.

Figure 51:
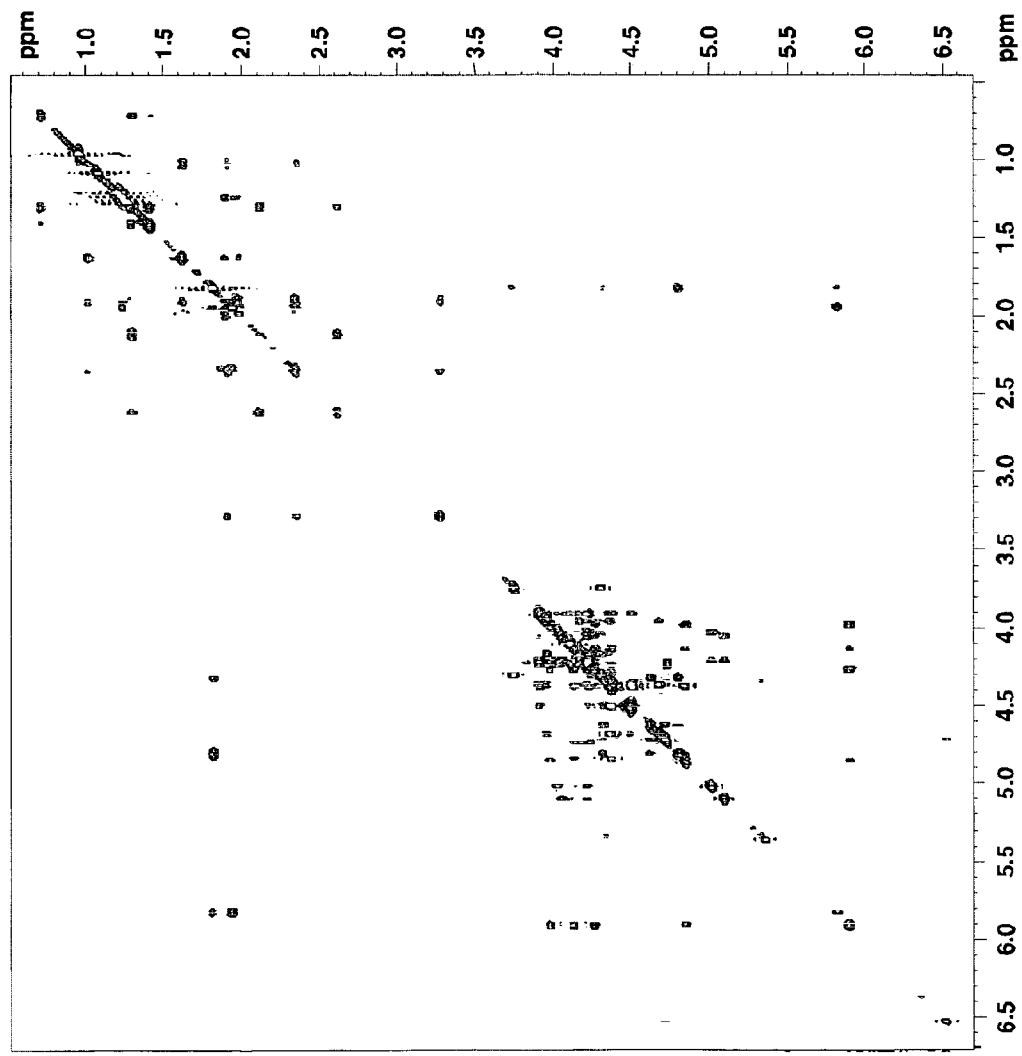

FIG. 51 shows the 2D NMR (COSY) spectrum of compound R1.

Figure 52:
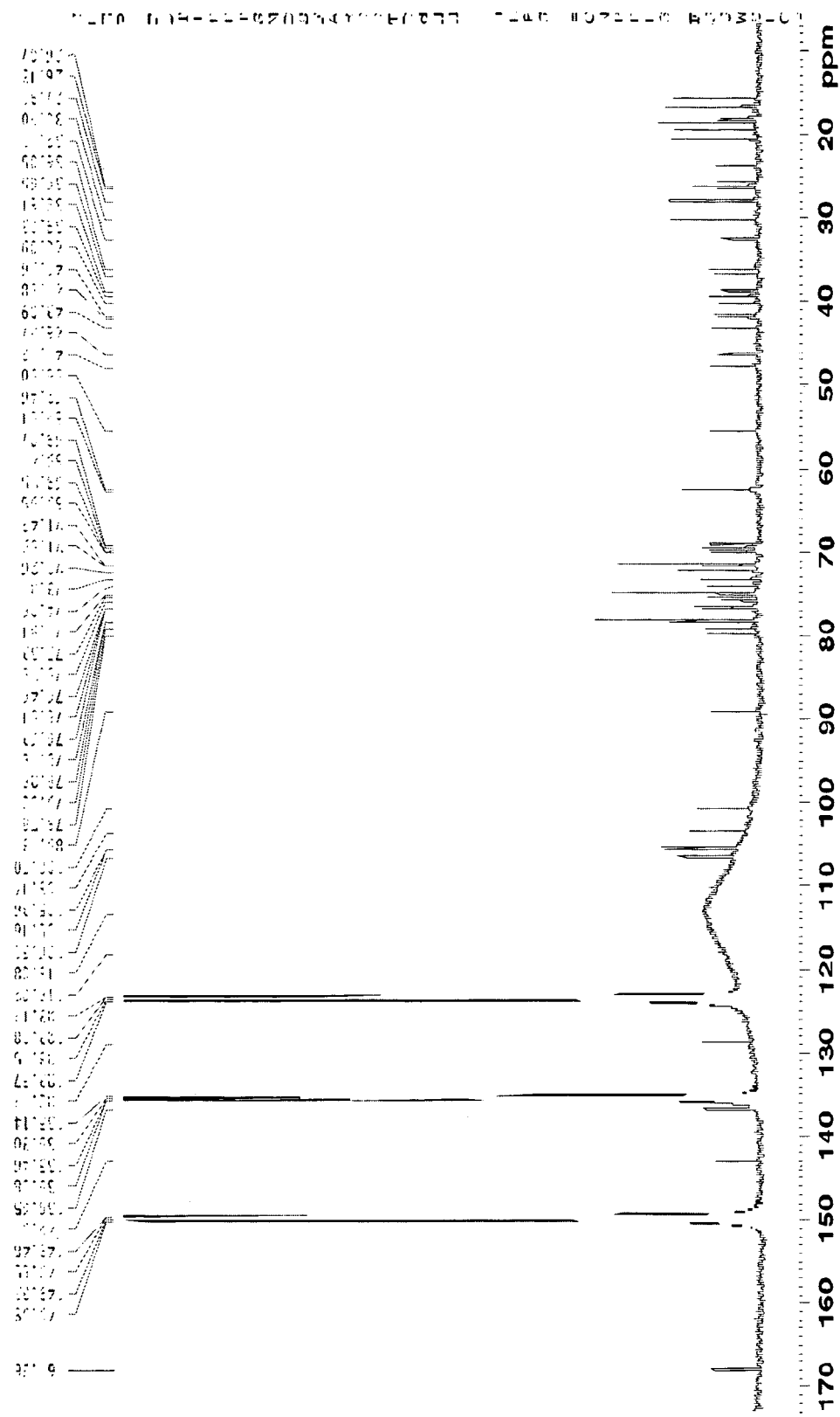

FIG. 52 shows the C13 NMR spectrum of compound R1.

Figure 53:
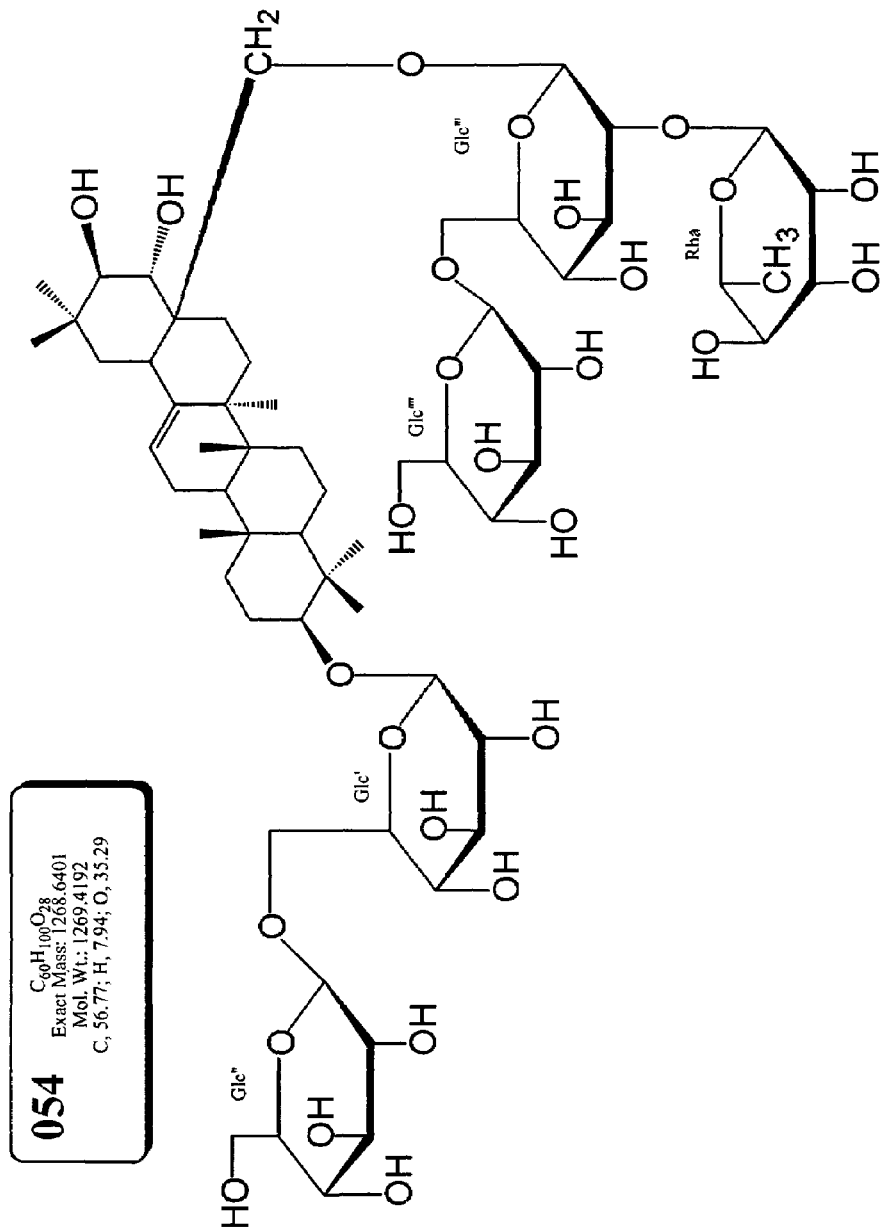

FIG. 53 shows the chemical structure of Compound O54.

Figure 54:
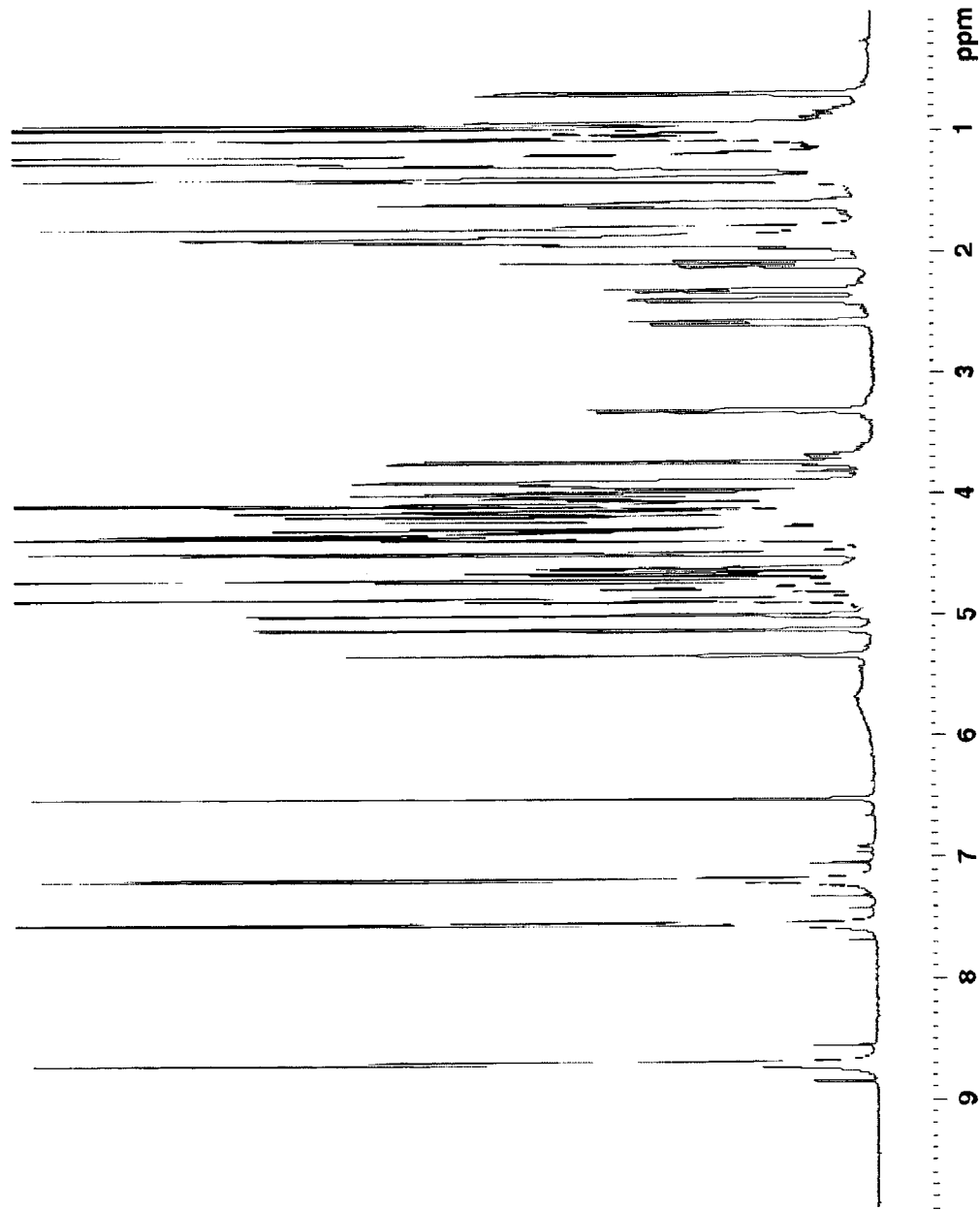

FIG. 54 shows the Proton-N MR spectra of compound O54.

Figure 55:
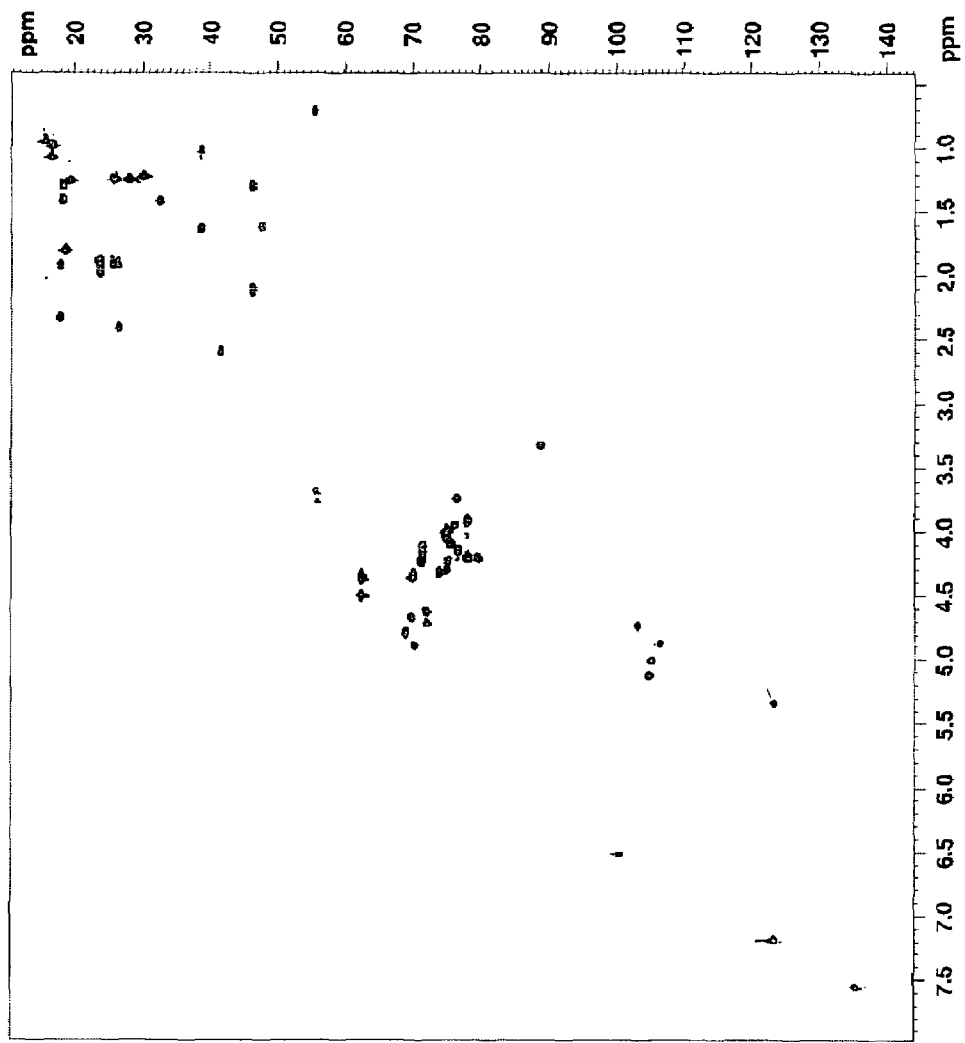

FIG. 55 shows the 2D NMR (HMQC) spectra of compound O54.

Figure 56:
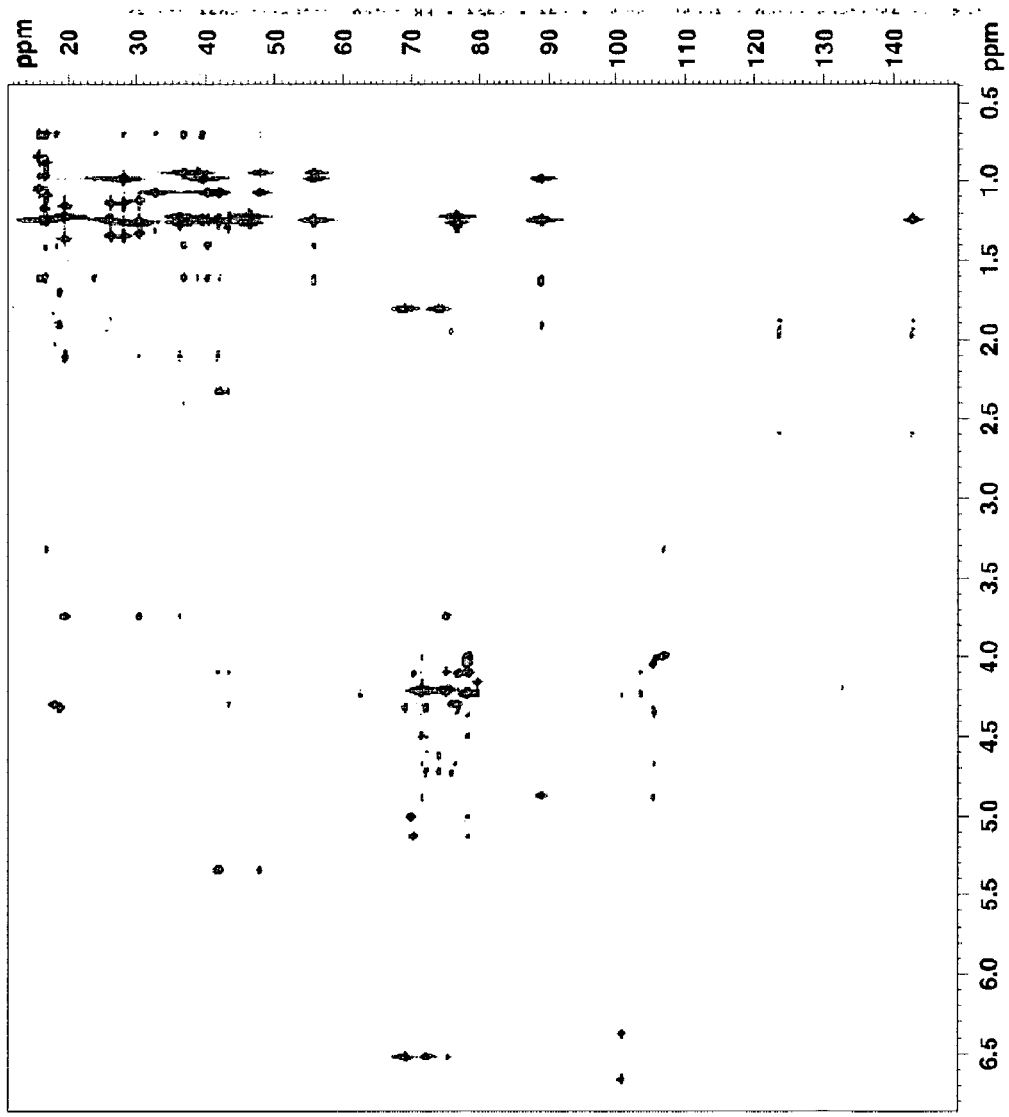

FIG. 56 shows the 2D NMR (HMBC) spectra of compound O54.

Figure 57:
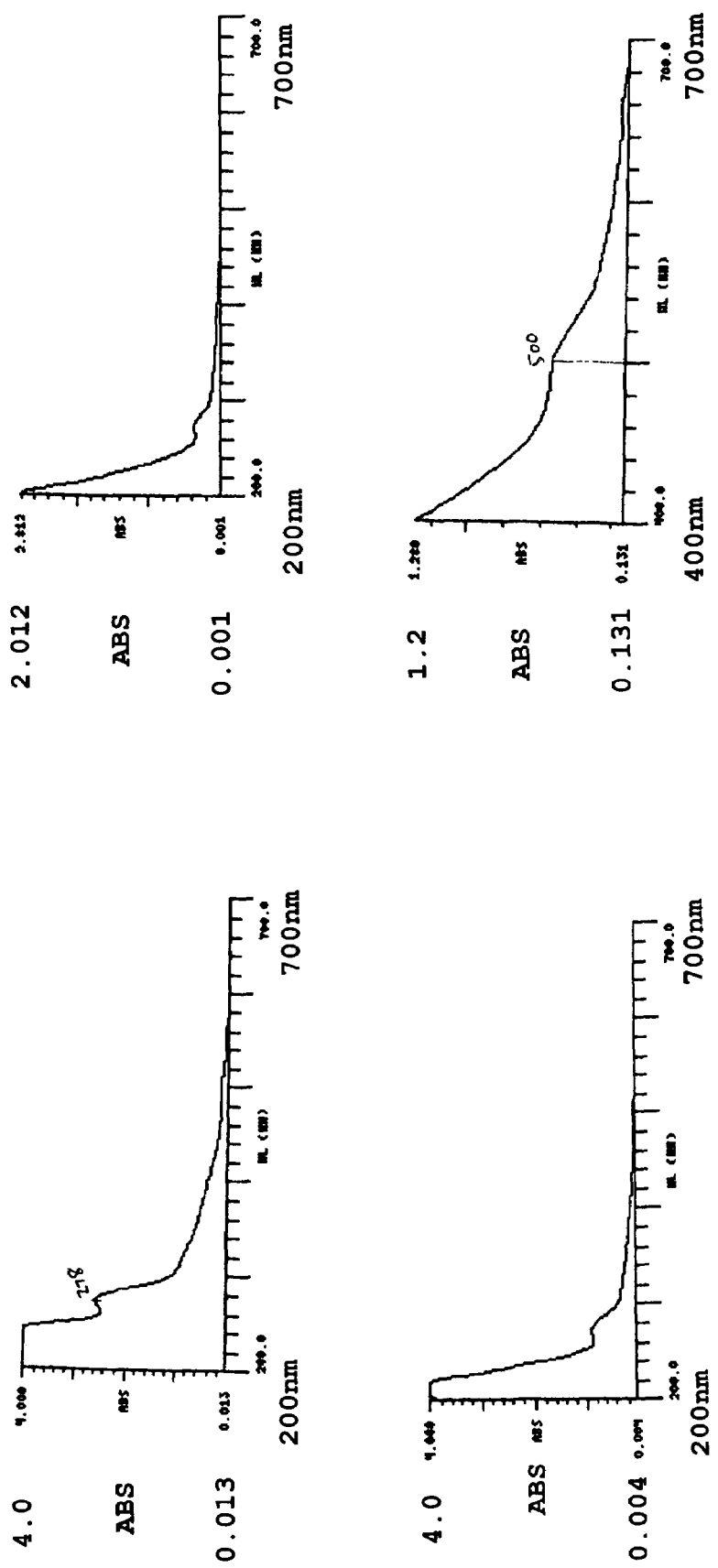

FIG. 57 shows the absorption spectrum of *Xanthoceras sorbifolia* extract. Abscissa: Wavelength in nm. Ordinate:

Optical Density. The extract has three absorption maximum at 207 nm, 278 nm and 500 nm.

Figure 58:
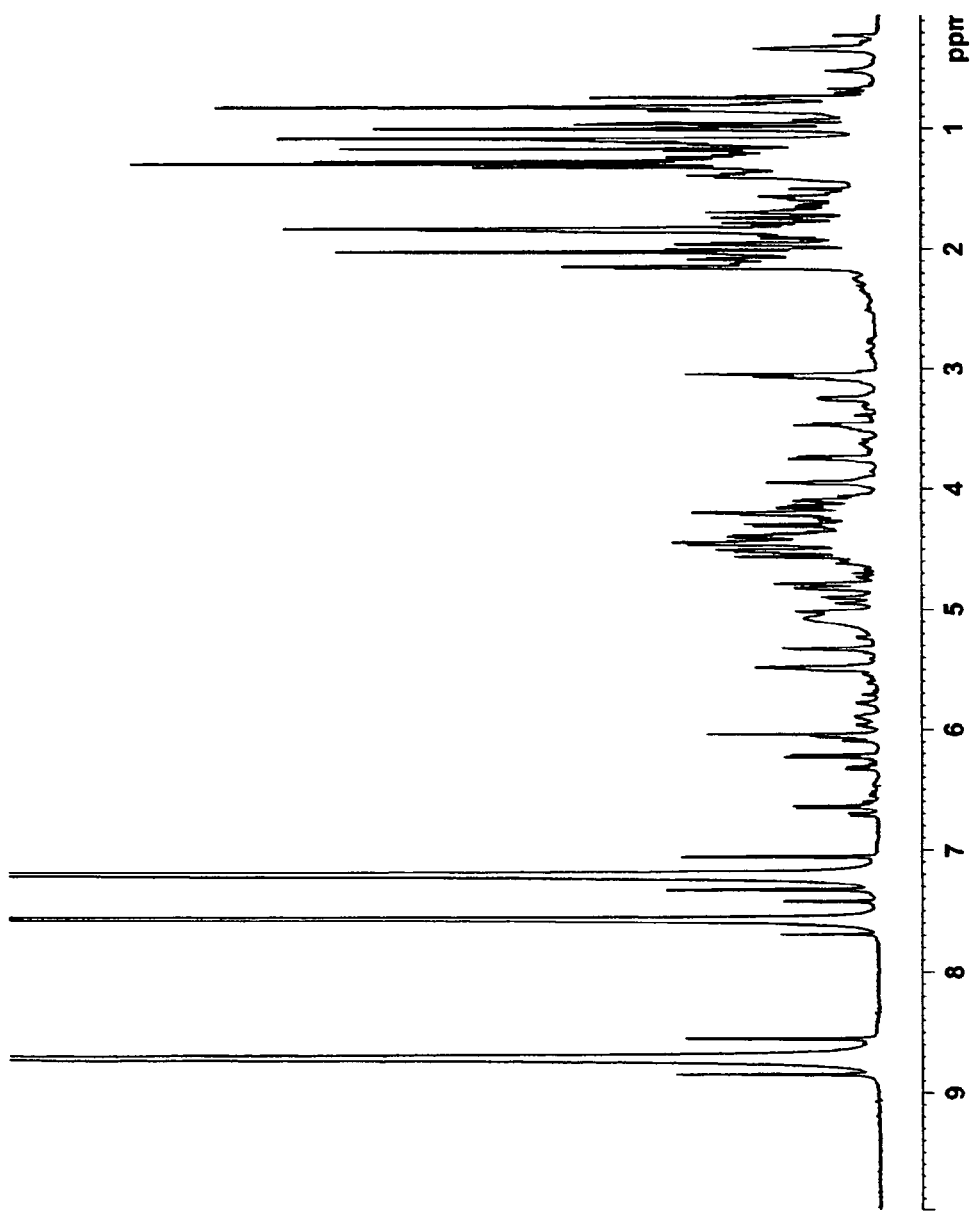

FIG. 58 shows the proton NMR spectrum of Y4.

Figure 59:
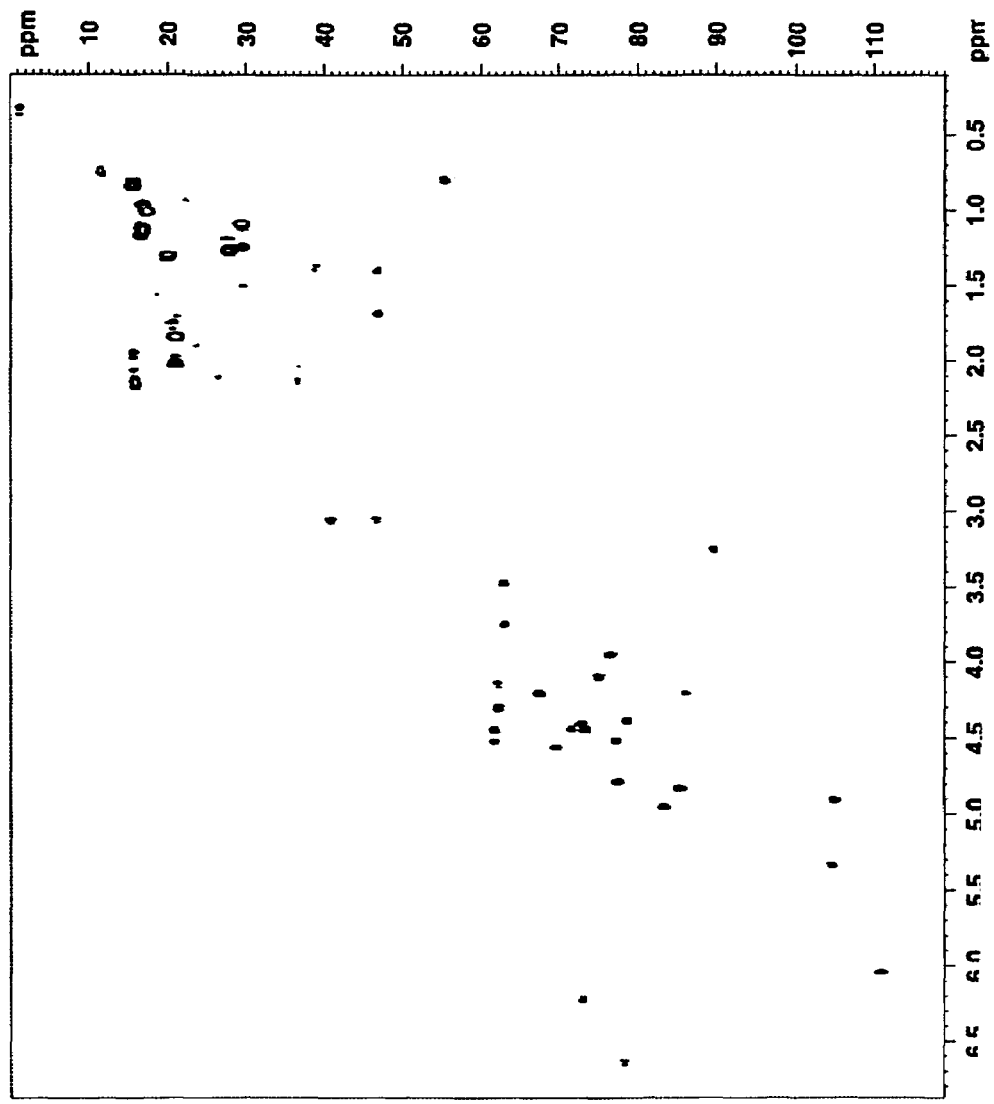

FIG. 59 shows the 2D NMR (HMQC) spectrum of Y4.

FIG. 60 shows purification of component-R with HPLC. A: Extract from fraction #10 of FPLC (iso-30) was further separated by HPLC. B: Rechromatogram of the major component under same condition as described in A.

Figure 61:
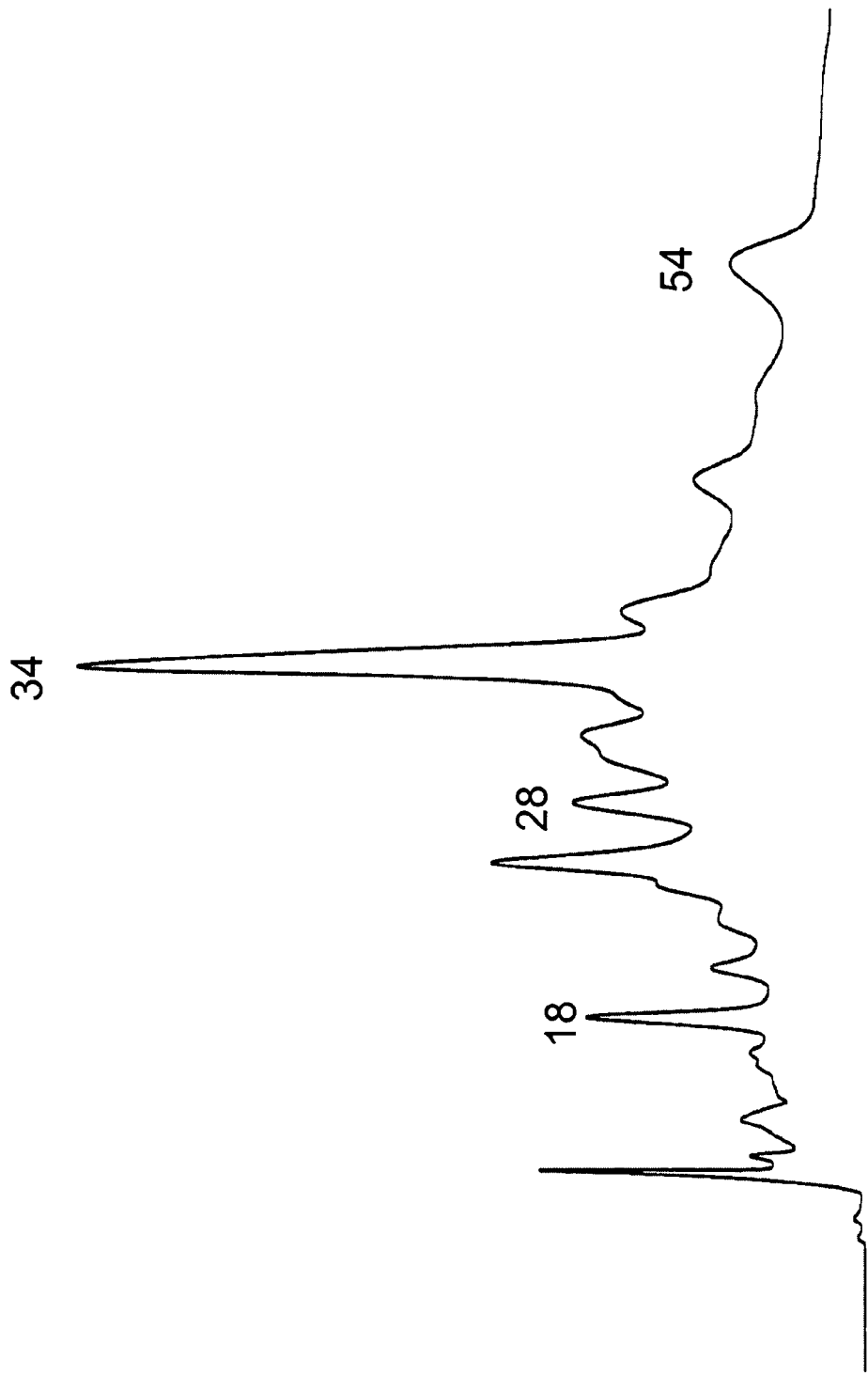

FIG. 61. Fractionation of Fraction-O with HPLC with 20% acetonitrile isocratic elution (iso-20).

Figure 62:
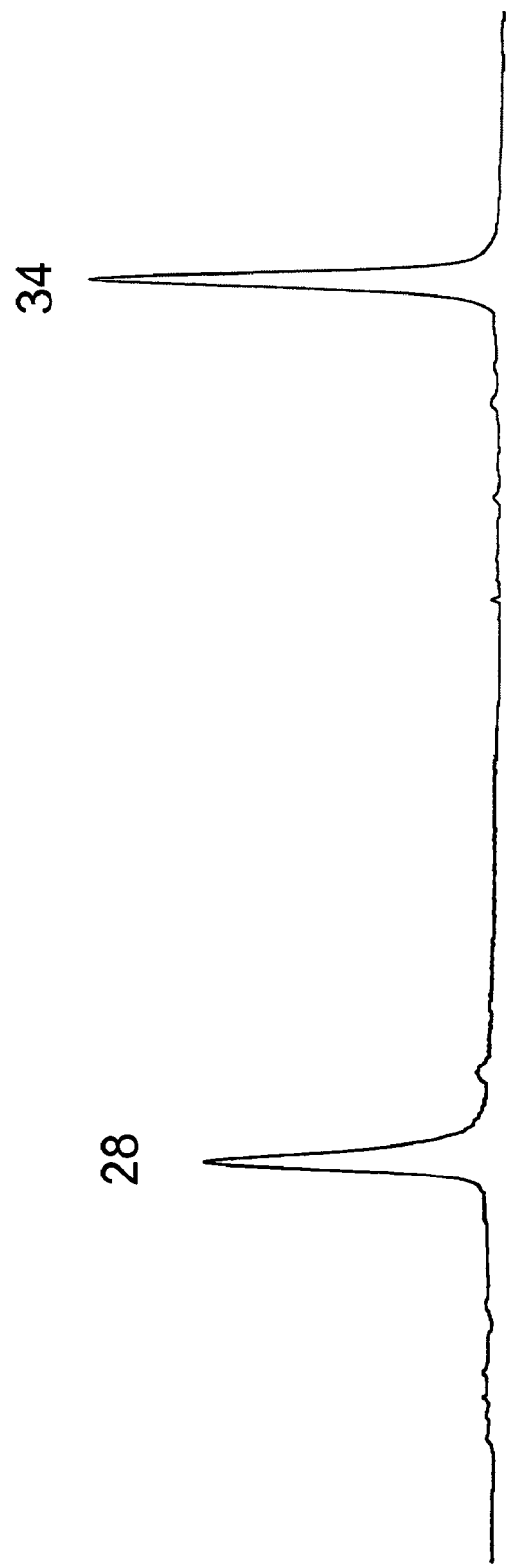

FIG. 62. Rechromatography of O28 and O34 (from iso-20).

Figure 63:
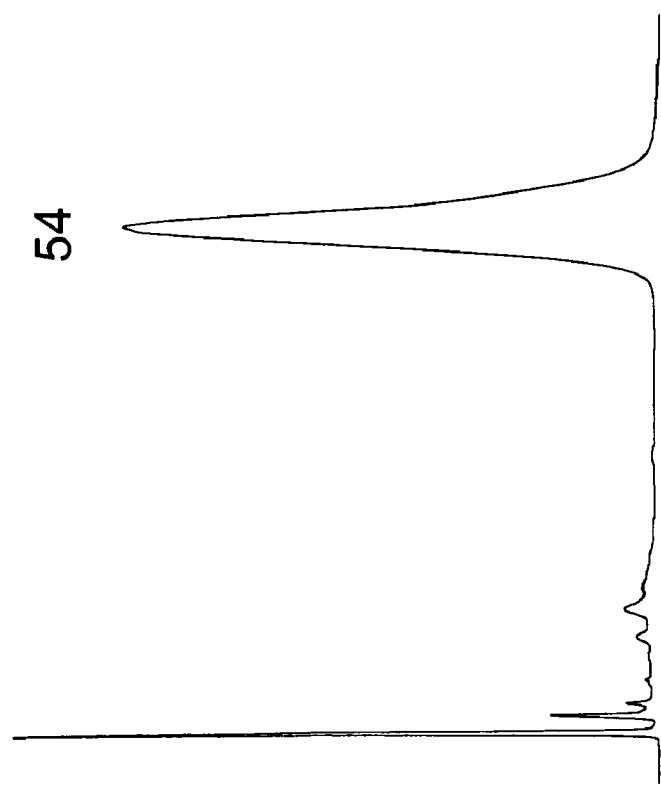

FIG. 63. Rechromatography of O54 (from iso-20).

DETAILED DESCRIPTION OF THE INVENTION

This invention provides a compound selected from a compound of formula (1):

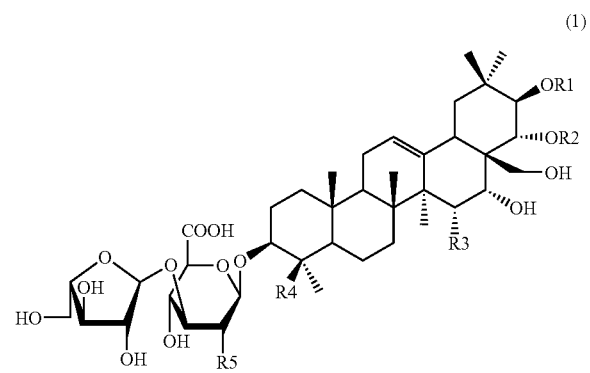

(1)

or a salt, ester or derivative thereof, wherein: R1 represents angeloyl group; R2 represents angeloyl group; R3 represents OH or H; R4 represents CH3 or CH2OH; and R5 represents D-glucose or D-Galactose.

This invention provides a compound selected from a compound of formula (2):

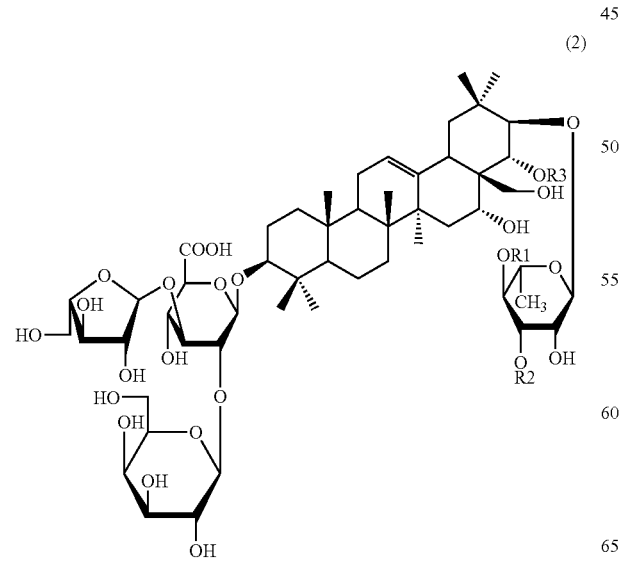

(2)

or a salt, ester or derivative thereof, wherein: R1 represents angeloyl group; R2 represents angeloyl group; and R3 represents Ac or H.

This invention provides a compound selected from a compound of formula (3):

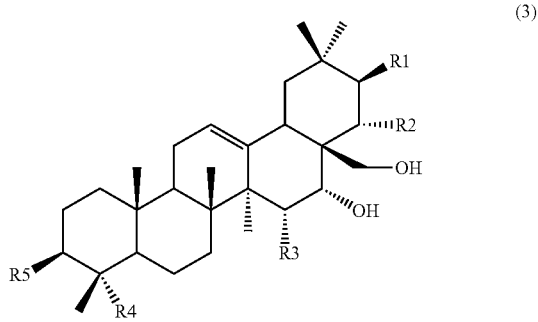

(3)

or a salt, ester or derivative thereof, wherein: R1 represents angeloyl group; R2 represents angeloyl group; R3 represents OH or H; R4 represents CH3 or CH2OH; and R5 represents sugar moiety or sugar chain selected from the group consisting of: D-glucose, D-galactose, L-rhamose, L-arabinose, D-xylose, alduronic acid, D-glucuronic acid and D-galacturonic acid.

This invention provides a compound selected from a compound of formula (4):

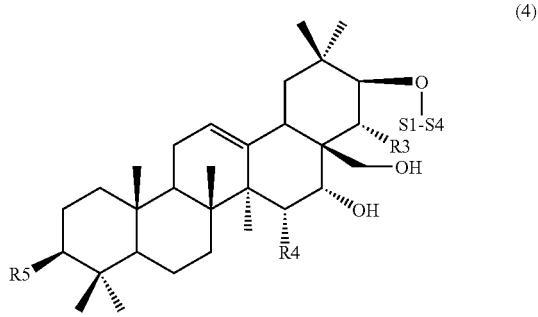

(4)

or a salt, ester or derivative thereof,

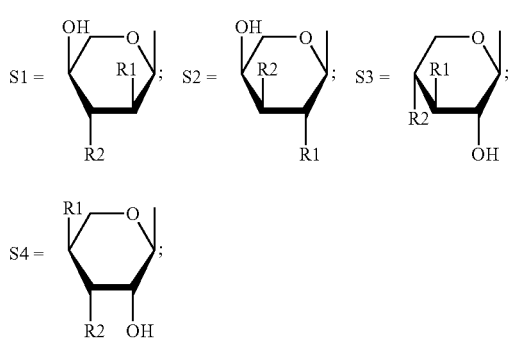

wherein:

R1 represent angeloyl group; R2 represent angeloyl group; R3 represents Ac or H; R4 represents H or OH; and R5 represents sugar moiety or sugar chain selected from the group consisting of: D-glucose, D-galactose, L-rhamnose, L-arabinose, D-xylose, alduronic acid, D-glucuronic acid and D-galacturonic acid.

In an embodiment, the angeloyl groups are in the trans-position on a planar structure.

This invention provides a compound comprising the following structure:

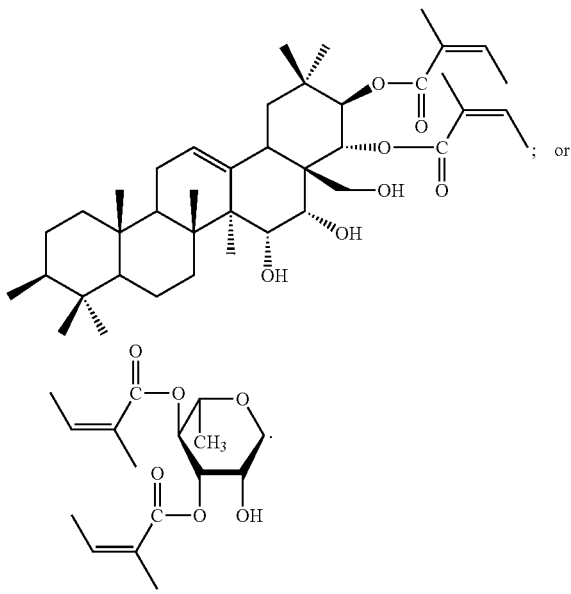

; or

This invention provides a composition for inhibiting tumor cell growth, comprising the above-described compounds. In an embodiment, the composition comprises a suitable carrier. In another embodiment, the composition comprises a pharmaceutically suitable carrier.

This invention provides a method for treating ovarian cancer in a subject, comprising administering to said subject an effective amount of the above-described compositions.

A method for isolating compounds from *Xanthoceras sorbifolia* herb or plants from the sapindaceae family comprising the steps of: (a) extracting *Xanthoceras sorbifolia* or plant powder with organic solvents to obtain an organic extract; (b) collecting the organic extract; (c) refluxing the organic extract to obtain a second extract; (d) removing the organic solvent from the second extract; (e) drying and sterilizing the second extract to obtain a crude extract powder; (f) fractionating the crude extract powder into components using HPLC and FPLC chromatography with silica gel, C18 and other equivalent solid phase materials; (g) monitoring absorption wavelength at 207 nm or 254 nm; (h) identifying the bioactive components of the crude extract powder; (i) purifying one or more bioactive components of the crude extract powder with FPLC to obtain one or more fraction of the bioactive component; and (j) isolating the desired fraction of the bioactive component with preparative HPLC.

Compound Y

This invention provides a compound comprising the following structure, i.e., see FIG. 17, with the formula of $C_{57}H_{88}O_{23}$ and the name of 3-O-[β-D-galactopyranosyl (1→2)]-α-L-arabinofuranosyl(1→3)-β-D-glucuronopyranosyl-21,22-O-diangeloyl-3β, 15α, 16α, 21β, 22α, 28-hexahydroxyolean-12-ene, also known as Xanifolia-Y. This compound was isolated from *Xanthoceras sorbifolia*.

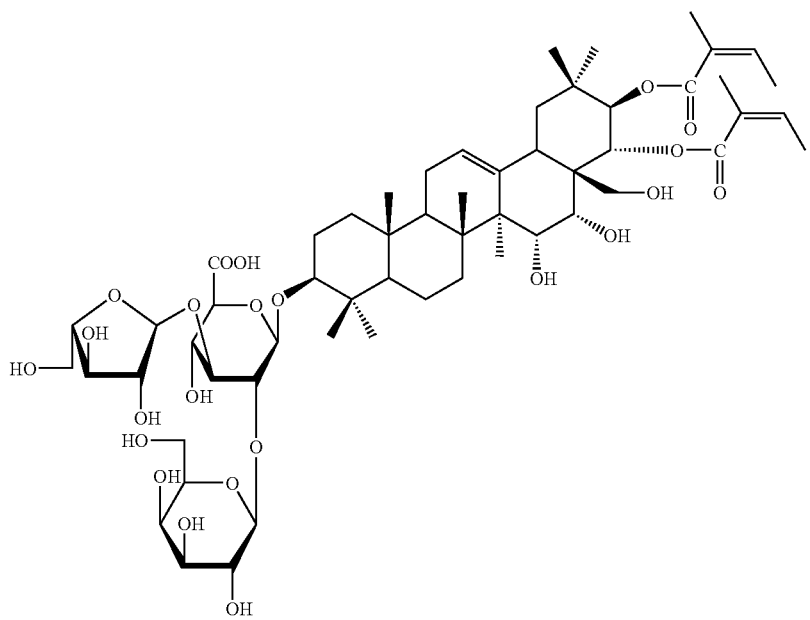

This compound belongs to an oleanene triterpenoidal saponin with a trisaccharide chain attached at C-3 of the aglycone and two angeloyl groups acylated at C-21 and C-22. This compound has anti-cancer activity.

The assignment of this structure is supported by spectral data, i.e., H-NMR, 2D NMR (HMBC, HMQC), and MS (MALDI-TOF, EMS). Accordingly, this compound has the characteristic property as shown in FIGS. 18-22 or Table 5.1.

Compound Y1

This invention provides another compound comprising the following structure, i.e., see FIG. 23, with the formula of $C_{65}H_{100}O_{27}$ and the name of 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β, 16α, 21β, 22α, 28-pentahydroxyolean-12-ene, also known as Xanifolia-Y1.

angeloyl groups were acylated at C-3 and C-4 position. This compound has anti-cancer activity.

The assignment of this structure is supported by spectral data, i.e., H-NMR, 2D NMR (HMBC, HMQC, COSY), and MS (MALDI-TOF). Accordingly, this compound has the characteristic property as shown in FIGS. 24-27.

Compound Y2

This invention provides a third compound comprising the following structure, i.e., see FIG. 28, with the formula of $C_{57}H_{88}O_{24}$ and chemical name of 3-O-[β-D-glucopyranosyl-(1→2)]-α-L-arabinofuranosyl(1→3)-β-D-glucuronopyranosyl-21,22-O-diangeloyl-3β, 15α, 16α, 21β, 22α, 24β, 28-heptahydroxyolean-12-ene, also known as Y2.

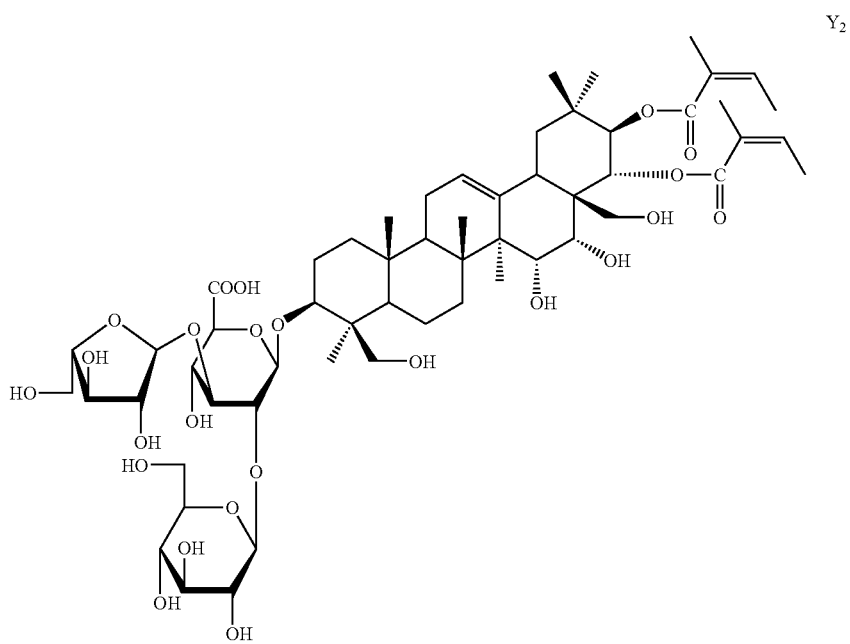

Y2

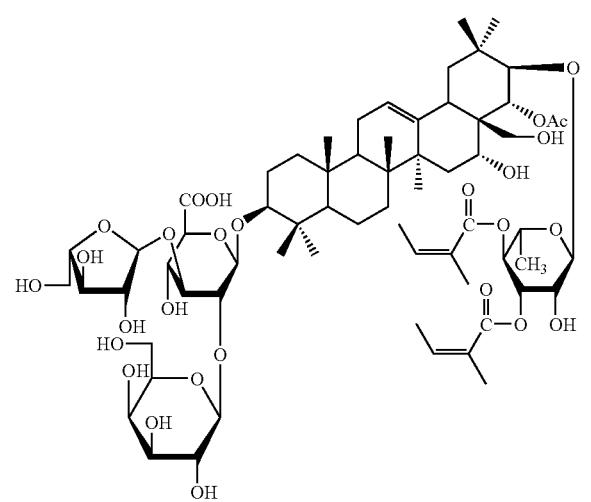

Y1

This compound is a bisdesmosidic polyhydroxyoleanene triterpenoidal saponin with a trisaccharide chain at C-3 of the backbone and a monosaccharide moiety at C-21 where two This compound (Y2) belongs to saponins comprising a triterpene, a sugar moiety and angeloyl groups linked to the backbone. The angeloyl groups are linked to the backbone at C21 and C22 positions. This compound has anti-cancer activity.

The assignment of this structure is supported by spectral data, i.e., H-NMR, C-NMR, 2D NMR (HMBC, HMQC, TOCSY), and MS (MALDI-TOF). Accordingly, this compound has the characteristic property as shown in FIGS. 29-34.

Compound Y8

This invention provides a fourth active compound Y8 and the structure was determined by 1D NMR, 2D NMR, and MS analysis. The compound comprises the following structure, i.e. see FIG. 35, with the formula of $C_{57}H_{87}O_{23}$ and chemical name of 3-O-[β-glucopyranosyl(1→2)]-α-arabinofuranosyl(1→3)-β-glucuronopyranosyl-21,22-O-diangeloyl-3β, 16α, 21β, 22α, 24β, 28-hexahydroxyolean-12-ene.

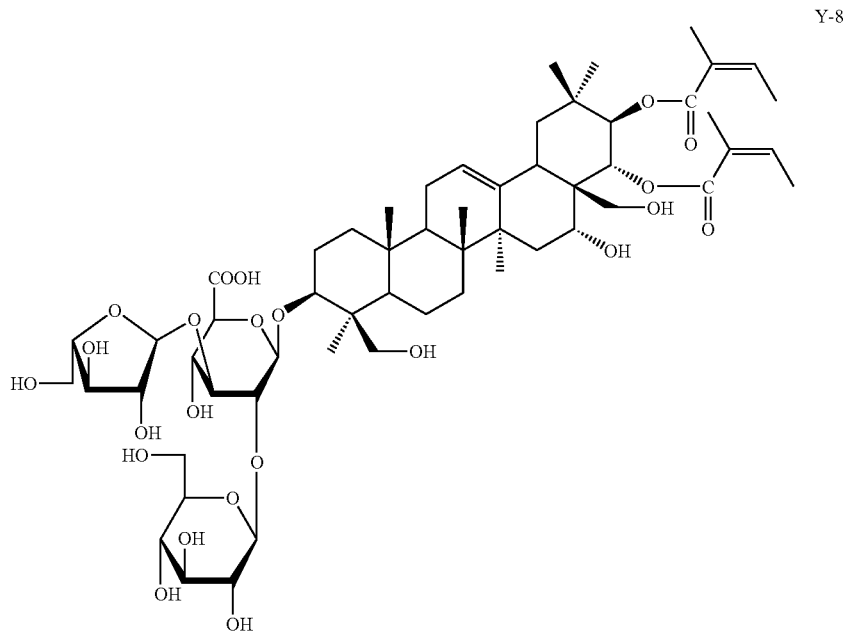

Y-8

The assignment of this structure is supported by spectral data, i.e., H-NMR, C13-NMR and 2D NMR (HMQC). Accordingly, this compound has the characteristic property as shown in FIGS. 36-38.

Compound Y9

This invention provides a fifth active compound Y9 and the structure was determined by 1D NMR, 2D NMR, and MS analysis. The compound comprises the following structure, i.e., see FIG. 39, with the formula of $C_{63}H_{98}O_{26}$ and chemical name of 3-O-[β-galactopyranosyl(1→2)]-α-arabinofuranosyl(1→3)-β-glucuronopyranosyl-21-O-(3,4-diangeloyl)-α-rhamnopyranosyl-3β, 16α, 21β, 22α, 28-pentahydroxyolean-12-ene.

The assignment of this structure is supported by spectral data, i.e., H-NMR, 2D NMR (HMQC and HMBC). Accordingly, this compound has the characteristic property as shown in FIGS. 40-42.

Compound Y10

This invention provides a sixth active compound Y10 and the structure was determined by 1D NMR, 2D NMR and MS analysis. The compound comprises the following structure, i.e., see FIG. 43, with the formula of $C_{57}H_{87}O_{22}$ and chemical name of 3-O-[β-galactopyranosyl(1→2)]-α-arabinofuranosyl(1→43)-β-glucuronopyranosyl-21,22-O-diangeloyl-3β, 16α, 21β, 22α, 28-pentahydroxyolean-12-ene.

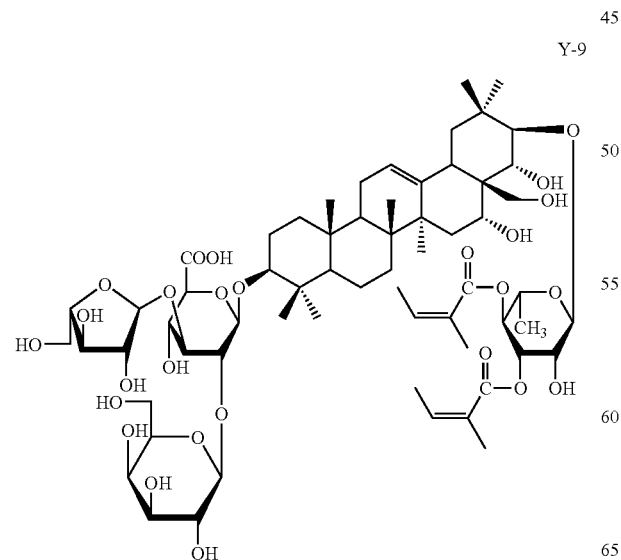

Y-9

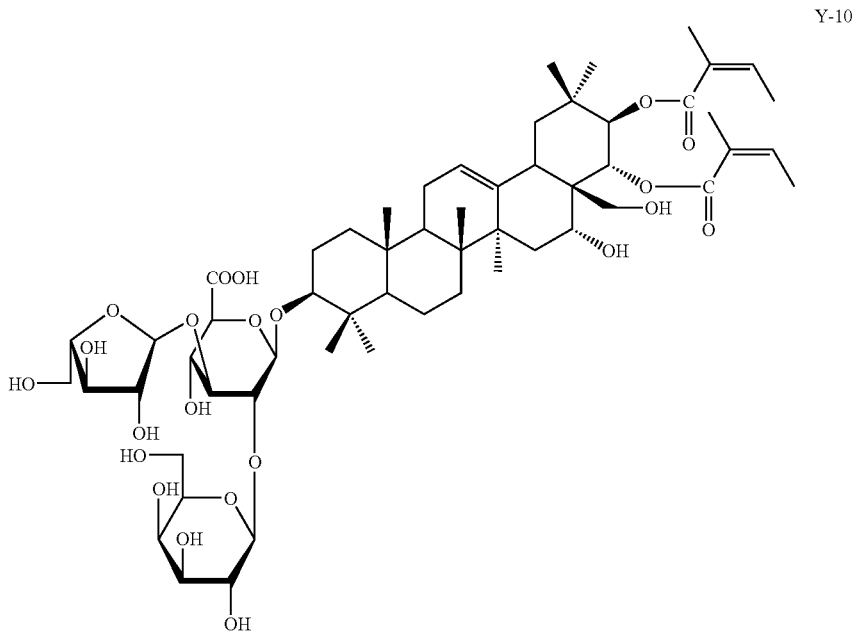

Y-10

The assignment of this structure is supported by spectral data, i.e., H-NMR, C13-NMR and 2D NMR (HMQC). Accordingly, this compound has the characteristic property as shown in FIGS. 44-46.

This invention provides a compound comprising a sugar and a triterpene or Sapogenin, wherein the triterpene or sapogenin is acylated at Carbon 21 and 22 with Angeloyl groups. In an embodiment, the compound comprises one or more sugars.

This invention shows that extracts of *Xanthoceras sorbifolia* have anticancer activity. The experiments for determining the anti-cancer activity employ human cells lines derived from eleven human organs (HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain) and OVCAR-3 (ovary)). Among the 11 cell lines studies, their sensitivity toward *Xanthoceras sorbifolia* extract can be divided into four groups: (A) most sensitive: Ovary, see FIG. 14; (B) Sensitive: bladder, bone, (C) Srmi-sensitive: prostate, leukocyte, liver, breast, and brain; and (D) lease sensitive: colon, cervix, and lung. See FIG. 16A-D. Their IC50 values are listed in Table 3.1.

TABLE 3.1

IC50 values of Xanthoceras Sorbifolia Extract Determined in Different Cancer Cells

| Cancer cells from different organs | IC50 determined by MTT assay (ug/ml) |
| --- | --- |
| Ovary (most sensitive) | 15-15 |
| Bladder (sensitive) | 45-50 |
| Bone | 40-55 |
| Prostate (semi-sensitive) | 40-50 |
| Leukocyte | 45-50 |
| Liver | 45-65 |
| Breast | 65 |
| Brain | 70-85 |
| Colon (least sensitive) | 90 |
| Cervix | 115 |
| Lung | 110 |

In order to identify the active compounds of *Xanthoceras sorbifolia*, the extracts from *Xanthoceras sorbifolia* were separated by chromatography comprising FPLC (Fast Protein Liquid Chromatography) and HPLC (High Preferment Liquid Chromatography). Multiple fractions were obtained by FPLC procedures, i.e., see FIG. 9 and HPLC, i.e., see FIG. 8. Analysis of the fractions by HPLC shows that the extract comprises 26 identifiable fractions, designated as a to z, which are shown in FIG. 8.

Anti-cancer activities of these fractions were determined by the MTT assay. FPLC fraction 5962, i.e., see FIG. 10, which coresponding to fraction Y in HPLC, i.e., see FIG. 8, has the anti-cancer activity. Fraction 5962 was further separated into 4 components Y1 to Y4, i.e., see FIG. 11. Fraction 6365 was further seperated into 5-6 components, designated as Y5-Y10. See FIG. 12. The compounds Y or Y3, Y1 and Y2 show strong anti-tumor activity, i.e., see FIG. 2-3, and were therefore isolated. Similarly, compounds Y8, Y9 and Y10 also show strong anti-tumor activity, i.e., see FIG. 4, and were therefore purified. See FIG. 13.

The structures of these active compounds, i.e., Y, Y1, Y2, Y8, Y9 and Y10 and their uses are the subject of this application.

The inhibition effects of the compounds of the present invention on ovarian cancer cells were evaluated with the MTT assay. Compound Y shows at least 10 times higher potency (IC50=1.5 ug/ml), i.e., see FIG. 2, than the original crude extract as shown in FIG. 14 (IC50=20 ug/ml).

The selectivity of compound Y toward different cell lines was tested, and it was found that compound Y has a much higher potency toward ovarian cancer cells as compared to the cervical cancer cells. See FIG. 15.

This invention provides a method for identifying and isolating the active compounds from plants, herbs or plant extracts. In an embodiement, the extracts include extracts of *Xanthoceras sorbifolia* or of plants from the sapindaceae family.

This invention provides the chemical structures of six active compounds obtainable from *Xanthoceras sorbifolia* or of plants from the sapindaceae family. The compounds are shown in FIG. 1.

This invention provides spectral data including H-NMR, C-13-NMR, 2D NMR (HMBC, HMQC, COSY, TOCSY), and MS (MALDI-TOF, ESI-MS) in supporting the assigned structures.

This invention provides a consensus sub-structure or functional group from the active compounds purified from fraction Y. The compounds, such as Y or Y3, Y1, Y2, Y8, Y9 and Y10, obtainable from fraction Y are collectively referred to as "Ys". The consensus sub-structure or functional group of these compounds is the biangeloyl groups located on adjacent carbons. For example, in compound Y, Y2, Y8 and Y10, the biangeloyl are located at 21β and 22α of the triterpene backbone. See FIG. 5. In compound Y1 and Y9, the biangeloyl groups are located at C3 and C4 of the sugar ring. See FIG. 6. Accordingly, the biangeloyl groups of these active compounds are situated in trans-position with respect to each other on a planar structure. See FIG. 7.

The results of this invention indicate the active functional group of these compounds is a biangeloyl group attached in-trans to adjacent carbons located in a planar structure. See FIG. 7.

This invention provides a salt of the above-described compounds.

This invention provides a composition comprising the above-described compounds and a suitable carrier.

This invention provides a pharmaceutical composition comprising an effective amount of the above-described compounds and a pharmaceutically acceptable carrier.

This invention provides an anti-ovarian cancer agent or composition comprising the above-described compositions.

This invention provides a composition effective against cancer growth. The cancer includes but is not limited to bladder cancer, bone cancer and ovary cancer.

This invention provides a composition comprising the above-described compounds and their salts, esters, derivatives or metabolites capable of inhibiting tumour growth.

This invention provides a composition comprising the above-described compounds and their salts, esters, derivatives or metabolites capable of inhibiting virus growth and/or activities.

In addition to the compound Ys, other compounds were also purified from fraction R and fraction O of the extract of *Xanthoceras sorbifolia*, which are designated herein as R1 and O54, respectively. Their structures were determined. Preliminary experiments indicate both R1 and O54 do not have anticancer activity.

Compound R1

The structure of Compound R1 shown below and in FIG. 47, has a chemical formula of $C_{65}H_{106}O_{29}$ and chemical name of 3-O-[angeloyl-(1→3)-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β, 21β, 22α, 28-tetrahydroxyolean-12-ene, also known as Xanifolia-R1.

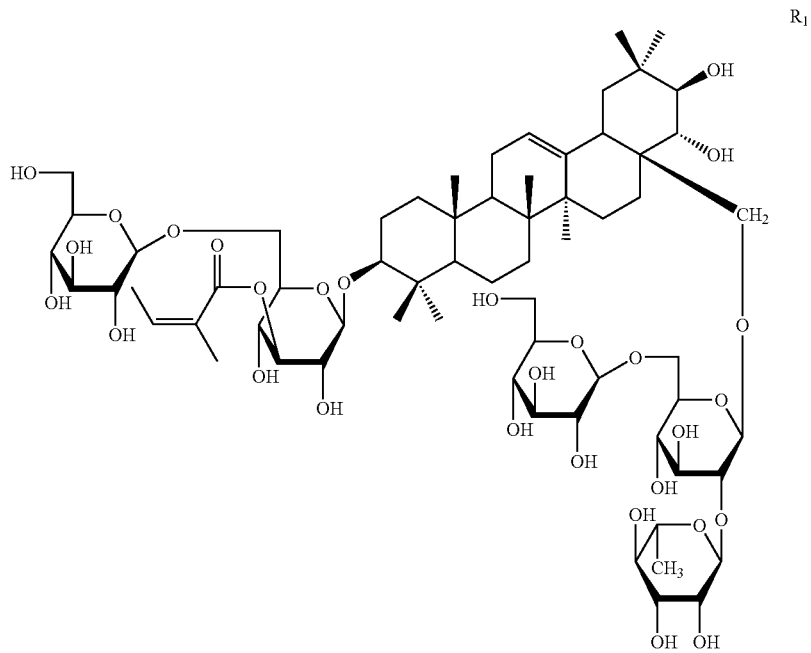

The assignment of this structure is supported by spectral data, i.e., H-NMR, C-13-NMR, 2D NMR (HMBC, HMQC, COSY), and MS (MALDI-TOF, EMS). Accordingly, this compound has the characteristic property as shown in FIGS. 48-52.

Compound-O54

This invention provides a compound O54 purified from the extract of *Xanthoceras sorbifolia*. The structure of O54 was determined and has a formula of $C_{60}H_{100}O_{28}$.

The Structure of Compound O54 is shown below, i.e., see FIG. 53:

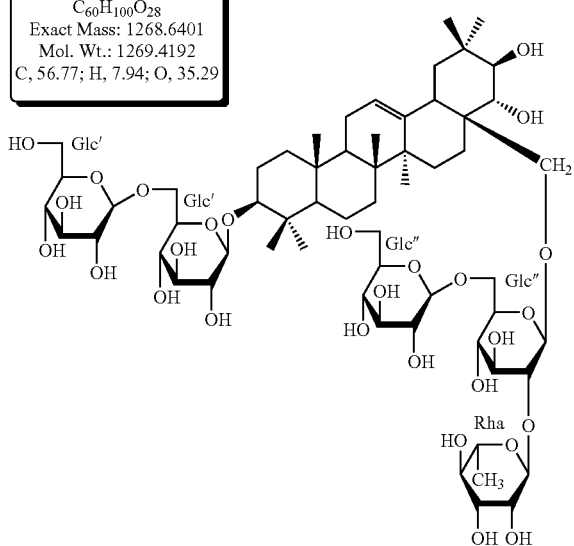

The chemical name of compound-O54 is: 3-O-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β, 21β, 22α, 28-tetrahydroxyolean-12-ene.

The assignment of this structure is supported by spectral data, i.e., 1H-NMR, 2D NMR (HMBC, HMQC). Accordingly, this compound has the characteristic property as shown in FIGS. 54-56.

SUMMARY

This invention provides methods for identifying and purifying compounds from the plant extract of *Xanthoceras sorbifolia*. Six compounds have been identified and purified, and have been shown to have anticancer activity. These compounds are collectively referred to as triterpenoidal saponins. A consensus sub-structure is identified from these active compounds. A consensus sub-structure or active functional groups of these compounds is the biangeloyl groups located on adjacent carbons. The biangeloyl groups are located at 21β and 22α of the triterpene backbone, i.e., see FIG. 5, or located at C3 and C4 of the sugar ring, i.e., see FIG. 6. Accordingly, the biangeloyl groups of these active compounds are situated in trans-position in respect to each other on a planar structure. See FIG. 7. The structures or derivatives of the compounds of the present invention are also obtainable by chemical systhesis or from biological sources.

This invention will be better understood from examples which follow. However, one skilled in the art will readily appreciate that the specific methods and results discussed are merely illustrative of the invention as described more fully in the claims which follow thereafter.

EXPERIMENTAL DETAILS

Experiment 1

Herb Extraction (a) extracting *Xanthoceras sorbifolia* powder of husks or branches or stems or leaves or kernels or roots or barks with organic solvent at ratio of 1:2 for 4-5 times for 20-35 hours each time to form an organic extract; (b) collecting the organic extract; (c) refluxing the organic extract for 2-3 times at 80° C. to form second extracts; (d) removing the organic solvent from the second extract; and (e) drying and sterilizing the extract to form a *Xanthoceras sorbifolia* extract powder.

Experiment 2

Analysis of *Xanthoceras Sorbifolia* Extract Components by HPLC Chromatography

Methods

HPLC. A C-18 reverse phase μbondapak column (Water P/N 27324) was equilibrated with 10% acetonitrile, 0.005% Trifluoroacetic acid (equilibration solution). An extract of *Xanthoceras sorbifolia* prepared using the methods described in Experiment 1 was dissolved in equilibration solution (1 mg/ml) before applying into the column. 20 ug of samples was applied into column. Elution conditions: Fractions were eluted (with flow rate 0.5 ml/min.) with acetonitrile gradient from 10% to 80% in 70 min, and then remains at 80% for 10 min. The acetonitrile concentration then decreased to 10% and remained at 10% for 25 min. The fractions were monitored at 207 nm and recorded in chart with a chart speed of 0.25 cm/min and with OD full scale of 0.128.

Instruments. Waters Model 510 Solvent Delivery System; Waters 484 tunable Absorbance Detector; Waters 745/745B Data Module.

Absorbance analysis. The absorption profile of *Xanthoceras Sorbifolia* extract at various wavelengths was determined. An extract of *Xanthoceras sorbifolia* of the present invention was dissolved in 10% acetonitrile/TFA and scanned at 200-700 nm with a spectrophotometer [Spectronic Ins. Model Gene Sys2].

Results

HPLC. About 60-70 peaks can be accounted for in the profile. Among them four are major peaks, 10 are of medium size and the rest are small fractions. The peaks are labelled with a to z following increased concentration of acetonitrile elution. See FIG. 8.

Absorption maximum. Three absorption maximum were identified for *Xanthoceras sorbifolia* plant extract; 207 nm, 278 nm and 500 nm. See FIG. 57.

Experiment 3

Determination of the Cell-Growth Activity Effected by *Xanthoceras Sorbifolia* Extract with Cancer Cells Derived from Different Human Organs using MTT Assay Methods and Materials Cells. Human cancer cell lines were obtained from American Type Culture Collection: HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain) and OVCAR-3 (ovary). Cells were grown in culture medium (HeLa-S3, DU145, MCF-7, HepG2 and T98G in MEN (Earle's salts); HTB-9, H460, K562, OVCAR-3 in RPMI1640; HCT-116, U2OS in McCoy-5A) supplemented with 10% fetal calf serum, glutamine and antibiotics in a 5% CO2 humidified incubator at 37° C.

MTT assay. The procedure for MTT assay followed the method described in (Carmichael et al., 1987) with only minor modifications. Cells were seeded into a 96-wells plate at concentrations of 10,000/well (HTB-9, HeLa, H460, HCT116, T98G, OVCAR-3), 15,000/well (DU145, MCF-7, HepG2, U2OS), or 40,000/well (K562), for 24 hours before drug-treatment. Cells were then exposed to drugs for 48 hours (72 hours for HepG2, U2OS, and 96 hours for MCF-7). After the drug-treatment, MTT (0.5 mg/ml) was added to cultures for an hour. The formation of formazan (product of the reduction of tetrazolium by viable cells) was dissolved with DMSO and the O.D. at 490 nm was measured by an ELISA reader [Dynatech. Model MR700]. The MTT level of cells before drug-treatment was also measured (T0). The % cell-growth (% G) is calculated as:

$$\% \ G = (TD-T0/TC-T0) \times 100 \quad (1)$$

where TC or TD represent O.D. readings of control or drug-treated cells. When T0>TD, then the cytotoxicity (LC) expressed as % of the control is calculated as:

$$\% \ LC = (TD-T0/T0) \times 100. \quad (2)$$

Results

Among the 11 cell lines studies, inhibition of cell-grwoth after exposure of plant extract was observed. However, their sensitivity toward *Xanthoceras sorbifolia* extract is different. It can be divided into four groups: Most sensitive, i.e., Ovary; Sensitive, i.e., bladder, bone; Semi-sensitive, i.e., prostate, leukocyte, liver, breast, and brain; and Least sensitive, i.e., colon, cervix, and lung. See FIGS. 14, 15 and 16A-D. Their IC50 values are listed in Table 3.1.

TABLE 3.1

IC50 values of Xanthoceras Sorbifolia Extract Determined in Different Cancer Cells

| Cancer cells from different organs | IC50 determined by MTT assay (ug/ml) |
| --- | --- |
| Ovary (most sensitive) | 15-15 |
| Bladder (sensitive) | 45-50 |
| Bone | 40-55 |
| Prostate (Semi-sensitive) | 40-50 |
| Leukocyte | 45-50 |
| Liver | 45-65 |
| Breast | 65 |
| Brain | 70-85 |
| Colon (least sensitive) | 90 |
| Cervix | 115 |
| Lung | 110 |

In addition to cell-growth inhibition, the *Xanthoceras sorbifolia* plant extract also stimulate a minor cell growth at low concentrations in bladder, bone and lung cells.

Results indicate that there is a cell or tissue stimulation component(s) in the extract. See FIGS. 16A and 16D.

To investigate the inhibition components of the *Xanthoceras sorbifolia* plant extract, the plant extract was fractionated. FIG. 10 shows the results of the screening of fractions obtained after FPLC chromatography for cell growth-inhibition activity. The assay was conducted with bladder cells. The fractions obtained from FPLC, as shown in FIG. 9, were used. As shown in FIG. 9, different components of *Xanthoceras sorbifolia* extracts cause either growth or inhibition effects on cells. Only fractions 5962, designated as Fraction Y, cause cell growth inhibition. Abscissa: concentration (ug/ml). Ordinate: % Cell Growth (determined by MTT assay).

Experiment 4

Purification of the Inhibition Components in the *Xanthoceras Sorbifolia* Extract.

(A) Fractionation of Plant Extracts with FPLC

Methods

Column. Octadecyl functionalized silica gel. Column dimension: 2 cm×28 cm; equilibrated with 10% acetonitrile—0.005% TFA before use.

Sample loading: 1-2 ml, concentration: 100 mg/ml in 10% acetonitrile/TFA.

Gradient elution condition: 10-80% acetonitrile in a total volume of 500 ml.

Monitor absorption wavelength: at 254 nm.

Fraction Collector: 5 ml/fractions (collect from 10% to 72% acetonitrile)

Instrument: AKTA-FPLC, P920 pump; Monitor UPC-900; Frac-900.

Results

The elution profile of the chromatography shows 4-5 broad fractions. See FIG. 9. These fractions were analyzed with HPLC. Specific components, corresponding to a-z as specified in FIG. 8, are then assigned in these FPLC fractions. FPLC fractions are then grouped into 7 pools and analyzed for cell growth activity in bladder cells with MTT assay. See Experiment 3. It was found that only pool #5962, corresponding to fraction Y in HPLC, contains inhibition activity. See FIG. 10. It was also found in later experiments that fractions beyond 62 also show inhibition activity. The components isolated from fractions 63-65 showed inhibition activities. See FIGS. 4, 12 and 13.

(B) Isolation of Component Ys with Preparative HPLC

Methods

Column: A preparative HPLC column (Waters Delta Pak C18-300A);

Elution conditions: 45% acetonitrile isocratic elution with flow rate of 1 ml/min.

Fractions are monitored at 207 nm and were collected and lyophilized.

Results

Final separation of Y fractions was achieved by HPLC with a preparative column. See FIGS. 11 and 12. These fractions, which include compound Y1, Y2, Y or Y3 and Y4, were collected. Re-chromatography of compound Y showed a single peak in HPLC with a C18 reverse phase column. See FIGS. 11A and 11B. Re-chromatography of the compound Y8, Y9 and Y10 showed a single peak in HPLC with a C18 reverse phase column. See FIG. 13.

(C) Appearance and Solubility

The pure compound Ys is an amorphous white powder, soluble in aqueous alcohol, i.e., methanol or ethanol, 50% acetonitrile and 100% pyridine.

(D) Inhibition Analysis of Compound Ys with MTT Assay

Inhibition analysis of compound Y was determined with MTT assay. FIG. 2 shows that compound Y has activity against ovarian cancer cells (OCAR-3) with IC50 value of 1.5 ug/ml which is 10-15 times more potent than the unpurified extract shown in FIG. 14.

Figure 3:
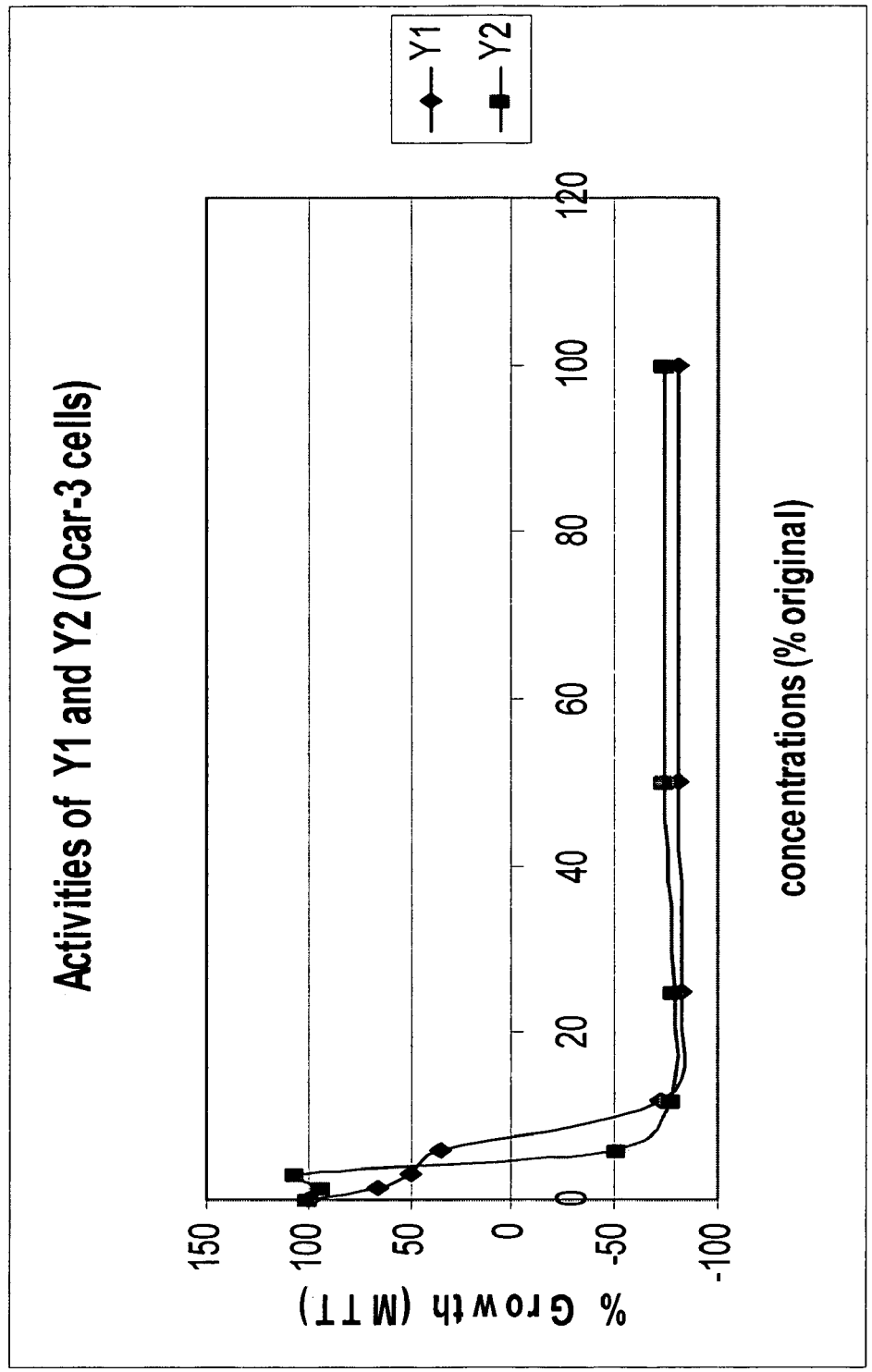
FIG. 3 shows the inhibition of the purified Compound Y1 and Compound Y2 on ovarian cancer cells' growth.
Figure 4:
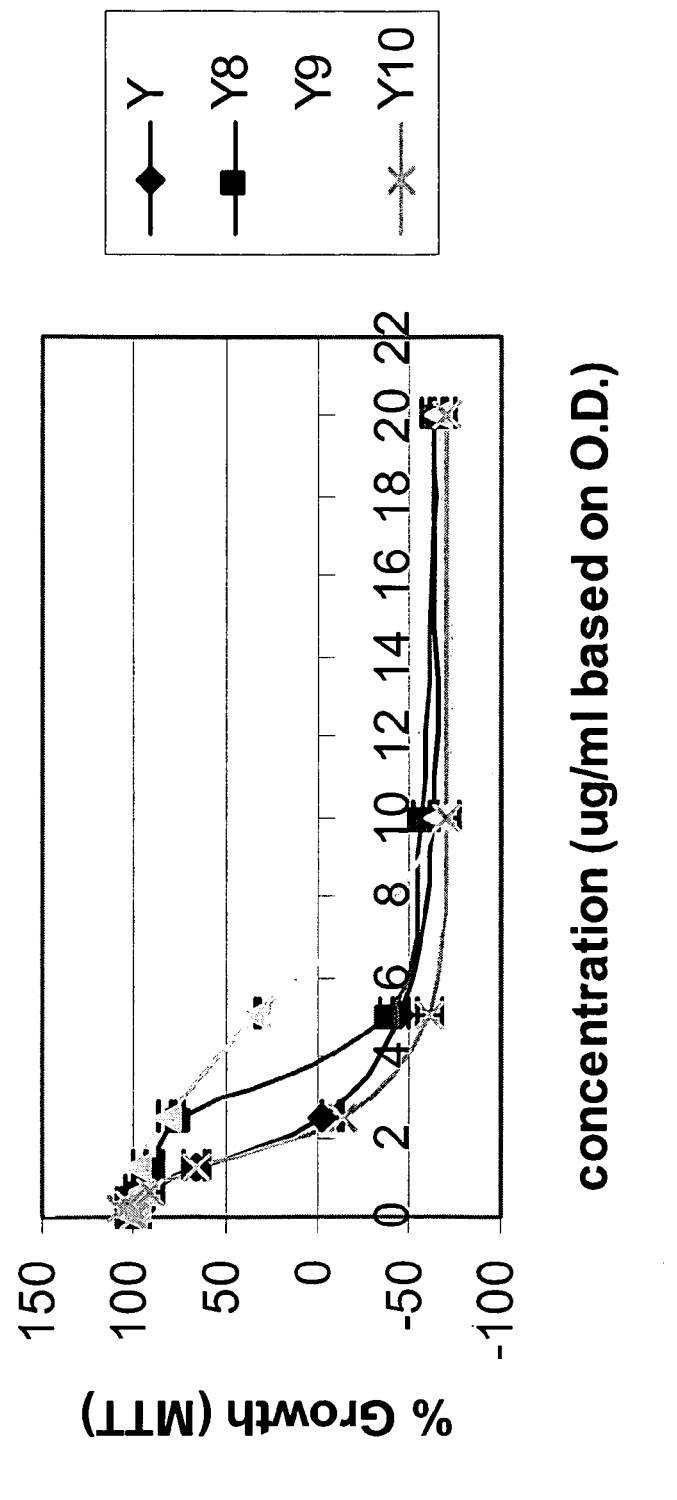
FIG. 4 shows the anticancer activity of Y, Y8, Y9 and Y10 with ovarian cancer cells determined by MTT assay.

FIG. 15 shows the selectivity of compound Y to ovarian cancer cells compared with cervical cancer cells (HeLa). FIG. 3 shows the inhibition activities of compound Y1 and Y2 on the growth of ovarian cancer cells (OCAR-3). FIG. 4 shows the inhibition activities of compound Y, Y8, Y9 and Y10 on the growth of ovarian cancer cells (OCAR-3).

Experiment 5

Determination of the Chemical Structure

Methods

NMR analysis. The pure compound Y of *Xanthoceras sorbifolia* was dissolved in pyridine-D5 with 0.05% v/v TMS. All NMR spectra were acquired using a Bruker Avance 600 MHz NMR spectrometer with a QXI probe (1H/13C/15N/31P) at 298 K. The numbers of scans for 1D 1H spectra were 16 to 128, depending on the sample concentration. 2D HMQC spectra were recorded with spectral widths of 6000× 24,000 Hz and data points of 2024×256 for t2 and t1 dimensions, respectively. The number of scans were 4 to 128. 2D HMBC were acquired with spectral widths of 6000×30,000 Hz and data points of 2024×512 for t2 and t1 dimensions, respectively. The numbers of scans were 64. The 2D data were zero-filled in t1 dimension to double the data points, multiplied by cosine-square-bell window functions in both t1 and t2 dimensions, and Fourier-transformed using software XWIN-NMR. The final real matrix sizes of these 2D spectra are 2048×256 and 2048×512 data points (F2×F1) for HMQC and HMBC, respectively.

Mass spectral analysis. The mass of samples was analyzed by (A) MALDI-TOF Mass Spectrometry and by (B) ESI-MS Mass spectrometry. (A) Samples for MALDI-TOF were first dissolved in acetonitrile, and then mixed with the matrix CHCA, i.e., Alpha-cyano-4-hydroxycinnamic acid, 10 mg CHCA/mL in 50:50 water/acetonitrile and 0.1% TFA in final concentration. The molecular weight was determined by the high resolution mass spectroscope analysis with standards. (B) For ESI, the sample was analyzed with LCQ DECA XP Plus machine made by Thermo Finnigan. It is ionized with ESI source and the solvent for the compound is acetonitrile.

Results

The profile of the proton NMR is presented in FIG. 18. The 2D NMR profiles of HMQC and HMBC are shown in FIGS. 19 and 20, respectively.

Table 5.1 summarizes the 2D NMR chemical shift data and the assignment of functional groups derived from these data. Based on these data and analysis, the structure of compound Y (Y3) is assigned as shown below.

Figure 17: Structure of Compound Y

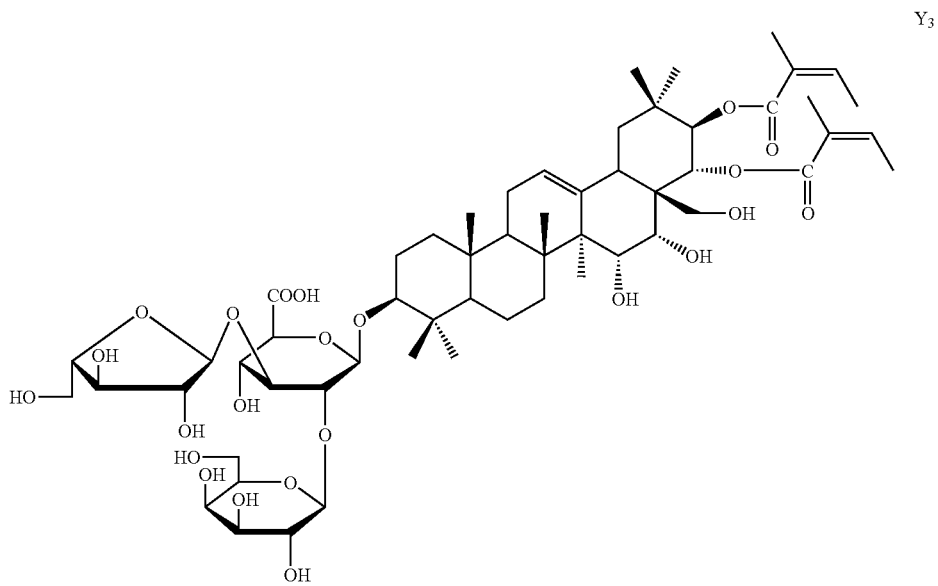

The chemical name of compound Y is: 3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene.

TABLE 5.1

13C and 1H NMR Data for Compound Y (in Pyridine-d5)[a]

| Position | C | H | Key HMBC correlations |
|---|---|---|---|
| 1 | 38.7 | 0.83, 1.40 | C-3, C-5, C-9 |
| 2 | 26.4 | 1.81, 2.14 | — |
| 3 | 89.6 | 3.25, 1H, dd, 12.0/4.0 Hz | C-23, C-24, GlcA C-1' |
| 4 | 39.4 | — | — |
| 5 | 55.3 | 0.78 | — |
| 6 | 18.5 | 1.55, 1.59 | C-8, C-10 |
| 7 | 36.5 | 2.00, 2.10 | C-5, C-9 |
| 8 | 41.2 | — | — |
| 9 | 47.0 | 3.06 | C-7, C-8, C-12, C-14, C-26 |
| 10 | 37.2 | — | — |
| 11 | 23.7 | 1.74, 1.89 | — |
| 12 | 125.2 | 5.49, 1H, br s | C-9, C-11, C-14, C-18 |
| 13 | 143.4 | — | — |
| 14 | 47.5 | — | — |
| 15 | 67.3 | 4.21 | C-8, C-27 |
| 16 | 73.6 | 4.45 | C-14, C-15, C-18 |
| 17 | 48.3 | — | — |

TABLE 5.1-continued 13C and 1H NMR Data for Compound Y (in Pyridine-d5)[a]

| Position | C | H | Key HMBC correlations |
|---|---|---|---|
| 18 | 40.8 | 3.07 | C-12, C-13, C-14, C-16, C-19, C-20, C-28, |
| 19 | 46.8 | 1.41, 1.69 | — |
| 20 | 36.2 | — | |
| 21 | 79.3 | 6.71, 1H, d, 10 Hz | C-20, C-22, C-29, C-30, 21-O-Ang C-1'''' |
| 22 | 73.5 | 6.32, 1H, d, 10 Hz | C-16, C-17, C-21, C-28, 22-O-Ang C-1'''' |
| 23 | 27.7 | 1.26, 3H, s | C-3, C-4, C-5, C-24 |
| 24 | 16.5 | 1.16, 3H, s | C-3, C-4, C-5, C-23 |
| 25 | 16.0 | 0.81, 3H, s | C-1, C-5, C-9, C-10 |
| 26 | 17.3 | 0.99, 3H, s | C-7, C-8, C-9, C-14 |
| 27 | 21.0 | 1.85, 3H, s | C-8, C-13, C-14, C-15 |
| 28 | 62.9 | 3.50, 1H, d, 11.0 Hz, 3.76, 1H, d, 11.0 Hz, | C-16, C-17, C-18, C-22 |
| 29 | 29.2 | 1.09, 3H, s | C-19, C-20, C-21, C-30 |
| 30 | 20.0 | 1.32, 3H, s | C-19, C-20, C-21, C-29 |
| GlcA | | | |
| 1' | 104.9 | 4.89, 1H, d, 7.8 Hz | C-3 |
| 2' | 79.1 | 4.38 | GlcA C-1', C-3', Gal C-1'' |
| 3' | 86.1 | 4.20 | GlcA C-2', C-4', Ara C-1''' |
| 4' | 71.5 | 4.42 | GlcA C-3', C-5', C-6' |
| 5' | 78.0 | 4.52 | GlcA C-4', C-6' |
| 6' | 171.9 | — | — |
| Gal | | | |
| 1'' | 104.6 | 5.32, 1H, d, 7.7 Hz | GlcA C-2' |
| 2'' | 73.6 | 4.42 | Gal C-1'', C-3'' |
| 3'' | 74.9 | 4.10 | Gal C-2'' |
| 4'' | 69.5 | 4.56 | Gal C-2'', C-3'' |
| 5'' | 76.4 | 3.94 | Gal C-4'', C-6'' |
| 6'' | 61.6 | 4.43, 4.52 | Gal C-4'', C-5'' |
| Ara-f | | | |
| 1''' | 110.6 | 6.03. 1H, br s | GlcA C-3', Ara C-2''', C-4''' |
| 2''' | 83.4 | 4.94 | Ara C-3''' |
| 3''' | 78.3 | 4.78 | Ara C-2''' |
| 4''' | 85.2 | 4.82 | Ara C-5''' |
| 5''' | 62.2 | 4.12, 4.28 | Ara C-3''' |
| 21-O-Ang | | | |
| 1'''' | 167.7 | — | — |
| 2'''' | 129.6 | — | — |
| 3'''' | 137.2 | 5.96, 1H, dq, 7.0/1.5 Hz | Ang C-1'''', C-4'''', C-5'''' |
| 4'''' | 15.5 | 2.10, 3H, dq, 7.0/1.5 Hz | Ang C-2'''', C-3'''' |
| 5'''' | 20.8 | 2.00, 3H, s | Ang C-1'''', C-2'''', C-3'''' |
| 22-O-Ang | | | |
| 1'''' | 167.9 | — | — |
| 2'''' | 129.8 | — | — |
| 3'''' | 136.3 | 5.78, 1H, dq, 7.0/1.5 Hz | Ang C-1'''', C-4'''', C-5'''' |
| 4'''' | 15.5 | 1.93, 3H, dq, 7.0/1.5 Hz | Ang C-2'''', C-3'''' |
| 5'''' | 20.5 | 1.74, 3H, s | Ang C-1'''', C-2'''', C-3'''' |

[a]The data were assigned based on HMQC and HMBC correlations.

The mass spectrum of compound Y as determined by MALDI-TOF and ESI-MS, i.e., see FIG. 21, 22, indicates that the mass of compound Y is 1140.57 which agree with the theoretical mass of the compound Y.

Conclusion

The active compound Y isolated from extract of *Xanthoceras sorbifolia* is an oleanene triterpenoidal saponin with a trisaccharide chain attached at C-3 of the aglycone and two angeloyl groups acylated at C-21 and C-22. The formula of Y is $C_{57}H_{88}O_{23}$, and the chemical name of Compound Y is: 3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene.

Experiment 6

Determination of the Chemical Structure of Compound Y1 of *Xanthoceras Sorbifolia* Extract Methods The method for NMR and MS analysis for compound Y1 is similar to the method described in Experiment 5.

Results

The spectrum of the H-NMR is presented in FIG. 24. The 2D NMR spectra of HMQC, HMBC and COSY are shown in FIGS. 25, 26 and 27, respectively. Table 6.1 summarizes the chemical shift data and the assignment of functional groups derived from these data.

TABLE 6.1

13C and 1H NMR Data for Compound Y1 (in Pyridine-d5)

| Position | C | H |
|---|---|---|
| 1 | 38.6 | 0.85, 1.33 |
| 2 | 26.3 | 1.86, 2.10 |
| 3 | 89.7 | 3.25, 1H, dd |
| 4 | 39.5 | — |
| 5 | 55.5 | 0.75 |
| 6 | 18.3 | 1.40, 1.43 |
| 7 | 33.1 | 1.20, 1.50 |
| 8 | 40.0 | — |
| 9 | 46.7 | 1.69 |
| 10 | 36.5 | — |
| 11 | 22.5 | 2.30 |
| 12 | 123.6 | 5.36, 1H, br s |
| 13 | 143.5 | — |
| 14 | 41.8 | — |
| 15 | 34.7 | 1.53, 1.73 |
| 16 | 68.5 | 4.45 |
| 17 | 48.2 | — |
| 18 | 39.9 | 3.04 |
| 19 | 47.6 | 1.30, 3.05 |
| 20 | 36.7 | — |
| 21 | 85.3 | 5.05, 1H, d |
| 22 | 73.8 | 6.17, 1H, d |
| 23 | 27.7 | 1.29, 3H, s |
| 24 | 16.5 | 1.16, 3H, s |
| 25 | 15.5 | 0.81, 3H, s |
| 26 | 17.1 | 0.82, 3H, s |
| 27 | 20.6 | 1.83, 3H, s |
| 28 | 63.7 | 3.42, 1H, d, 3.60, 1H, d |
| 29 | 29.9 | 1.42, 3H, s |
| 30 | 19.9 | 1.37, 3H, s |
| GlcA | | |
| 1 | 105.0 | 4.88, 1H, d |
| 2 | 79.0 | 4.37 |
| 3 | 86.0 | 4.20 |
| 4 | 71.6 | 4.43 |
| 5 | 78.0 | 4.50 |
| 6 | 171.8 | — |
| Gal | | |
| 1 | 104.5 | 5.31, 1H, d |
| 2 | 73.5 | 4.43 |
| 3 | 74.9 | 4.10 |
| 4 | 69.5 | 4.57 |
| 5 | 76.3 | 3.95 |
| 6 | 61.1 | 4.44, 4.53 |
| Ara-f | | |
| 1 | 110.9 | 6.04. 1H, br s |
| 2 | 83.3 | 4.95 |
| 3 | 78.3 | 4.78 |
| 4 | 85.2 | 4.82 |
| 5 | 62.0 | 4.13, 4.31 |

TABLE 6.1-continued 13C and 1H NMR Data for Compound Y1 (in Pyridine-d5)

| Position | C | H |
|---|---|---|
| 21-O-Rha | | |
| 1 | 105.1 | 4.92, 1H, d |
| 2 | 70.5 | 4.25 |
| 3 | 74.0 | 5.59 |
| 4 | 71.5 | 5.70 |
| 5 | 68.5 | 3.89 |
| 6 | 17.6 | 1.18, 3H, d |
| Rh-3-Ang | | |
| 1 | 167.2 | — |
| 2 | 127.9 | — |
| 3 | 138.7 | 5.92, 1H, q |
| 4 | 15.7 | 2.02, 3H, d |
| 5 | 20.6 | 1.92, 3H, s |
| Rh-4-Ang | | |
| 1 | 167.2 | — |
| 2 | 128.0 | — |
| 3 | 137.9 | 5.87, 1H, q |
| 4 | 15.5 | 1.96, 3H, d |
| 5 | 19.8 | 1.85, 3H, s |
| 22-O-Ac | | |
| 1 | 171.4 | — |
| 2 | 21.8 | 2.31, 3H, s |

Based on these data and analysis, the structure of compound Y1 is assigned and shown below.

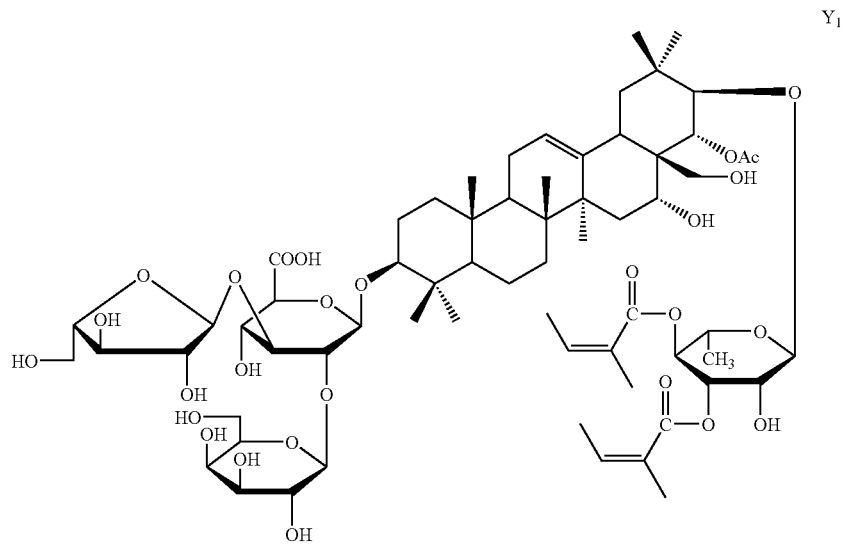

Figure 23. Structure of Y1

The chemical name of Y1 is: 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β, 16α, 21β, 22α, 28-pentahydroxyolean-12-ene.

Conclusion

Compound Y1 isolated from extract of *Xanthoceras sorbifolia* is a bisdesmosidic polyhydroxyoleanene triterpenoidal saponin with a trisaccharide chain at C-3 of the backbone and a monosaccharide moiety at C-21 where two angeloyl groups were acylated at C-3 and C-4 position. The formula of Y1 is $C_{65}H_{100}O_{27}$.

Experiment 7

Determination of the Chemical Structure of Compound Y2 of *Xanthoceras Sorbifolia* Extract.

Methods

The method for NMR and MS analysis for compound Y2 is similar to the method described in Experiment 5.

Results

The 1D and 2D NMR spectra of H-NMR, C-13 NMR, HMQC, HMBC and (TOCSY) and MS (MALDI-TOF) of Y2 are showed in FIGS. 29-34. Table 7.1 summarizes the 1D and 2D NMR chemical shift data and the assignment of functional groups derived from these data.

TABLE 7.1

13C and 1H NMR data for Y2 (in Pyridine-d5)[a]

| Position | C | H |
|---|---|---|
| 1 | 38.4 | 0.83, 1.36 |
| 2 | 26.4 | 1.89, 2.25 |
| 3 | 91.3 | 3.39, 1H, m |
| 4 | 43.4 | — |
| 5 | 56.7 | 0.87, 1H, d, 12.0 Hz |

TABLE 7.1-continued 13C and 1H NMR data for Y2 (in Pyridine-d5)[a]

| Position | C | H |
|---|---|---|
| 6 | 18.6 | 1.31, 1.57 |
| 7 | 36.3 | 1.97, 2.12 |
| 8 | 40.7 | — |
| 9 | 46.7 | 1.63 |

TABLE 7.1-continued 13C and 1H NMR data for Y2 (in Pyridine-d5)[a]

| Position | C | H |
|---|---|---|
| 10 | 36.6 | — |
| 11 | 23.9 | 1.69, 1.89 |
| 12 | 125.1 | 5.48, 1H, br s |
| 13 | 143.4 | — |
| 14 | 47.5 | — |
| 15 | 67.1 | 4.18, 1H, d, 4.1 Hz |
| 16 | 73.2 | 4.43 |
| 17 | 48.1 | — |
| 18 | 41.4 | 3.06 |
| 19 | 46.6 | 1.40, 3.08 |
| 20 | 36.1 | — |
| 21 | 78.3 | 6.69, 1H, d, 10.2 Hz |
| 22 | 73.1 | 6.30, 1H, d, 10.2 Hz |
| 23 | 22.0 | 1.29, 3H, s |
| 24 | 62.9 | 3.28, 1H, d, 11.2 Hz; 4.32 |
| 25 | 15.6 | 0.64, 3H, s |
| 26 | 17.1 | 0.94, 3H, s |
| 27 | 20.8 | 1.84, 3H, s |
| 28 | 63.1 | 3.48, 3.72 (each, 1H, d, 10.6 Hz) |
| 29 | 29.3 | 1.09, 3H, s |
| 30 | 20.0 | 1.32, 3H, s |
| 3-O-GlcA | | |
| 1 | 104.5 | 4.87, 1H, d, 7.2 Hz |
| 2 | 78.6 | 4.31 |
| 3 | 86.5 | 4.23 |
| 4 | 71.6 | 4.45 |
| 5 | 77.4 | 4.53 |
| 6 | 171.9 | |
| Glc | | |
| 1 | 103.7 | 5.48, 1H, d, 7.8 Hz |
| 2 | 75.3 | 4.02 |
| 3 | 78.0 | 4.31 |
| 4 | 69.3 | 4.52 |

TABLE 7.1-continued 13C and 1H NMR data for Y2 (in Pyridine-d5)[a]

| Position | C | H |
|---|---|---|
| 5 | 78.2 | 3.62 |
| 6 | 61.5 | 4.33, 4.50 |
| Ara | | |
| 1 | 110.1 | 6.05, 1H, br s |
| 2 | 83.5 | 4.97 |
| 3 | 77.8 | 4.74 |
| 4 | 85.0 | 4.84 |
| 5 | 62.2 | 4.18, 4.33 |
| 21-O-ang | | |
| 1 | 167.5 | — |
| 2 | 128.7 | — |
| 3 | 137.2 | 5.95, 1H, dd, 14.4/7.2 Hz |
| 4 | 16.7 | 2.08, 3H, d, 7.2 Hz |
| 5 | 20.6 | 2.00, 3H, s |
| 22-O-ang | | |
| 1 | 167.9 | — |
| 2 | 128.9 | — |
| 3 | 136.3 | 5.76, 1H, dd, 14.4/7.2 Hz |
| 4 | 15.6 | 1.95, 3H, dd, 7.2 Hz |
| 5 | 20.4 | 1.74, 3H, s |

[a]The data were assigned based on COSY, HMQC and HMBC correlations.

Conclusion

Based on these data and analysis, the compound Y2 isolated from extract of *Xanthoceras sorbifolia* is an oleanene triterpenoidal saponin with a trisaccharide chain attached at C-3 of the aglycone and two angeloyl groups acylated at C-21 and C-22. The chemical structure of Y2 is shown below. See also FIG. 28.

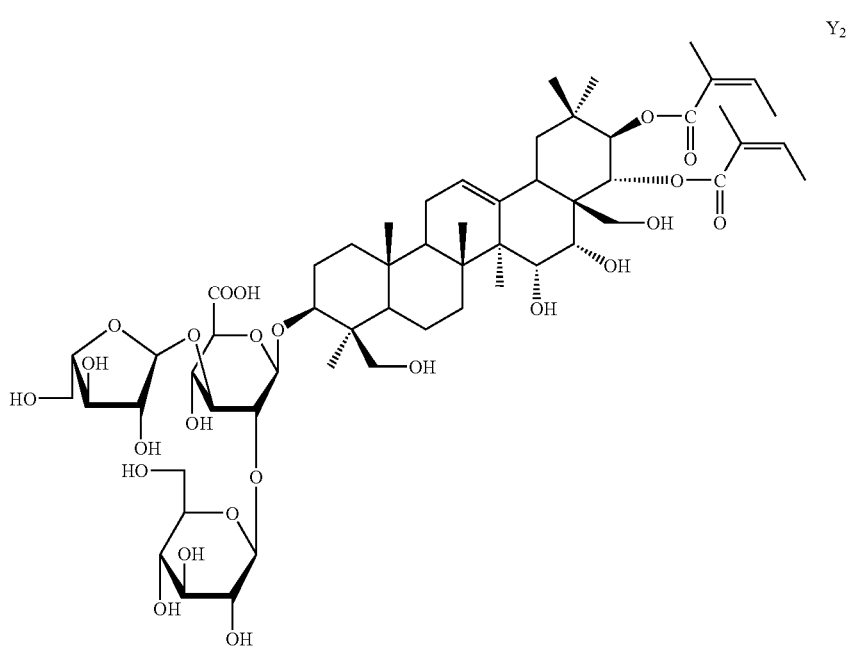

Y2

The formula of Y2 is $C_{57}H_{88}O_{24}$, and the chemical name of Compound Y2 is: 3-O-[β-D-glucopyranosyl-(1→2)]-α-L-arabinofuranosyl(1→3)-β-D-glucuronopyranosyl-21,22-O-diangeloyl-3β, 15α, 16α, 21β, 22α, 24β, 28-heptahydroxy-olean-12-ene.

Experiment 7B

Chemical Structure Analysis of Y4

Results of Y4 Analysis
The profile of the proton NMR of Y4 is presented in FIG. 58. The profiles of 2D NMR (HMQC) of Y4 is presented in FIG. 59.

Experiment 8

Purification of the Inhibition Components Y8-Y10 in the *Xanthoceras Sorbifolia* Extract (A) Fractionation of *Xanthoceras Sorbifolia* Extracts Components with FPLC Methods
The methods for this experiment are similar to the methods decribed in Experiment 4 Section (A) and (B).

Results
The elution profile shows 4-5 broad fractions. See FIG. 9. These fractions were analyzed with HPLC. FPLC fractions 63, 64 and 65 are further separated on 45% isocratic analysis, 4-5 major components were separated (FIG. 12). These fractions were assigned designations Y8, Y9 and Y10. These fractions were collected. Re-chromatography of the compound Y8, Y9 and Y10 showed a single peak in HPLC with a C18 reverse phase column. See FIG. 13.

(B) Inhibition Analysis with MTT Assay.
Inhibition analysis of purified compounds was determined with the MTT assay. Results indicate that compound Y8, Y9 and Y10 has activity against ovarian cancer cells (OCAR-3) with IC50 values of 3, 4 and 1.5 ug/ml, respectively. See FIG. 4.

Experiment 9

Determination of the Chemical Structure of Compound Y8 of *Xanthoceras Sorbifolia* Extract Methods
The method for NMR and MS analysis for compound Y8 is similar to the method described in Experiment 5.

Results
The spectral profiles of the H-NMR, C13-NMR 2D NMR (HMQC) of compound Y8 are presented in FIGS. 36-38.

Based on these data and analysis, the compound Y8 isolated from extract of *Xanthoceras sorbifolia* is an oleanene triterpenoidal saponin with a trisaccharide chain attached at C-3 of the aglycone and two angeloyl groups acylated at C-21 and C-22.

The formula of compound Y8 is $C_{57}H_{87}O_{23}$, and the chemical name of Y8 is: 3-O-[β-glucopyranosyl(1→2)]-α-arabinofuranosyl(1→3)-β-glucuronopyranosyl-21,22-O-diangeloyl-3β, 16α, 21β, 22α, 24β, 28-hexahydroxyolean-12-ene.

The chemical structure of compound Y8 is presented in the following figure. See also FIG. 35.

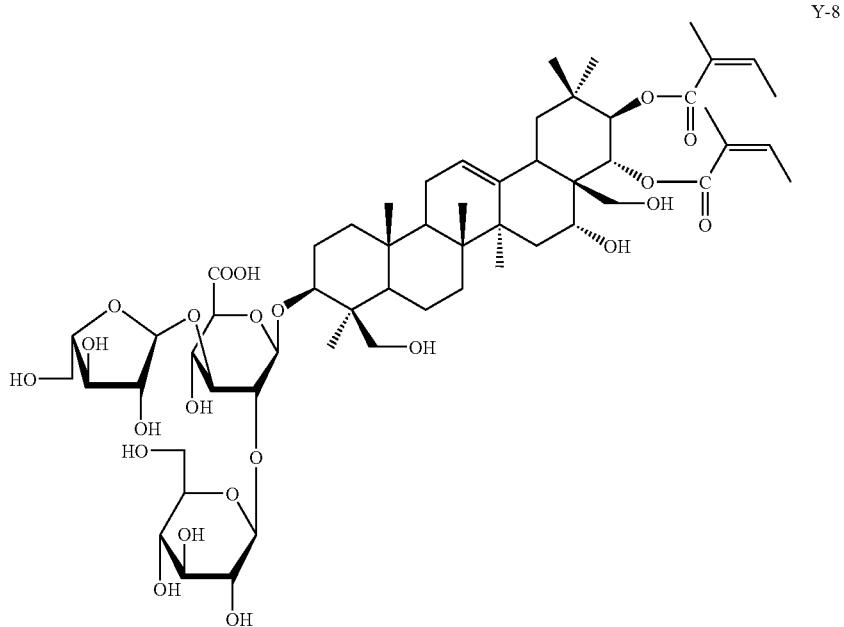

Experiment 10

Determination of the Chemical Structure of Compound Y9 of *Xanthoceras Sorbifolia* Extract Methods
The method for NMR and MS analysis for compound Y9 is similar to the method described in Experiment 5.

Results

The spectral profiles of the H-NMR, 2D NMR, i.e., HMQC and HMBC, of Y9 are shown in FIGS. 40-42.

Based on these data and analysis, compound Y9 isolated from extract of *Xanthoceras sorbifolia* is a bisdesmosidic polyhydroxyoleanene triterpenoidal saponin with a trisaccharide chain at C-3 of the backbone and a monosaccharide moiety at C-21 where two angeloyl groups were acylated at C-3 and C-4 position.

The formula of compound Y9 is $C_{63}H_{98}O_{26}$, and the chemical name of Y9 is: 3-O-[β-galactopyranosyl(1→2)]-α-arabinofuranosyl(1→3)-β-glucuronopyranosyl-21-O-(3,4-diangeloyl)-α-rhamnopyranosyl-3β, 16α, 21β, 22α, 28-pentahydroxyolean-12-ene.

The chemical structure of Compound Y9 is presented in the following figure. See also FIG. 39.

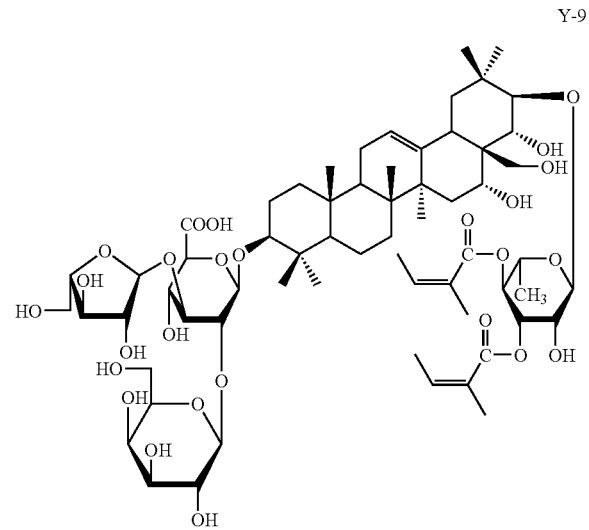

Y-9

Experiment 11

Determination of the Chemical Structure of Compound Y10 of *Xanthoceras Sorbifolia* Extract Methods The method for NMR and MS analysis for compound Y10 is similar to the method described in Experiment 5.

Results

The profile of the H-NMR, C13-NMR and 2D NMR (HMQC) are shown in FIGS. 44-46.

Based on these data and analysis, compound Y10 isolated from extract of *Xanthoceras sorbifolia* is an oleanene triterpenoidal saponin with a trisaccharide chain attached at C-3 of the aglycone and two angeloyl groups acylated at C-21 and C-22.

The formula of compound Y10 is $C_{57}H_{87}O_{22}$, and the chemical name of Y10 is: 3-O-[β-galactopyranosyl(1→2)]-α-arabinofuranosyl(1→3)-β-glucuronopyranosyl-21,22-O-diangeloyl-3β, 16α, 21β, 22α, 28-pentahydroxyolean-12-ene.

The chemical structure of Compound Y10 is presented in the following figure. See also FIG. 43.

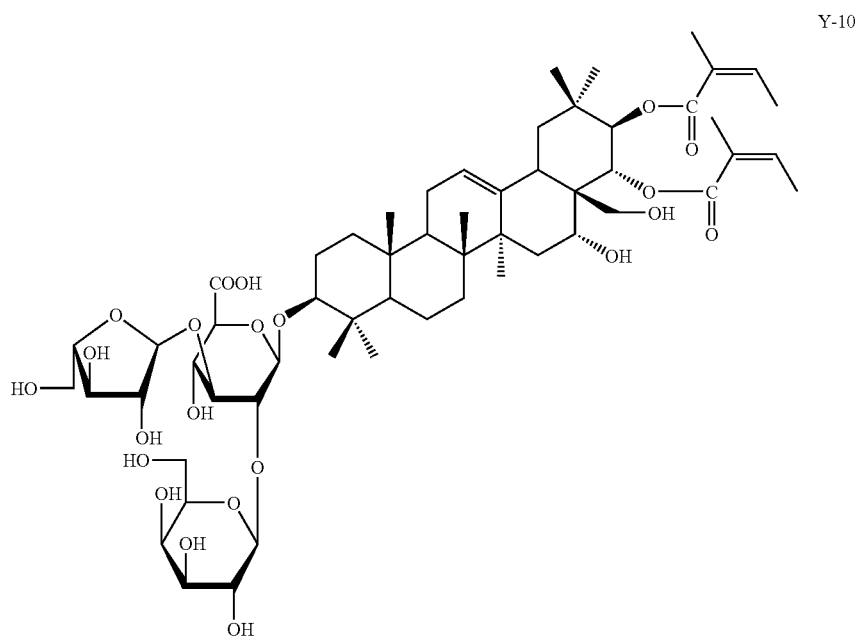

Y-10

Experiment 12

Purification of Component R from *Xanthoceras Sorbifolia* Extract (A) Purification of *Xanthoceras Sorbifolia* Extracts Components with FPLC and HPLC Methods The methods used are similar to the methods described in Experiment 4, section (A) and (B) except a 30% acetonitrile isocratic elution was used in HPLC for isolation of the Compound R.

Results

Fraction No. 39-41 from gradient elution of FPLC were pooled and further purified with an open ODS-C18 column with isocratic 30% acetonitrile elution. Six identifiable fractions in two groups were collected. Fractions 6-13 were further characterized with HPLC.

These fractions were further separated into 4-5 components with the 30% acetonitrile isocratic elution in a DeltaPak column. The fraction designated herein as "R1", is the major component. See FIG. 60A. The pure R1 was subsequently collected from the column elution. See FIG. 60B.

(B) Appearance and Solubility

The pure R1 appears as an amorphous white powder, soluble in aqueous alcohol, i.e., methanol or ethanol, 50% acetonitrile and 100% pyridine.

(C) Determination of the Chemical Structure of R1

Methods

The NMR and MS Analysis of R1 is similar to the method described in Experiment 5.

Results

The NMR spectra of pure R1 is presented in FIGS. 48-52. Based on chemical shift analysis, compound R1 isolated from extract of *Xanthoceras sorbifolia* is a triterpenoid saponins with five sugars and one angeloyl group attached to the sugar moiety. The chemical structure of R1 is shown in following figure. See also FIG. 47.

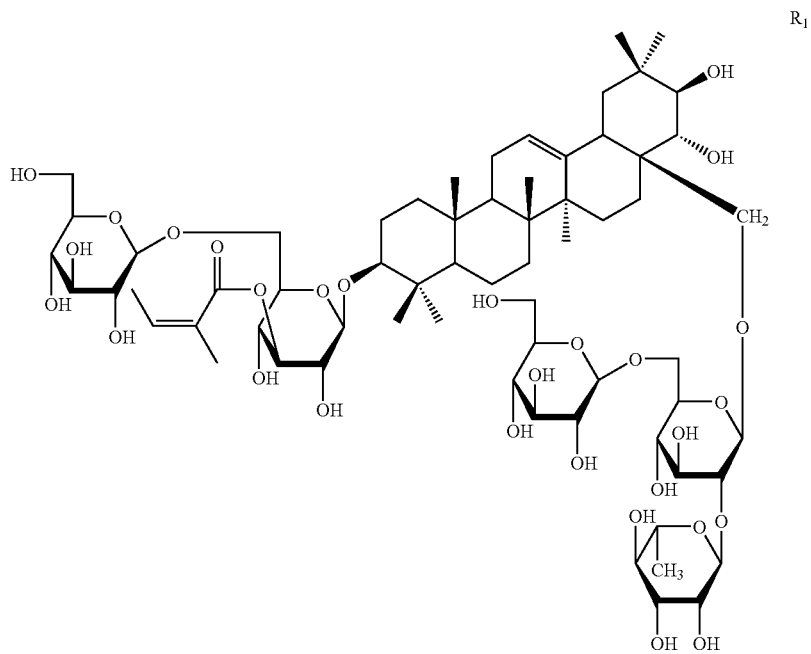

The formula of Compound R1 is $C_{65}H_{106}O_{29}$, and the chemical name of R1 is: 3-O-[angeloyl-(1→3)-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β, 21β, 22α, 28-tetrahydroxyolean-12-ene.

Experiment 13

Purification of Component-O from *Xanthoceras Sorbifolia* Extract (A) Fractionation of *Xanthoceras Sorbifolia* Extracts Components with FPLC and HPLC Methods The methods used are similar to the methods described in Experiment 4, section (A) and (B) except a 20% acetonitrile isocratic elution was used in HPLC for isolation of the Compound O.

Results

Fractions obtained from FPLC were analyzed with HPLC. By comparison with the profiles of the original sample, a specific component, in this case fraction O, was identified (#28-30). Fraction O was collected for further purification. Sixteen identifiable HPLC fractions were observed in the elution profiles. See FIG. 61. Fractions 28, 34 and 54 were further purified. See FIGS. 62-63. These purified components are named as compound O28, O34 and O54, respectively.

(B) Appearance and Solubility

The purified compound O23 and O34 are light yellow amorphous powder, soluble in aqueous alcohol, i.e., methanol, ethanol, 50% acetonitrile and 100% pyridine. The purified compound O54 is a white amorphous powder, soluble in aqueous alcohol, i.e., methanol, ethanol, 50% acetonitrile and 100% pyridine.

(C) Structure Analysis of Compound O54

Methods

The NMR and MS analysis of O54 is similar to the method described in Experiment 5.

Results

The NMR spectra of compound O54 is presented in FIGS. 54-56. Based on the chemical shift analysis, compound O54 isolated from extract of *Xanthoceras sorbifolia* is a bisdesmosidic polyhydroxyoleanene triterpenoidal glycoside with a disaccharide chain [βD-glucopyranosyl-(1→6)-β-D-glucopyranoside] affixed to C-3 and a trisaccharide chain [a-L-rhamnopyranosyl-(1→2)-β-D-glucopyranosyl-(1→6)-β-D-glucopyranosyl ester]attached to C-28. The chemical structure of compound O54 is presented in the following figure. See also FIG. 53.

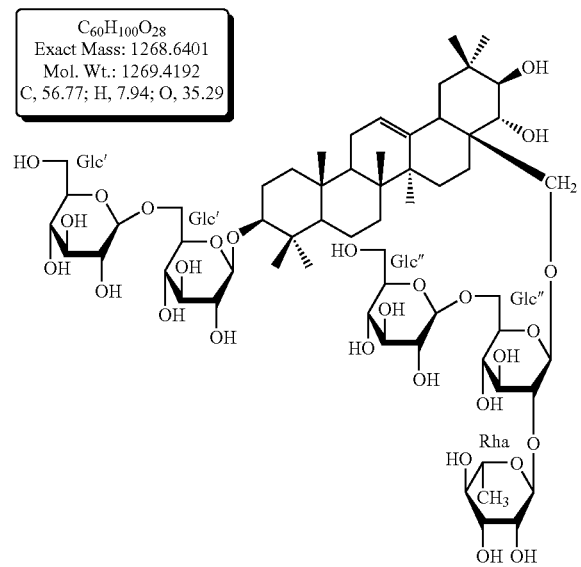

The formula of compound O54 is $C_{60}H_{100}O_{28}$, and the chemical name of O54 is: 3-O-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β, 21β, 22α, 28-tetrahydroxyolean-12-ene.

Although the present invention has been described in detail with particular reference to preferred embodiments thereof, it should be understood that the invention is capable of other different embodiments, and its details are capable of modifications in various obvious aspects. As is readily apparent to those skilled in the art, variations and modifications can be affected while remaining within the spirit and scope of the invention. Accordingly, the foregoing disclosure, description, and figures are for illustrative purpose only, and do not in any way limit the invention which is defined only by the claims.

REFERENCES

1. Carmichael, J., DeGraff, W. G., Gazdar, A. F., Minna, J. D. and Mitchell, J. B.: Evaluation of a tetrazolium-based semiautomated calorimetric assay: assessment of chemosensitivity testing. Cancer Res. 47:936-942 (1987).
2. Chen, Q. 1995. Methods of study on pharmacology of Chinese medicines. Press of People's Public Health, Beijing. p 892.
3. Huang, Zh. Sh., Liu, M. P., Chen, Ch. Zh. 1997. Study on effects of Yangshou Dan on improving learning and retention. Chinese Journal of combination of Chinese and west medicine, 9(17): 553.
4. Zhang, Y., Zhang, H. Y., Li, W. P. 1995. Study on effects of Anjifu on improving intelligence, Chinese Bulletin of Pharmacology, 11 (3): 233.
5. Yang, J., Wang, J., Feng, P. A. 2000. Study on effects of Naokkangtai capsule on improving learning and retention in mice, New Chinese Medicine and Clinical Pharmacology, 1(11): 29.
6. Yang, J., Wang, J., Zhang, J. Ch. 2000. Study on effects of Crude saponins of peonies on improving learning and retention in mice, Chinese journal of Pharmacology, 2(16): 46.
7. Xia, W. J., Jin, M. W., Zhang, L. 2000. Study on treatment of senile dementia caused by angio-aging with Didang tang, Pharmacology and Clinical of Chinese Medicines, 16 (4).
8. Bian, H. M., Yu, J. Z., Gong, J. N. 2000. Study on effects of Tongmai Yizhi capsule on improving learning and retention in mice, Pharmacology and Clinical of Chinese Medicines, 16 (5): 40.
9. Wei, X. L., Zhang, Y. X. 2000. Study of animal model for studying senile dementia, Chinese journal of Pharmacology, 8(16): 372.
10. Bureau of Medicinal Police, Department of Public Health. Guide line for study of effect of medicines for treatment of nervous system diseases, in Guidebook of study of new medicine. p 45.
11. Zhang, D. Sh., Zhang, J. T. 2000. Effects of crude Ginseng saponins on improving impairment induced by B-peptide, Chinese journal of Pharmacology, 8(16): 22.

What is claimed is:
1. An isolated compound of formula (1):

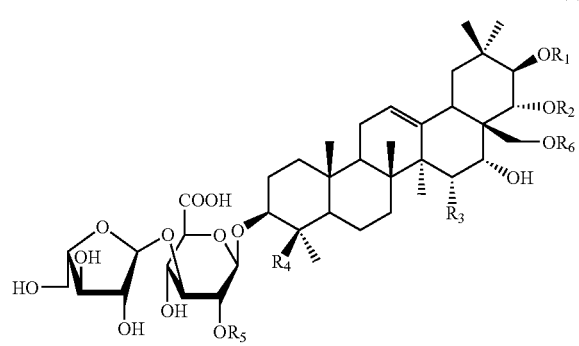

(1)

or a salt, or ester thereof, wherein:
R₁, R₂ represents angeloyl group or sugar moiety with diangeloyl groups;
R₃ represents OH or H;
R₄ represents CH₃ or CH₂OH; and
R₅ represents D-glucose or D-Galactose
R₆ represents H or Ac.

2. The compound of claim 1, wherein R3 is H.
3. The compound of claim 1, wherein R3 is OH.
4. The compound of claim 1, wherein R4 is CH3.
5. The compound of claim 1, wherein R4 is CH2OH.
6. The compound of claim 1, wherein R5 is D-glucose.
7. The compound of claim 1, wherein R5 is D-Galactose.
8. A method for inhibiting cancer cell growth, wherein the cancer comprising ovarian cancer, comprising administering to said subject an effective amount of an isolated compound selected from a compound of formula (3):

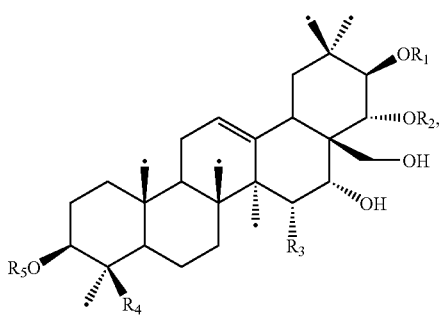

(3)

a salt, or ester thereof,
wherein:
R₁ represents angeloyl group;
R₂ represents angeloyl group;
R₃ represents OH or H;
R₄ represents CH₃ or CH₂OH; and
R₅ represents sugar moiety or sugar chain, wherein the sugar is selected from the group consisting of: D-glucose, D-galactose, L-rhamnose, L-arabinose, D-xylose, alduronic acid, D-glucuronic acid and D-galacturonic acid.

9. An isolated compound selected from a compound of formula (4)

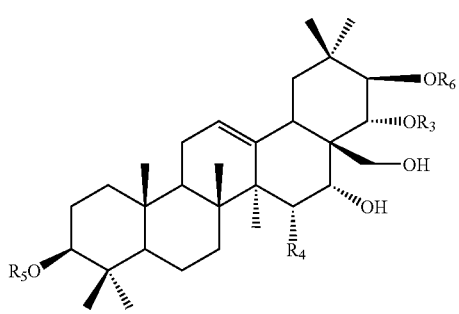

(4)

a salt, or ester thereof, wherein:
R6 represents sugar moiety with diangeloyl groups in trans-position
R3 represents Ac or H;
R4 represents H or OH; and
R5 represents sugar moiety or sugar chain, wherein at least one the sugar is selected from the group consisting of: D-glucose, D-galactose, L-rhamnose, L-arabinose, D-xylose, alduronic acid, D-glucuronic acid and D-galacturonic acid.

10. A composition consisting essentially of an amount of the compound of claims 1 effective for inhibiting ovarian cancer cell growth.
11. The composition for inhibiting ovarian cancer cell growth, consisting essentially of an amount of the compound of claims 1 further comprising a pharmaceutically suitable carrier.
12. A method for inhibiting ovarian cancer cell growth in a subject, comprising administering to the subject an effective amount of the compound of claim 1.
13. A method for inhibiting ovarian cancer cell growth in a subject, comprising administering to the subject an effective amount of the compound of claim 8.
14. A composition consisting essentially of an amount of the compound of claim 9 effective for inhibiting ovarian cancer cell growth.
15. The composition for inhibiting ovarian cancer cell growth, consisting essentially of an amount of the compound of claim 9 further comprising a pharmaceutically suitable carrier.
16. A method for inhibiting ovarian cancer cell growth in a subject, comprising administering to the subject an effective amount of the compound of claim 9.
17. A composition consisting essentially of an amount of the compound of claim 1 effective for inhibiting bladder, bone, leukocyte, liver, prostate, breast or brain cancer cells growth.
18. A method for inhibiting bladder, bone, leukocyte, liver, prostate, breast or brain cancer cell growth in a subject, comprising administering to the subject an effective amount of the compound of claim 1.
19. A method for inhibiting bladder, bone, leukocyte, liver, prostate, breast or brain cancer cell growth in a subject, comprising administering to the subject an effective amount of the compound of claim 8.
20. A composition consisting essentially of an amount of the compound of claim 9 effective for inhibiting bladder, bone, leukocyte, liver, prostate, breast or brain cancer cells growth.
21. A method for inhibiting bladder, bone, leukocyte, liver, prostate, breast or brain cancer cell growth in a subject, comprising administering to the subject an effective amount of the compound of claim 9.
22. The method of claim 16, comprising administering to the subject an effective amount of the compound wherein the compound has a triterpene and sugar moiety with diangeloyl groups in the trans-position.
23. The method of claim 8, comprising administering to the subject an effective amount of the compound wherein the compound has a triterpene with diangeloyl groups in the trans-position.

* * * * *